(12) United States Patent
Yu et al.

(10) Patent No.: US 11,098,139 B2
(45) Date of Patent: Aug. 24, 2021

(54) ADVANCED QUALITY CONTROL TOOLS FOR MANUFACTURING BIMODAL AND MULTIMODAL POLYETHYLENE RESINS

(71) Applicant: Chevron Phillips Chemical Company LP, The Woodlands, TX (US)

(72) Inventors: Youlu Yu, Bartlesville, OK (US); Paul J. DesLauriers, Owasso, OK (US); Yongwoo Inn, Bartlesville, OK (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 390 days.

(21) Appl. No.: 15/908,033

(22) Filed: Feb. 28, 2018

(65) Prior Publication Data

US 2019/0263943 A1 Aug. 29, 2019

(51) Int. Cl.
| | | |
|---|---|---|
| *C08F 10/02* | (2006.01) | |
| *B01J 19/00* | (2006.01) | |
| *B01J 19/24* | (2006.01) | |

(52) U.S. Cl.
CPC ........... *C08F 10/02* (2013.01); *B01J 19/0006* (2013.01); *B01J 19/2445* (2013.01);
(Continued)

(58) Field of Classification Search
None
See application file for complete search history.

(56) References Cited

U.S. PATENT DOCUMENTS

| | | |
|---|---|---|
| 3,248,179 A | 4/1966 | Norwood |
| 4,501,885 A | 2/1985 | Sherk et al. |

(Continued)

FOREIGN PATENT DOCUMENTS

| | | | |
|---|---|---|---|
| EP | 1756175 B1 | 2/2014 | |
| WO | WO-9633226 A1 * | 10/1996 | ............... C08K 5/14 |
| WO | 1998029787 A1 | 7/1998 | |

OTHER PUBLICATIONS

The Engineering ToolBox webpage for Absolute, Dynamic and Kinematic Viscosity. https://www.engineeringtoolbox.com/dynamic-absolute-kinematic-viscosity-d_412.html. Archived at web.archive.org Jan. 18, 2017. Retrieved Feb. 6, 2020. (Year: 2017).*

(Continued)

*Primary Examiner* — Richard A Huhn
(74) *Attorney, Agent, or Firm* — Conley Rose, P.C.

(57) ABSTRACT

A method of determining multimodal polyethylene quality comprising the steps of (a) providing a multimodal polyethylene resin sample; (b) determining, in any sequence, the following: that the multimodal polyethylene resin sample has a melt index within 30% of a target melt index; that the multimodal polyethylene resin sample has a density within 2.5% of a target density; that the multimodal polyethylene resin sample has a dynamic viscosity deviation (% MVD) from a target dynamic viscosity of less than about 100%; that the multimodal polyethylene resin sample has a weight average molecular weight ($M_w$) deviation (% $M_w$D) from a target $M_w$ of less than about 20%; and that the multimodal polyethylene resin sample has a gel permeation chromatography (GPC) curve profile deviation (% GPCD) from a target GPC curve profile of less than about 15%; and (c) responsive to step (b), designating the multimodal polyethylene resin sample as a high quality resin.

17 Claims, 6 Drawing Sheets

(52) U.S. Cl.
CPC ............... *B01J 2219/0024* (2013.01); *B01J 2219/00193* (2013.01); *B01J 2219/00213* (2013.01); *C08F 2400/02* (2013.01); *C08F 2500/00* (2013.01); *C08F 2500/05* (2013.01); *C08F 2500/12* (2013.01); *C08F 2500/17* (2013.01)

(56) References Cited

U.S. PATENT DOCUMENTS

| | | | |
|---|---|---|---|
| 4,588,790 | A | 5/1986 | Jenkins, III et al. |
| 5,352,749 | A | 10/1994 | DeChellis et al. |
| 5,436,304 | A | 7/1995 | Griffin et al. |
| 5,565,175 | A | 10/1996 | Hottovy et al. |
| 5,575,979 | A | 11/1996 | Hanson |
| 5,739,220 | A | 4/1998 | Shamshoum et al. |
| 6,225,421 | B1 | 5/2001 | Promel et al. |
| 6,239,235 | B1 | 5/2001 | Hottovy et al. |
| 6,262,191 | B1 | 7/2001 | Hottovy et al. |
| 6,541,413 | B1* | 4/2003 | Razavi ............. C08F 210/16 502/152 |
| 6,833,415 | B2 | 12/2004 | Kendrick et al. |
| 7,163,906 | B2 | 1/2007 | McDaniel et al. |
| 7,619,047 | B2 | 11/2009 | Yang et al. |
| 7,790,820 | B2 | 9/2010 | Jensen et al. |
| 7,960,487 | B2 | 6/2011 | Yang et al. |
| 8,138,113 | B2 | 3/2012 | Yang et al. |
| 8,207,280 | B2 | 6/2012 | Murray et al. |
| 8,268,944 | B2 | 9/2012 | Yang et al. |
| 8,450,436 | B2 | 5/2013 | Masino et al. |
| 9,023,945 | B2 | 5/2015 | Mavridis et al. |
| 9,181,372 | B2 | 11/2015 | Yang et al. |
| 9,845,367 | B2 | 2/2017 | Ding et al. |
| 9,850,330 | B2 | 12/2017 | Kufeld et al. |
| 2004/0059070 | A1 | 3/2004 | Whitte et al. |
| 2005/0085598 | A1* | 4/2005 | Sandell ............... B01J 8/1809 526/64 |
| 2007/0298508 | A1 | 12/2007 | DesLauriers et al. |
| 2009/0156749 | A1* | 6/2009 | Nummila-Pakarinen .......... C08L 23/06 525/240 |
| 2012/0040878 | A1* | 2/2012 | Katayama ............ C08F 10/00 508/591 |
| 2012/0220738 | A1* | 8/2012 | Mannebach ......... C08F 110/02 526/64 |
| 2017/0015768 | A1* | 1/2017 | Mariott ............... C08F 4/645 |

OTHER PUBLICATIONS

Huang, J. C.-K. et al., "Effects of Hydrogen and 1-Butene Concentrations on the Molecular Properties of Polyethylene Produced by Catalytic Gas-Phase Polymerization". Ind. Eng. Chem. Res., vol. 36, No. 4, 1997. (Year: 1997).*

Wild, L., "Gel Permeation Chromatography of Polyethylene: Effect of Long-Chain Branching". J. Polym. Sci.: Part A-2 1967, 5, 1087-1101. (Year: 1967).*

Ullmann's Encyclopedia of Industrial Chemistry. Wiley-VCH Verlag GmbH & Co. KGaA, Weinheim. 2012. Fluid Mechanics. (Year: 2012).*

International Search Report dated May 20, 2019, issued in corresponding Application No. PCT/US2019/018863, 4 pages.

M. Ohshima, et al., "Quality Control of Polymer Production Processes,", Journal of Process Control, Oxford, GB, vol. 10, No. 2-3, Apr. 1, 2000, pp. 135-148.

J. Kang, et al., "Fast and Reliable Computational Strategy for Developing a Rigorous Model-Driven Soft Sensor of Dynamic Molecular Weight Distribution," Journal of Process Control, Oxford, GB, vol. 56, Jun. 7, 2017, pp. 79-99.

F. P. Alt, et al., "Bimodal Polyethylene—Interplay of Catalyst and Process,", Macromolecular Sympo, Wiley VCH Verlag, Weinheim, DE, vol. 163, No. 1, Jan. 1, 2001, pp. 135-144.

McNaught, Alan D., et al., "Compendium of Chemical Terminology," IUPAC Recommendations, Second edition, 1997, 5 pages, Wiley-Blackwell.

* cited by examiner

ADVANCED QUALITY CONTROL TOOLS FOR MANUFACTURING BIMODAL AND MULTIMODAL POLYETHYLENE RESINS

TECHNICAL FIELD

The present disclosure generally relates to the production of polyethylene. More specifically, this disclosure relates to a process for the production of multimodal polyethylene.

BACKGROUND

Conventionally, melt index and density are the primary quality control targets for polyethylene (PE) manufacturing plants to meet. Generally, when PE resins meet both melt index and density targets, such resins are generally regarded as on-spec resins; otherwise, resins are downgraded. While this approach can be successful for screening unimodal PE resins, owing to a correlation between unimodal resin melt index, and molecular weight and molecular weight distribution; it is challenging to judge the quality of a multimodal resin based solely on melt index and density. Thus, there is an ongoing need for developing efficient processes for controlling the quality of multimodal PE.

BRIEF SUMMARY

Disclosed herein is a method of producing polyethylene comprising (a) polymerizing ethylene in one or more reaction zones to produce a first polyethylene resin, wherein each reaction zone of the one or more reaction zones operates independently at a first value for a plurality of parameters, and wherein each parameter of the plurality of parameters is selected from the group consisting of ethylene concentration, comonomer concentration, hydrogen to ethylene ratio, temperature, catalyst concentration, cocatalyst concentration, pressure, and residence time, (b) determining a dynamic viscosity ($\eta_s^*$) of the first polyethylene resin, (c) comparing the dynamic viscosity of the first polyethylene resin with a target dynamic viscosity ($\eta_c^*$), wherein comparing the dynamic viscosity comprises calculating a dynamic viscosity deviation (% MVD) from the target dynamic viscosity, and wherein the first polyethylene resin is characterized by a % MVD of equal to or greater than about 100%, (d) selecting a second value for one or more parameters of the plurality of parameters for at least one of the one or more reaction zones, wherein the second value decreases the % MVD of the polyethylene resin, (e) operating the at least one of the one or more reaction zones independently at the second value of the one or more parameters of the plurality of parameters, and (f) recovering a second polyethylene resin from the one or more reaction zones, wherein the second polyethylene resin is characterized by a % MVD of less than about 100%. One or more aspects or steps of the method described in this paragraph can be implemented with one or more computers such as shown in FIG. 2, for example via a processor executing software code stored in memory that implements one or more aspects or steps of the methods disclosed herein.

Also disclosed herein is a method of producing polyethylene comprising (a) polymerizing ethylene in one or more reaction zones to produce a first polyethylene resin, wherein each reaction zone of the one or more reaction zones operates independently at a first value for a plurality of parameters, and wherein each parameter of the plurality of parameters is selected from the group consisting of ethylene concentration, comonomer concentration, hydrogen to ethylene ratio, temperature, catalyst concentration, cocatalyst concentration, pressure, and residence time, (b) determining a gel permeation chromatography (GPC) curve profile of the first polyethylene resin; wherein the GPC curve profile comprises a differential weight fraction (dw/d(log M)) as a function of log M, wherein M is the molecular weight of the weight fraction w, (c) comparing the GPC curve profile of the first polyethylene resin with a target GPC curve profile, wherein comparing the GPC curve profile comprises calculating a GPC curve profile deviation (% GPCD) from the target GPC curve profile, and wherein the first polyethylene resin is characterized by a % GPCD of equal to or greater than about 15%, (d) selecting a second value for one or more parameters of the plurality of parameters for at least one of the one or more reaction zones, wherein the second value decreases the % GPCD of the polyethylene resin, (e) operating the at least one of the one or more reaction zones independently at the second value of the one or more parameters of the plurality of parameters, and (e) recovering a second polyethylene resin from the one or more reaction zones, wherein the second polyethylene resin is characterized by a % GPCD of less than about 15%. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a method of producing polyethylene comprising (a) polymerizing ethylene in one or more reaction zones to produce a first polyethylene resin, wherein each reaction zone of the one or more reaction zones operates independently at a first value for a plurality of parameters, and wherein each parameter of the plurality of parameters is selected from the group consisting of ethylene concentration, comonomer concentration, hydrogen to ethylene ratio, temperature, catalyst concentration, cocatalyst concentration, pressure, and residence time, (b) determining a dynamic viscosity ($\eta_s^*$) of the first polyethylene resin, (c) determining a gel permeation chromatography (GPC) curve profile of the first polyethylene resin; wherein the GPC curve profile comprises a differential weight fraction (dw/d(log M)) as a function of log M, wherein M is the molecular weight of the weight fraction w, (d) comparing the dynamic viscosity of the first polyethylene resin with a target dynamic viscosity ($\eta_c^*$) and the GPC curve profile of the first polyethylene resin with a target GPC curve profile; wherein comparing the dynamic viscosity comprises calculating a dynamic viscosity deviation (% MVD) from the target dynamic viscosity; wherein comparing the GPC curve profile comprises calculating a GPC curve profile deviation (% GPCD) from the target GPC curve profile; and wherein the first polyethylene resin is characterized by a % MVD of equal to or greater than about 100%, by a % GPCD of equal to or greater than about 15%, or by both a % MVD of equal to or greater than about 100% and a % GPCD of equal to or greater than about 15%, (e) selecting a second value for one or more parameters of the plurality of parameters for at least one of the one or more reaction zones; wherein, when the first polyethylene resin is characterized by a % MVD of equal to or greater than about 100%, the second value decreases the % MVD of the polyethylene resin; wherein, when the first polyethylene resin is characterized by a % GPCD of equal to or greater than about 15%, the second value decreases the % GPCD of the polyethylene resin; and wherein, when the first polyethylene resin is characterized by both a % MVD of equal to or greater than about 100% and a % GPCD of equal to or greater than about 15%, the second value decreases both the % MVD and the % GPCD of the polyethylene resin, (f) operating the at least one of the one or more reaction zones independently at the second value of the one or more parameters of the plurality of parameters, and (g) recovering a second polyethylene resin from the one or more reaction zones, wherein the second polyethylene resin is characterized by both a % MVD of less than about 100% and a % GPCD of less than about 15%. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a system for producing polyethylene comprising one or more polymerization reaction zones configured to produce a polyethylene resin, wherein each reaction zone of the one or more reaction zones operates independently at a plurality of parameters, and wherein each parameter of the plurality of parameters is selected from the group consisting of ethylene concentration, comonomer concentration, hydrogen to ethylene ratio, temperature, catalyst concentration, cocatalyst concentration, pressure, and residence time, a testing system configured to characterize the polyethylene resin for one or more resin properties, wherein the one or more resin properties comprises at least one of dynamic viscosity, gel permeation chromatography (GPC) curve profile, weight average molecular weight ($M_w$), or combinations thereof, and a control system configured to receive the one or more resin properties from the testing system, wherein the control system comprises at least one processor and at least one controller; wherein the at least one processor compares the one or more resin properties with corresponding target properties; wherein the at least one processor, when at least one of the one or more resin properties is different when compared to the corresponding target property, signals the at least one controller; and wherein the at least one controller adjusts at least one of the plurality of parameters independently for at least one reaction zone of the one or more reaction zones. One or more aspects of the system described in this paragraph can be implemented with one or more computers such as shown in FIG. 2, for example via a processor executing software code stored in memory that implements one or more aspects or steps of the methods disclosed herein.

Further disclosed herein is a method of processing polyethylene comprising (a) providing a plurality of polyethylene resins, (b) determining a dynamic viscosity ($\eta_s^*$) of each of the plurality of polyethylene resins, (c) comparing the dynamic viscosity of each of the plurality of polyethylene resins with a target dynamic viscosity ($\eta_c^*$), wherein comparing the dynamic viscosity comprises calculating a dynamic viscosity deviation (% MVD) from the target dynamic viscosity, (d) selecting one or more polyethylene resins from the plurality of polyethylene resins to yield selected polyethylene, wherein the selected polyethylene is characterized by a % MVD of less than about 100%, and (e) processing the selected polyethylene via a shaping process to produced shaped polyethylene. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a method of processing polyethylene comprising (a) providing a plurality of polyethylene resins, (b) determining a gel permeation chromatography (GPC) curve profile of each of the plurality of polyethylene resins; wherein the GPC curve profile comprises a differential weight fraction (dw/d(log M)) as a function of log M, wherein M is the molecular weight of the weight fraction w, (c) comparing the GPC curve profile of each of the plurality of polyethylene resins with a target GPC curve profile, wherein comparing the GPC curve profile comprises calculating a GPC curve profile deviation (% GPCD) from the target GPC curve profile, (d) selecting one or more polyethylene resins from the plurality of polyethylene resins to yield selected polyethylene, wherein the selected polyethylene is characterized by a % GPCD of less than about 15%, and (e) processing the selected polyethylene via a shaping process to produced shaped polyethylene. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a method of processing polyethylene comprising (a) providing a plurality of polyethylene resins, (b) determining a dynamic viscosity ($\eta_s^*$) of each of the plurality of polyethylene resins, (c) determining a gel permeation chromatography (GPC) curve profile of each of the plurality of polyethylene resins; wherein the GPC curve profile comprises a differential weight fraction (dw/d(log M)) as a function of log M, wherein M is the molecular weight of the weight fraction w, (d) comparing the dynamic viscosity of each of the plurality of polyethylene resins with a target dynamic viscosity ($\eta_c^*$) and the GPC curve profile of each of the plurality of polyethylene resins with a target GPC curve profile; wherein comparing the dynamic viscosity comprises calculating a dynamic viscosity deviation (% MVD) from the target dynamic viscosity; and wherein comparing the GPC curve profile comprises calculating a GPC curve profile deviation (% GPCD) from the target GPC curve profile, (e) selecting one or more polyethylene resins from the plurality of polyethylene resins to yield selected polyethylene, wherein the selected polyethylene is characterized by a % MVD of less than about 100% and a % GPCD of less than about 15%, and (f) processing the selected polyethylene via a shaping process to produced shaped polyethylene. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a system for processing polyethylene comprising a testing system configured to characterize a plurality of polyethylene resins for one or more resin properties, wherein the one or more resin properties comprises at least one of dynamic viscosity, gel permeation chromatography (GPC) curve profile, weight average molecular weight ($M_w$), or combinations thereof, a computer system configured to receive the one or more resin properties from the testing system, wherein the computer system comprises at least one processor; wherein the at least one processor compares the one or more resin properties with corresponding target properties; wherein the at least one processor, when at least one of the one or more resin properties is different when compared to the corresponding target property, designates the resin as low quality resin; wherein the at least one processor, when the one or more resin properties are the same when compared to the corresponding target properties, designates the resin as selected polyethylene, and a shaping system configured to receive the selected polyethylene and process the selected polyethylene into a shaped article. One or more aspects of the system described in this paragraph can be implemented with one or more computers such as shown in FIG. 2, for example via a processor executing software code stored in memory that implements one or more aspects or steps of the methods disclosed herein.

Further disclosed herein is a method of monitoring multimodal polyethylene quality comprising (a) providing a plurality of multimodal polyethylene resins, (b) determining a dynamic viscosity ($\eta_s^*$) of each of the plurality of multimodal polyethylene resins, (c) comparing the dynamic viscosity of each of the plurality of multimodal polyethylene resins with a target dynamic viscosity ($\eta_c^*$), wherein comparing the dynamic viscosity comprises calculating a dynamic viscosity deviation (% MVD) from the target dynamic viscosity, (d) selecting one or more multimodal polyethylene resins from the plurality of multimodal polyethylene resins to yield a first multimodal polyethylene resin, wherein the first multimodal polyethylene resin is characterized by a % MVD of equal to or greater than about 100%, and wherein the first multimodal polyethylene resin is designated as a low quality resin, (e) selecting one or more multimodal polyethylene resins from the plurality of multimodal polyethylene resins to yield a second multimodal polyethylene resin, wherein the second multimodal polyethylene resin is characterized by a % MVD of less than about 100%, and wherein the second multimodal polyethylene resin is designated as a high quality resin, and (f) physically segregating the first multimodal polyethylene resin from the second multimodal polyethylene resin for further storage or processing. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a method of monitoring multimodal polyethylene quality comprising (a) providing a plurality of multimodal polyethylene resins, (b) determining a gel permeation chromatography (GPC) curve profile of each of the plurality of polyethylene resins; wherein the GPC curve profile comprises a differential weight fraction (dw/d(log M)) as a function of log M, wherein M is the molecular weight of the weight fraction w, (c) comparing the GPC curve profile of each of the plurality of polyethylene resins with a target GPC curve profile, wherein comparing the GPC curve profile comprises calculating a GPC curve profile deviation (% GPCD) from the target GPC curve profile, (d) selecting one or more multimodal polyethylene resins from the plurality of multimodal polyethylene resins to yield a first multimodal polyethylene resin, wherein the first multimodal polyethylene resin is characterized by a % GPCD of equal to or greater than about 15%, and wherein the first multimodal polyethylene resin is designated as a low quality resin, (e) selecting one or more multimodal polyethylene resins from the plurality of multimodal polyethylene resins to yield a second multimodal polyethylene resin, wherein the second multimodal polyethylene resin is characterized by a % GPCD of less than about 15%, and wherein the second multimodal polyethylene resin is designated as a high quality resin, and (f) physically segregating the first multimodal polyethylene resin from the second multimodal polyethylene resin for further storage or processing. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a method of monitoring multimodal polyethylene quality comprising (a) providing a plurality of multimodal polyethylene resins, (b) determining a dynamic viscosity ($\eta_s^*$) of each of the plurality of multimodal polyethylene resins, (c) determining a gel permeation chromatography (GPC) curve profile of each of the plurality of polyethylene resins; wherein the GPC curve profile comprises a differential weight fraction (dw/d(log M)) as a function of log M, wherein M is the molecular weight of the weight fraction w, (d) comparing the dynamic viscosity of each of the plurality of multimodal polyethylene resins with a target dynamic viscosity ($\eta_c^*$) and the GPC curve profile of each of the plurality of polyethylene resins with a target GPC curve profile, wherein comparing the dynamic viscosity comprises calculating a dynamic viscosity deviation (% MVD) from the target dynamic viscosity, and wherein comparing the GPC curve profile comprises calculating a GPC curve profile deviation (% GPCD) from the target GPC curve profile, (e) selecting one or more multimodal polyethylene resins from the plurality of multimodal polyethylene resins to yield a first multimodal polyethylene resin; wherein the first multimodal polyethylene resin is characterized by a % MVD of equal to or greater than about 100%, a % GPCD of equal to or greater than about 15%, or both a % MVD of equal to or greater than about 100% and a % GPCD of equal to or greater than about 15%; and wherein the first multimodal polyethylene resin is designated as a low quality resin, (f) selecting one or more multimodal polyethylene resins from the plurality of multimodal polyethylene resins to yield a second multimodal polyethylene resin, wherein the second multimodal polyethylene resin is characterized by both a % MVD of less than about 100% and a % GPCD of less than about 15%, and wherein the second multimodal polyethylene resin is designated as a high quality resin, and (g) physically segregating the first multimodal polyethylene resin from the second multimodal polyethylene resin for further storage or processing. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a system for monitoring multimodal polyethylene quality comprising a testing system configured to characterize a plurality of multimodal polyethylene resins for one or more resin properties, wherein the one or more resin properties comprises at least one of dynamic viscosity, gel permeation chromatography (GPC) curve profile, weight average molecular weight ($M_w$), or combinations thereof, a computer system configured to receive the one or more resin properties from the testing system, wherein the computer system comprises at least one processor; wherein the at least one processor compares the one or more resin properties with corresponding target properties; wherein the at least one processor, when at least one of the one or more resin properties is different when compared to the corresponding target property, designates the resin as low quality resin; wherein the at least one processor, when the one or more resin properties are the same when compared to the corresponding target properties, designates the resin as high quality resin, and a sorting system configured to receive quality resin designations from the computer system, wherein the sorting system physically segregates the low quality resin from the high quality resin for further storage or processing. One or more aspects of the system described in this paragraph can be implemented with one or more computers such as shown in FIG. 2, for example via a processor executing software code stored in memory that implements one or more aspects or steps of the methods disclosed herein.

Further disclosed herein is a method of monitoring multimodal polyethylene quality comprising (a) providing a plurality of multimodal polyethylene resins, (b) determining a melt index of each of the plurality of multimodal polyethylene resins, wherein resins excluding a resin having a melt index within 30% of a target melt index are designated as low quality resins, (c) determining a density of each of the plurality of multimodal polyethylene resins having a melt index within 30% of the target melt index, wherein resins excluding a resin having a density within 2.5% of a target density are designated as low quality resins, (d) determining a dynamic viscosity ($\eta_s^*$) of each of the plurality of multimodal polyethylene resins having a density within 2.5% of the target density, (e) comparing the dynamic viscosity of the multimodal polyethylene resins with a target dynamic viscosity ($\eta_c^*$); wherein comparing the dynamic viscosity comprises calculating a dynamic viscosity deviation (% MVD) from the target dynamic viscosity; and wherein resins having a % MVD of equal to or greater than about 100% are designated as low quality resins, (f) determining a weight average molecular weight ($M_w$) of each of the plurality of multimodal polyethylene resins having a % MVD of less than about 100%, wherein $M_w$ is determined from a gel permeation chromatography (GPC) curve profile, wherein the GPC curve profile comprises a differential weight fraction (dw/d(log M)) as a function of log M, and wherein M is the molecular weight of the weight fraction w, (g) comparing the $M_w$ of the multimodal polyethylene resin with a target $M_w$, wherein comparing the $M_w$ comprises calculating a $M_w$ deviation (% $M_wD$) from the target $M_w$; and wherein resins having a % $M_wD$ of equal to or greater than about 20% are designated as low quality resins, (h) comparing the GPC curve profile of each of the plurality of multimodal polyethylene resins having a % $M_wD$ of less than about 20% with a target GPC curve profile; wherein comparing the GPC curve profile comprises calculating a GPC curve profile deviation (% GPCD) from the target GPC curve profile; wherein resins having a % GPCD of equal to or greater than about 15% are designated as low quality resins; and wherein resins having a % GPCD of less than about 15% are designated as high quality resins, and (i) physically segregating the high quality resins from the low quality resins for further storage or processing. One or more aspects or steps of the method described in this paragraph can be implemented with one or more computers such as shown in FIG. 2, for example via a processor executing software code stored in memory that implements one or more aspects or steps of the methods disclosed herein.

Further disclosed herein is a method of determining multimodal polyethylene quality comprising (a) providing a multimodal polyethylene resin sample, (b) determining, in any sequence, at least one of the following that the multimodal polyethylene resin sample has a melt index within 30% of a target melt index, that the multimodal polyethylene resin sample has a density within 2.5% of a target density, that the multimodal polyethylene resin sample has a dynamic viscosity deviation (% MVD) from a target dynamic viscosity of less than about 100%, that the multimodal polyethylene resin sample has a weight average molecular weight ($M_w$) deviation (% $M_wD$) from a target $M_w$ of less than about 20%, and that the multimodal polyethylene resin sample has a gel permeation chromatography (GPC) curve profile deviation (% GPCD) from a target GPC curve profile of less than about 15%, and (c) responsive to step (b), designating the multimodal polyethylene resin sample as a high quality resin. One or more aspects or steps of the method described in this paragraph can be implemented with one or more computers such as shown in FIG. 2, for example via a processor executing software code stored in memory that implements one or more aspects or steps of the methods disclosed herein.

BRIEF DESCRIPTION OF THE DRAWINGS

For a detailed description of the disclosed processes and systems, reference will now be made to the accompanying drawings in which.

DETAILED DESCRIPTION

Figure 1:
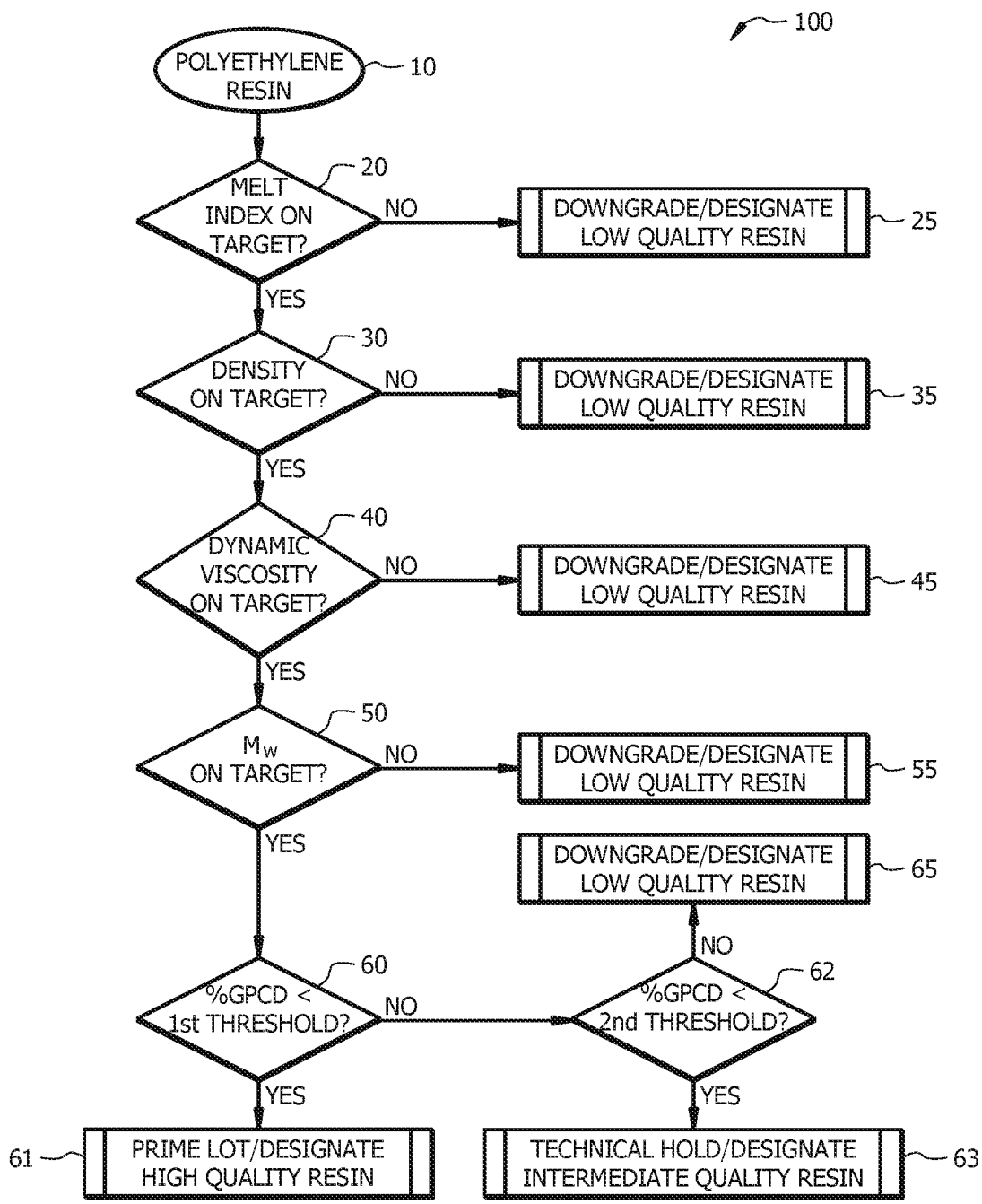
FIG. 1 illustrates a flow diagram of a process for monitoring polyethylene resin quality.

It should be understood at the outset that although an illustrative implementation of one or more embodiments are provided below, the disclosed systems, methods, or both can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are systems, and processes related to petrochemical production processes, for example the production of polyethylene. The systems, and processes are generally related to the production of multimodal resins, for example bimodal polyethylene, as well as monitoring the quality of produced resins, and forming the resins into end-use products.

As disclosed herein, a method of producing polyethylene can comprise (a) polymerizing ethylene in one or more reaction zones to produce a first polyethylene resin, wherein each reaction zone of the one or more reaction zones operates independently at a first value for a plurality of parameters, and wherein each parameter of the plurality of parameters is selected from the group consisting of ethylene concentration, comonomer concentration, hydrogen to ethylene monomer ratio ($H_2$/MON), temperature, catalyst concentration, cocatalyst concentration, pressure, and residence time; (b) determining a dynamic viscosity ($\eta_s^*$) of the first polyethylene resin across a range of shear rate ($\omega_i$) of from about 0.01 s$^{-1}$ to about 1,000 s$^{-1}$; (c) determining a gel permeation chromatography (GPC) curve profile of the first polyethylene resin; wherein the GPC curve profile comprises a differential weight fraction (dw/d(log M)) as a function of log M, wherein M is the molecular weight of the weight fraction w; (d) comparing the dynamic viscosity of the first polyethylene resin with a target dynamic viscosity ($\eta_c^*$) and the GPC curve profile of the first polyethylene resin with a target GPC curve profile; wherein comparing the dynamic viscosity comprises calculating a dynamic viscosity deviation (% MVD) from the target dynamic viscosity; wherein comparing the GPC curve profile comprises calculating a GPC curve profile deviation (% GPCD) from the target GPC curve profile; and wherein the first polyethylene resin is characterized by a % MVD of equal to or greater than about 100%, by a % GPCD of equal to or greater than about 15%, or by both a % MVD of equal to or greater than about 100% and a % GPCD of equal to or greater than about 15%; (e) selecting a second value for one or more parameters of the plurality of parameters for at least one of the one or more reaction zones; wherein, when the first polyethylene resin is characterized by a % MVD of equal to or greater than about 100%, the second value decreases the % MVD of the polyethylene resin; wherein, when the first polyethylene resin is characterized by a % GPCD of equal to or greater than about 15%, the second value decreases the % GPCD of the polyethylene resin; and wherein, when the first polyethylene resin is characterized by both a % MVD of equal to or greater than about 100% and a % GPCD of equal to or greater than about 15%, the second value decreases both the % MVD and the % GPCD of the polyethylene resin; (f) operating the at least one of the one or more reaction zones independently at the second value of the one or more parameters of the plurality of parameters; and (g) recovering a second polyethylene resin from the one or more reaction zones, wherein the second polyethylene resin is characterized by both a % MVD of less than about 100% and a % GPCD of less than about 15%. In an aspect, the first polyethylene resin can be characterized by a melt index that is within 30% of a target melt index; wherein the second polyethylene resin can be characterized by a melt index that is within 30% of the target melt index; wherein the first polyethylene resin is characterized by a density that is within 2.5% of a target density; and wherein the second polyethylene resin is characterized by a density that is within 2.5% of the target density. In some aspects, the second polyethylene resin can be further processed via a shaping process into shaped polyethylene. The polyethylene resin can be a multimodal resin, e.g., a bimodal resin.

In an aspect, a method of determining multimodal polyethylene quality can comprise (a) providing a multimodal polyethylene resin sample; (b) determining, in any sequence, the following: that the multimodal polyethylene resin sample has a melt index within 30% of a target melt index; that the multimodal polyethylene resin sample has a density within 2.5% of a target density; that the multimodal polyethylene resin sample has a % MVD from a target dynamic viscosity of less than about 100%; that the multimodal polyethylene resin sample has a weight average molecular weight ($M_w$) deviation (% $M_wD$) from a target $M_w$ of less than about 20%; and that the multimodal polyethylene resin sample has a % GPCD from a target GPC curve profile of less than about 15%; and (c) responsive to step (b), designating the multimodal polyethylene resin sample as a high quality resin. In such aspect, the method can further comprise physically segregating the high quality resin from a low quality resin for further storage or processing; wherein the low quality resin excludes a resin having at least one property selected from the group consisting of a melt index within 30% of the target melt index, a density within 2.5% of the target density, a % MVD of less than about 100%, a % $M_wD$ of less than about 20%, a % GPCD of less than about 15%, and combinations thereof.

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further, certain features of the present invention which are, for clarity, described herein in the context of separate embodiments, may also be provided in combination in a single embodiment. Conversely, various features of the invention that are, for brevity, described in the context of a single embodiment, may also be provided separately or in any sub-combination.

If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claim. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst system consisting of specific components; alternatively, consisting essentially of specific components; or alternatively, comprising the specific components and other non-recited components.

In this disclosure, while systems, processes, and methods are often described in terms of "comprising" various components, devices, or steps, the systems, processes, and methods can also "consist essentially of" or "consist of" the various components, devices, or steps, unless stated otherwise.

The term "about" as used herein means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

Although any methods, devices, and materials similar or equivalent to those described herein can be used in the practice or testing of the invention, the typical methods, devices, and materials are herein described.

In an aspect, polymerizing an olefin (e.g., polymerizing ethylene) can comprise contacting an olefin monomer (e.g., ethylene) with a catalyst system within a reaction zone (e.g., polymerization reaction zone) or reactor to form a polyolefin (e.g., polyethylene). Catalyst systems can include any suitable catalyst system(s) (e.g., catalyst, co-catalyst, support, activator) useful for polymerizing olefin monomers, such as chromium based catalyst systems, single site transition metal catalyst systems (including metallocene catalyst systems), Ziegler-Natta catalyst systems, and the like, or combinations thereof. As will be appreciated by one of skill in the art, and with the help of this disclosure, catalysts may be activated for subsequent polymerization and may or may not be associated with a support material, for example. Further, and as will be appreciated by one of skill in the art, and with the help of this disclosure, polymerization conditions (e.g., equipment, process conditions, reactants, additives and any other materials used in polymerization processes) will vary in a given process, depending on the desired composition and properties of the polymer being formed. Furthermore, and as will be appreciated by one of skill in the art, and with the help of this disclosure, each reactor can have 1, 2, 3, 4, 5, or more reaction zones.

For purposes of the disclosure herein, the term "polymerization reactor" can include any reactor capable of polymerizing olefin monomers (e.g., ethylene) and optionally comonomers (one or more than one comonomers) to produce polyolefin polymers (polyolefins), such as homopolymers, copolymers, terpolymers, and the like. Polyolefins produced in the polymerization reactor can be referred to as resins or polymers.

The polymerization reactor can comprise one or more reaction zones (e.g., polymerization reaction zones), wherein each of the reaction zones can be individually characterized by process operating parameters, such as reactant concentrations (e.g., monomer concentration, comonomer concentration, hydrogen concentration), catalyst system concentration (e.g., catalyst concentration, cocatalyst concentration), temperature, pressure, residence time, and the like. The desired polymerization conditions in one of the reaction zones can be the same as or different from the operating conditions of any other reaction zones involved in the overall process of producing the polymers of the present disclosure.

The various types of reactors include those that can be referred to as a batch reactor, slurry reactor, gas-phase reactor, solution reactor, high pressure reactor, tubular reactor, autoclave reactor, and the like, or combinations thereof. Suitable process conditions (e.g., polymerization conditions) are used for the various reactor types. Gas phase reactors can comprise fluidized bed reactors or staged horizontal reactors. Slurry reactors can comprise vertical or horizontal loops. High pressure reactors can comprise autoclave or tubular reactors. Reactor types can include batch or continuous processes. Continuous processes can use intermittent or continuous product discharge or transfer. Processes can also include partial or full direct recycle of unreacted monomer, unreacted comonomer, catalyst, co-catalyst, diluents, or combinations thereof.

In an aspect, polymerization reactor systems suitable for use in the present disclosure can comprise one type of reactor in a system or multiple reactors of the same or different type (e.g., a single reactor, dual reactor, more than two reactors), operated in any suitable configuration. Production of polymers in multiple reactors can include several stages in at least two separate polymerization reactors interconnected by a transfer system making it possible to transfer the polymers resulting from a first polymerization reactor into a second reactor. The desired polymerization conditions in one of the reactors can be the same as or different from the operating conditions of any other reactors involved in the overall process of producing the polymers of the present disclosure. Alternatively, polymerization in multiple reactors can include the transfer, either manual or automatic, of polymer from one reactor to subsequent reactor or reactors for additional polymerization.

Multiple reactor systems can include any combination including, but not limited to, multiple loop reactors, multiple gas phase reactors, a combination of loop and gas phase reactors, multiple high pressure reactors, or a combination of high pressure with loop reactors, gas phase reactors, or both loop and gas phase reactors. The multiple reactors can be operated in series, in parallel, or both in series and in parallel.

In an aspect, polymerizing ethylene as disclosed herein can comprise polymerizing ethylene in polymerization reactor systems comprising a single reactor, comprising two reactors, and comprising more than two reactors. The polymerization reactor system can comprise a slurry reactor, a gas-phase reactor, a solution reactor, as well as multi-reactor combinations thereof. In an aspect, any suitable reactor configuration can be employed to produce the polymer of the present disclosure.

In an aspect, a polymerization reactor system can comprise a fast fluidization reaction zone, a plug flow reaction zone, or both a fast fluidization reaction zone and a plug flow reaction zone. In such aspect, a first reaction zone (e.g., a riser) can comprise a fast fluidization reaction zone, wherein fast fluidization conditions can be established by feeding a gas mixture comprising one or more olefins (e.g., ethylene and comonomer) at a velocity higher than a transport velocity of polymer particles. Generally, fast fluidization conditions refer to a velocity of a gas mixture of from about 0.5 meters per second (m/s) to about 15 m/s, or alternatively from about 0.8 m/s to about 5 m/s. In such aspect, a second reaction zone (e.g., downcomer) can comprise a plug flow reaction zone, wherein polymer particles can flow under the action of gravity in a more dense form (e.g., mass of polymer per volume of reactor is greater in the downcomer than in the riser), such that high values of density of the solid polymer particles are reached (e.g., mass of polymer per volume of reactor). Such high density values can approach the bulk density of the produced polymer. The polymer can flow vertically down through the downcomer in a "plug flow" (e.g., packed flow mode), such that only small quantities of gas are entrained between the polymer particles. Generally, a plug flow reactor or reaction zone (PFR), also known as a flow tube reactor or reaction zone, comprises a fluid flowing through the reactor or reaction zone as a series of infinitely thin coherent "plugs," each plug having a uniform composition, traveling in the axial direction of the flow tube reactor or reaction zone. In PFRs, it is assumed that as a plug flows through the reactor or reaction zone, the fluid is perfectly mixed in the radial direction, but not in the axial direction (forwards or backwards). In some aspects, a single reactor can comprise both the fast fluidization reaction zone and the plug flow reaction zone. In other aspects, a first reactor can comprise the fast fluidization reaction zone, and a second reactor can comprise the plug flow reaction zone. Fast fluidization reaction zones and plug flow reaction zones are described in more detail in U.S. Pat. No. 9,023,945; which is incorporated by reference herein in its entirety.

According to one aspect of this disclosure, the polymerization reactor system can comprise at least one loop slurry reactor comprising vertical or horizontal loops. Monomer, diluent, catalyst, and optionally any comonomer can be continuously fed to a loop reactor where polymerization occurs. Generally, continuous processes can comprise the continuous introduction of a monomer, an optional comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer, comonomer, or combinations thereof. Various technologies can be used for this separation step including but not limited to, flashing that can include any combination of heat addition and pressure reduction; separation by cyclonic action in either a cyclone or hydrocyclone; or separation by centrifugation.

A suitable slurry polymerization process (also known as the particle form process), is disclosed, for example, in U.S. Pat. Nos. 3,248,179; 4,501,885; 5,565,175; 5,575,979; 6,239,235; 6,262,191; and 6,833,415; each of which is incorporated by reference herein in its entirety.

Suitable diluents used in slurry polymerization include, but are not limited to, the monomer, and optionally, the comonomer, being polymerized and hydrocarbons that are liquids under polymerization reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used.

According to another aspect of this disclosure, the polymerization reactor system can comprise at least one gas phase reactor. Such polymerization reactor systems can employ a continuous recycle stream containing one or more monomers continuously cycled through a fluidized bed in the presence of a catalyst under polymerization conditions. A recycle stream can be withdrawn from the fluidized bed and recycled back into the reactor. Simultaneously, a polymer product can be withdrawn from the reactor and new or fresh monomer can be added to replace the polymerized monomer. Likewise, copolymer product can optionally be withdrawn from the reactor and new or fresh comonomer can be added to replace polymerized comonomer, polymerized monomer, or combinations thereof. Such gas phase reactors can comprise a process for multi-step gas phase polymerization of olefins, in which olefins are polymerized in the gaseous phase in at least two independent gas phase polymerization zones (e.g., reaction zones) while feeding a catalyst-containing polymer formed in a first polymerization zone to a second polymerization zone. Gas phase reactors are disclosed in U.S. Pat. Nos. 5,352,749; 4,588,790; and 5,436,304; each of which is incorporated by reference herein in its entirety.

According to yet another aspect of this disclosure, a high-pressure polymerization reactor can comprise a tubular reactor or an autoclave reactor. Tubular reactors, autoclave reactors, or both can have several zones where fresh monomer (optionally, comonomer), or a polymerization catalyst system can be added. Monomer (optionally, comonomer) can be entrained in an inert dense fluid stream (well above the critical point at such high pressures) and introduced into the reactor (typically introduced in multiple locations on the reactor). Polymerization catalyst system components can be entrained in a monomer feed stream, introduced as liquids or supercritical fluids directly into the reactor, or both. The fluid streams can be intermixed in the reactor to initiate and sustain polymerization. Heat and pressure can be employed appropriately to obtain optimal polymerization reaction conditions.

According to still yet another aspect of this disclosure, the polymerization reactor system can comprise a solution polymerization reactor wherein the monomer (optionally, comonomer) can be contacted with a catalyst composition by suitable stirring or other means. A carrier comprising an inert organic diluent or excess monomer (optionally, comonomer) can be employed. If desired, the monomer, optional comonomer, or both can be brought in the vapor phase into contact with a catalytic reaction product, in the presence or absence of liquid material. A polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactor systems suitable for the disclosed systems and processes can further comprise any combination of at least one raw material feed system, at least one feed system for catalyst or catalyst components, and at least one polymer recovery system. Suitable reactor systems can further comprise systems for feedstock purification, catalyst storage and preparation, extrusion, reactor cooling, polymer recovery, fractionation, recycle, storage, loadout, laboratory analysis, and process control.

Conditions (e.g., polymerization conditions) that are controlled for polymerization efficiency and to provide desired resin properties include temperature; pressure; type of catalyst or co-catalyst, quantity of catalyst or co-catalyst, or both; concentrations of various reactants; partial pressures of various reactants; reactor residence time (e.g., reaction zone residence time); or combinations thereof. Various polymerization conditions can be held substantially constant, for example, for the production of a particular resin grade.

Polymerization temperature can affect catalyst productivity, polymer molecular weight and molecular weight distribution. Suitable polymerization temperature can be any temperature below the de-polymerization temperature according to the Gibbs Free energy equation. The polymerization temperature can have as upper limit a temperature at which the monomer (e.g., ethylene) begins to decompose. As will be appreciated by one of skill in the art, and with the help of this disclosure, monomer decomposition temperatures are pressure dependent. Polymerization temperatures can be from about 60° C. to about 350° C., alternatively from about 60° C. to about 280° C., or alternatively from about 60° C. to about 120° C., depending upon the type of polymerization reactor. In some aspects, polymerization temperatures can be from about 70° C. to about 100° C., or alternatively from about 75° C. to about 95° C.

Suitable pressures will also vary according to the reactor and polymerization type. The pressure for liquid phase polymerizations in a loop reactor is typically less than about 1,000 psig (6.9 MPa). Pressure for gas phase polymerization is usually at about 200 psig (1.4 MPa) to about 700 psig (4.8 MPa), or alternatively at about 200 psig (1.4 MPa) to about 500 psig (3.4 MPa). High-pressure polymerization in tubular or autoclave reactors is generally run at about 20,000 psig (138 MPa) to about 75,000 psig (517 MPa). Polymerization reactors can also be operated in a supercritical region occurring at generally higher temperatures and pressures. Operation above the critical point of a pressure/temperature diagram (supercritical phase) can offer advantages. In an aspect, polymerization can occur in an environment having a suitable combination of temperature and pressure.

In some aspects, a polymerization process as disclosed herein can comprise an olefin polymerization process conducted in the absence of added hydrogen. In such aspects, a catalyst system can be contacted with an olefin monomer and optionally an olefin comonomer in a polymerization reactor system under polymerization conditions to produce an olefin polymer, wherein the polymerization process is conducted in the absence of added hydrogen (no hydrogen is added to the polymerization reactor system). As will be appreciated by one of skill in the art, and with the help of tis disclosure, hydrogen can be generated in-situ by catalyst compositions in various olefin polymerization processes, and the amount of hydrogen generated can vary depending upon the specific catalyst components employed, the type of polymerization process used, the polymerization reaction conditions utilized, and the like.

In other aspects, a polymerization process as disclosed herein can comprise an olefin polymerization process conducted in the presence of a suitable amount of added hydrogen. In such aspects, a catalyst system can be contacted with an olefin monomer and optionally an olefin comonomer in a polymerization reactor system under polymerization conditions to produce an olefin polymer, wherein the polymerization process is conducted in the presence of added hydrogen (hydrogen is added to the polymerization reactor system). For example, the ratio of hydrogen to the olefin monomer ($H_2$/MON) in the polymerization process can be controlled, often by the feed ratio of hydrogen to the olefin monomer entering the reactor. The added hydrogen to olefin monomer ratio in the process can be controlled at a weight ratio which falls within a range of from about 25 ppm to about 1500 ppm, alternatively from about 50 to about 1000 ppm, or alternatively from about 100 ppm to about 750 ppm.

In some aspects, the feed or reactant ratio of hydrogen to olefin monomer can be maintained substantially constant during the polymerization run for producing a particular polymer grade. That is, the hydrogen:olefin monomer ratio (e.g., $H_2$/MON) can be selected at a particular ratio within a range of from about 5 ppm up to about 1000 ppm or so, and maintained at the ratio to within about +/−25% during the polymerization run. For example, if the target $H_2$/MON ratio is 100 ppm, then maintaining the $H_2$/MON ratio substantially constant would entail maintaining the feed $H_2$/MON ratio between about 75 ppm and about 125 ppm. Further, the addition of comonomer (or comonomers) can be, and generally is, substantially constant throughout the polymerization run for producing a particular polymer grade.

However, in other aspects, it is contemplated that monomer, comonomer (or comonomers), optionally hydrogen, or combinations thereof can be periodically pulsed to the reactor, for instance, in a manner similar to that employed in U.S. Pat. No. 5,739,220; and U.S. Publication No. 2004/0059070; each of which is incorporated by reference herein in its entirety.

The concentration of the reactants entering the polymerization reactor system can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

The concentrations, partial pressures, or both of monomer, comonomer, hydrogen, co-catalyst, modifiers, and electron donors are important in producing these resin properties. Comonomer can be used to control product density. Hydrogen can be used to control product molecular weight. Cocatalysts can be used to alkylate, scavenge poisons and control molecular weight. Modifiers can be used to control product properties and electron donors can affect stereoregularity, molecular weight distribution, molecular weight, or combinations thereof. In addition, the concentration of poisons should be minimized because poisons impact the reactions and product properties.

The olefin monomers suitable for use in the polymerization processes disclosed herein can comprise $C_2$ to $C_{30}$ olefin monomers, alternatively $C_2$ to $C_{20}$ olefin monomers, or alternatively $C_2$ to $C_{12}$ olefin monomers (e.g., ethylene, propylene, butene, pentene, 4-methyl-1-pentene, hexene, octene, decene, dodecene). In some aspects, the monomers can include olefinic unsaturated monomers, $C_4$ to $C_{18}$ diolefins, conjugated or nonconjugated dienes, polyenes, vinyl monomers, cyclic olefins, and the like. For example, in some aspects, the monomers can include norbornene, norbornadiene, isobutylene, isoprene, vinylbenzylcyclobutane, styrene, alkyl substituted styrene, ethylidene norbornene, dicyclopentadiene, cyclopentene, and the like.

In an aspect, the monomer comprises $C_2$ to $C_3$ olefin monomers. For example, the monomer comprises ethylene. In some aspects, the monomer comprises ethylene, wherein the produced resin comprises an ethylene homopolymer.

In other aspects, ethylene is copolymerized with a comonomer to produce a copolymer. Nonlimiting examples of comonomers suitable for use in the present disclosure include alpha olefins, such as propylene, 1-butene, 1-pentene, 1-hexene, 3-methyl-1-butene, 4-methyl-1-pentene, 1-heptene, 1-octene, 1-nonene, 1-decene, and the like, or combinations thereof. In an aspect, the comonomer comprises 1-hexene.

In an aspect, the comonomer can be introduced to the reactor (e.g., reaction zone) in an amount of from about 0.01 wt. % to about 10 wt. %, alternatively from about 0.01 wt. % to about 5 wt. %, or alternatively from about 0.1 wt. % to about 4 wt. %, based on the total weight of monomer and comonomer introduced to the reactor (e.g., reaction zone).

Any suitable polymerization catalyst system can be employed for the production of multimodal (e.g., bimodal) polyolefins as disclosed herein. A suitable polymerization catalyst system can comprise a catalyst and, optionally, a co-catalyst (e.g., an organoaluminum compound), a promoter, or both. In some aspects, the catalyst system can comprise an activator (e.g., activator-support). Nonlimiting examples of suitable catalyst systems include but are not limited to single-site or dual-site catalysts such as Ziegler Natta catalysts, Ziegler catalysts, chromium catalysts, chromium oxide catalysts, chrome-silica catalysts, chrome-titania catalysts, chromocene catalysts, metallocene catalysts, nickel catalysts, or combinations thereof. Suitable metallocene catalysts for use in the systems described herein can be any conventional or non-conventional metallocene catalyst. As used herein, the term "metallocene" is used to refer to all catalytically active metals: η-ligand complexes in which a metal is complexed by one, two, or more open chain or closed-ring η-ligands. The use of bridged bis-η-ligand metallocenes, single η-ligand "half metallocenes", and bridged η-τ ligand "scorpionate" metallocenes is preferred in accordance with some aspects of the present disclosure. The metal in such complexes is preferably a group 4A, 5A, 6A, 7A or 8A metal or a lanthanide or actinide of the Periodic Table of the Elements, especially a group 4A, 5A or 6A metal, more particularly Zr, Hf or Ti. The η-ligand preferably comprises $\eta^4$ or $\eta^5$ open-chain or a $\eta^5$-cyclopentadienyl ring, optionally with a ring or chain carbon replaced by a heteroatom (e.g., N, B, S or P), optionally substituted by pendant or fused ring substituents and optionally linked by bridge (e.g., a 1 to 4 atom bridge such as $(CH_2)_2$, $C(CH_3)_2$ or $Si(CH_3)_2$) to a further optionally substituted homo or heterocyclic cyclopentadienyl ring. The ring substituents can, for example, be halo atoms or alkyl groups optionally with carbons replaced by heteroatoms such as O, N and Si, especially Si and O and optionally substituted by mono or polycyclic groups such as phenyl or naphthyl groups. Catalyst systems suitable for use in the present disclosure have been described, for example, in U.S. Pat. Nos. 7,163,906; 7,619,047; 7,790,820; 7,960,487; 8,138,113; 8,207,280; 8,268,944; 8,450,436; and 9,181,372; each of which is incorporated by reference herein in its entirety.

In an aspect of the present disclosure, the catalyst system can comprise an activator. The activator can be a solid oxide activator-support, a chemically treated solid oxide, a clay mineral, a pillared clay, an exfoliated clay, an exfoliated clay gelled into another oxide matrix, a layered silicate mineral, a non-layered silicate mineral, a layered aluminosilicate mineral, a non-layered aluminosilicate mineral, an aluminoxane, a supported aluminoxane, an ionizing ionic compound, an organoboron compound, or any combination thereof. The terms "chemically-treated solid oxide," "solid oxide activator-support," "acidic activator-support," "activator-support," "treated solid oxide compound," and the like are used herein to indicate a solid, inorganic oxide of relatively high porosity, which exhibits Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide compound comprises the calcined contact product of at least one solid oxide compound with at least one electron-withdrawing anion source compound. Typically, the chemically-treated solid oxide comprises at least one ionizing, acidic solid oxide compound. The terms "support" and "activator-support" are not used to imply these components are inert, and such components should not be construed as an inert component of the catalyst composition.

Catalyst systems suitable for use in the present disclosure, as well as suitable reactors and polymerization conditions are described in more detail in U.S. Pat. Nos. 8,268,944; 9,845,367; and 9,850,330; and EP No. 1756175; each of which is incorporated by reference herein in its entirety.

Monomers, such as ethylene, can be polymerized in the presence of the catalyst system (e.g., catalyst, cocatalyst). Polymerizing monomers can comprise allowing a polymerization reaction between a plurality of monomers by contacting a monomer or monomers with a catalyst system under conditions suitable for the formation of a polymer. Polymerizing comonomers can comprise allowing a polymerization reaction between a plurality of comonomers by contacting a comonomer or comonomers with a catalyst system under conditions suitable for the formation of a copolymer.

As disclosed herein, polymerizing monomers can comprise selectively manipulating one or more polymerization reaction conditions (e.g., process conditions) to yield a given polymer product, to yield a polymer product having one or more desirable properties, to achieve a desired efficiency, to achieve a desired yield, and the like, or combinations thereof. In an aspect, the method of producing polyolefins as disclosed herein can comprise adjusting one or more polymerization reaction conditions.

Polymerizing monomers can comprise maintaining a suitable temperature, pressure, partial pressure(s), or combinations thereof during the polymerization reaction; alternatively, cycling between a series of suitable temperatures, pressures, partial pressure(s), or combinations thereof during the polymerization reaction.

Polymerizing monomers can comprise introducing ethylene monomer, a comonomer, or both to one or more reaction zones. The concentration of each of the monomer and comonomer can be selectively manipulated for each individual reactor (e.g., reaction zone), to achieve a polyolefin with desired properties.

Polymerizing monomers can include introducing hydrogen into one or more of reactors (e.g., reaction zones). In some aspects, the amount of hydrogen introduced into each reaction zone can be adjusted so as to obtain, in the diluent, a molar ratio of hydrogen to ethylene (e.g., $H_2$/MON ratio) of 0.001 to 0.1. This molar ratio can be at least 0.004 in each reaction zone, and in some instances this molar ratio cannot exceed 0.05. In some aspects, the ratio of the concentration of hydrogen in the diluent in a first reaction zone to the concentration of hydrogen in a second reaction zone can be at least 20, alternatively, at least 30, alternatively, at least 40, alternatively, not greater than 300, or alternatively, not greater than 200. Suitable hydrogen concentration control methods and systems are disclosed in U.S. Pat. No. 6,225,421, which is incorporated by reference herein in its entirety.

Polymerizing monomers can comprise introducing a catalyst, a cocatalyst, or both to one or more reaction zones. The concentration of each of the catalyst and cocatalyst can be selectively manipulated for each individual reactor (e.g., reaction zone), to achieve a polyolefin with desired properties.

Polymerizing monomers can comprise circulating, flowing, cycling, mixing, agitating, or combinations thereof, the monomers (optionally, comonomers), catalyst system, reaction mixture (e.g., slurry) within one or more reaction zones, between one or more reaction zones, or combinations thereof. In aspects where the monomers (optionally, comonomers), catalyst system, reaction mixture (e.g., slurry), or combinations thereof are circulated, circulation can be at a velocity (e.g., slurry velocity) of from about 1 m/s to about 30 m/s, alternatively, from about 2 m/s to about 17 m/s, or alternatively, from about 3 m/s to about 15 m/s. As will be appreciated by one of skill in the art, and with the help of this disclosure, the circulation velocity directly correlates with the residence time in a particular reactor (e.g., reaction zone), and the residence time of each reactor (e.g., reaction zone) can be individually manipulated by adjusting the fluid velocity.

Polymerizing monomers can comprise configuring the one or more reaction zones to yield a multimodal (e.g., a bimodal) polymer (e.g., polyethylene).

In an aspect, a method of producing polyethylene as disclosed herein can comprise polymerizing an olefin monomer in one or more reaction zones (e.g., a plurality of reaction zones) under polymerization conditions to form multimodal polyolefins; for example, to form multimodal polyolefins having a desired set of characteristics. The desired set of characteristics can include any of a variety of properties, including but not limited to, density, melt index, molecular weight, molecular weight distribution, dynamic viscosity, and the like, for example.

Herein, the "modality" of a polymer resin refers to the form of its molecular weight distribution curve, i.e., the appearance of the graph of the polymer weight fraction (w) as a function of its molecular weight (M). The polymer weight fraction refers to the weight fraction of molecules of a given size. A polymer having a molecular weight distribution curve showing a single peak can be referred to as a unimodal polymer, a polymer having a curve showing two distinct peaks can be referred to as bimodal polymer, a polymer having a curve showing three distinct peaks can be referred to as trimodal polymer, etc. A polymeric composition including a plurality of molecular weight peaks (e.g., 2 or more molecular weight peaks) is considered to be a multimodal polyolefin (e.g., bimodal polyolefin, trimodal polyolefin, and the like).

Multimodal polyolefins can be produced via a variety of processes. In some aspects, multimodal polyolefins can be produced via polymerization processes utilizing multimodal catalyst systems (i.e., catalyst systems including at least two different catalytically active metal components), for example in a single reaction zone, although more than one reaction zone can be used. Alternatively, multimodal polyolefins can be produced by employing at least two reaction zones, wherein each reaction zone can independently have its own set of polymerization conditions. Such reaction zones can be connected in series, wherein a transfer effluent from a reaction zone (e.g., a first reaction zone) can be transferred to a subsequent reaction zone (e.g., a second reaction zone), and so forth, until the multimodal polyolefin product is discharged from a final reaction zone with the desired set of characteristics.

In an aspect, method of producing polyethylene as disclosed herein can comprise forming bimodal polyolefins. As used herein, the term "bimodal polyolefin" refers to a single polyolefin composition including at least one identifiable high molecular weight (HMW) fraction and at least one identifiable low molecular weight (LMW) fraction, for example two distinct peaks on a molecular weight distribution curve. In such aspect, the bimodal polyolefins can be produced by employing a first reaction zone connected in series to a second reaction zone, so that the transfer effluent withdrawn from the first reaction zone (which generally includes a first polyolefin and unreacted olefin monomer) can be introduced into the second reaction zone; and a polymerization product formed in the second reaction zone is withdrawn therefrom and includes the bimodal polyolefin. In the preparation of bimodal polyolefins, the HMW fraction and the LMW fraction can be prepared in any suitable order in the reaction zones, e.g., the LMW fraction can be formed in a first reaction zone and the HMW fraction in a second reaction zone, or vice versa, for example. The individual components of the multimodal polyolefin (e.g., bimodal polyolefin) can be obtained by deconvoluting a gel permeation chromatography (GPC) curve profile of the copolymer as described in U.S. Publication No. 20070298508 A1, which is incorporated by reference herein in its entirety.

In some aspects, the bimodal resin can have a HMW component and a LMW component; wherein the BMW component is present in an amount of from about 30 wt. % to about 70 wt. %, alternatively from about 35 wt. % to about 65 wt. %, alternatively from about 40 wt. % to about 60 wt. %, or alternatively from about 45 wt. % to about 55 wt. %; and wherein the LMW component is present in an amount of from about 70 wt. % to about 30 wt. %, alternatively from about 65 wt. % to about 35 wt. %, alternatively from about 60 wt. % to about 40 wt. %, or alternatively from about 55 wt. % to about 45 wt. %.

In some aspects, a comonomer (that is different from the olefin monomer) can also be introduced into the second reaction zone. For example, the comonomer can be a $C_4$-$C_8$ olefin monomer. In an aspect, the comonomer can comprise butene, hexene (e.g., 1-hexene), or both. In an aspect, the comonomer comprises 1-hexene.

The first reaction zone can generally be operated under first polymerization conditions, while the second reaction zone can generally be operated under second polymerization conditions. The first polymerization conditions and the second polymerization conditions can be adapted to form polyolefins having a desired set of characteristics. As such, the first polymerization conditions and the second polymerization conditions can vary from one another. However, it is contemplated that in certain circumstances the first and second polymerization conditions can be similar, if not the same. For example, in one or more aspects, the same catalyst system can be utilized in the plurality of reaction zones. However, in other aspects, different catalyst systems can be used in the plurality of reaction zones.

In some aspects, the polymerization process comprises polymer product separation. The separation can occur at any point within the process. For example, separation can occur after withdrawing the polymerization product from the second reaction zone, to recover a polyethylene resin. Alternatively, the process can include separating a first reaction zone product, either within the transfer effluent or another stream withdrawn from the first reaction zone. Such separation can be accomplished by methods known in the art and can include, without limitation, concentration devices, such as hydrocyclones, flashing devices, or combinations thereof, for example. The transfer effluent or a portion thereof can be introduced to the second reaction zone with or without separation of its components.

In an aspect, polyethylene resins (e.g., multimodal resins, such as bimodal resins) as disclosed herein can be characterized by target property values, such as target melt index, target density, target molecular weight, target viscosity, target molecular weight distribution profile, and the like, or combinations thereof. In aspects where the polyethylene resins as disclosed herein meet the target property values, the resins can be designated as "high quality" resins. High quality resins can also be referred to as "on-spec" resins or "prime lot" resins or "prime" resins. In aspects where the polyethylene resins as disclosed herein do not meet at least one of the target property values, the resins can be designated as "low quality" resins; and one or more process operating parameters can be adjusted such that the process produces high quality resins (as opposed to low quality resins). Low quality resins can also be referred to as "off-spec" resins. In aspects where the polyethylene resins as disclosed herein do not meet at least one of the target property values and where more than one reaction zone is used for producing the polyethylene resins as disclosed herein, one or more process operating parameters can be adjusted independently in at least one of the reaction zones, such that the process produces high quality resins.

For purposes of the disclosure herein, the term "target property" (e.g., target melt index, target density, target molecular weight, target viscosity, target molecular weight distribution profile, and the like, or combinations thereof) refers to the property of a final product resin (as opposed to an intermediate resin product, e.g., an intermediate resin product transferred from one reactor or reaction zone to another reactor or reaction zone). As will be appreciated by one of skill in the art, and with the help of this disclosure, although intermediate resin products could be produced in polyolefin production systems employing two or more reactors in series (e.g., an intermediate resin product recovered from a first reactor and introduced to a second reactor), the target property characterizes the final product recovered from the polyolefin production system, e.g., a final polyolefin (e.g., polyethylene) resin product after all polymerization reactions have been concluded.

While the present disclosure will be discussed in detail in the context of the target property characterizing a final product of a polyolefin production system, it should be understood that the methods disclosed herein or any steps thereof can be applied to any suitable resin products (e.g., intermediate resin products, final resin products) in any suitable petrochemical production process requiring characterization of a resin product with respect to its properties. The resin products can comprise any suitable resin products compatible with the disclosed methods and materials.

In an aspect, a method of producing polyethylene resins as disclosed herein can comprise the steps of (a) polymerizing ethylene in one or more reaction zones to produce a first polyethylene resin, wherein each reaction zone of the one or more reaction zones operates independently at a first value for a plurality of parameters, and wherein each parameter of the plurality of parameters is selected from the group consisting of ethylene concentration, comonomer concentration, hydrogen to olefin monomer ratio ($H_2$/MON), temperature, catalyst concentration, cocatalyst concentration, pressure, and residence time; (b) determining one or more properties for the first polyethylene resin; (c) comparing the one of more properties of the first polyethylene resin with corresponding target properties; (d) when at least one of the properties of the first polyethylene resin is different from the corresponding target property, selecting a second value for one or more parameters of the plurality of parameters for at least one of the one or more reaction zones, wherein the second value provides for the property of the resin that was different from the corresponding target property to become the same as or at least approach (e.g., get closer to) the target property; (e) operating the at least one of the one or more reaction zones independently at the second value of the one or more parameters of the plurality of parameters; and (f) recovering a second polyethylene resin from the one or more reaction zones, wherein the second polyethylene resin is characterized by the one or more properties being the same as the corresponding target properties. In such aspect, the method can further comprise repeating steps (b) through (e) until the produced polyethylene resin (e.g., second polyethylene resin) is characterized by the one or more properties being the same as the corresponding target properties.

In an aspect, a method of producing polyethylene resins as disclosed herein can comprise determining a melt index for the polyethylene resin (e.g., first polyethylene resin, second polyethylene resin). The method can further comprise comparing the melt index of the polyethylene resin with a target melt index. The melt index refers to the amount of a polymer which can be forced through a melt indexer orifice of 0.0825 inch diameter when subjected to the indicated force in ten minutes at 190° C., as determined in accordance with ASTM D1238.

In an aspect, the polyethylene resin (e.g., first polyethylene resin, second polyethylene resin) can be characterized by a melt index that is the same as the target melt index, e.g., a melt index that is within 30%, alternatively within 20%, or alternatively within 15% of a target melt index. In such aspect, the polyethylene resin can be designated as high quality resin. For purposes of the disclosure herein, the term "target melt index" refers to the melt index of a final product resin (as opposed to an intermediate resin product, e.g., an intermediate resin product transferred from one reactor or reaction zone to another reactor or reaction zone). As will be appreciated by one of skill in the art, and with the help of this disclosure, although intermediate resin products could be produced in polyolefin production systems employing two or more reactors in series (e.g., an intermediate resin product recovered from a first reactor and introduced to a second reactor), the target melt index characterizes the final product recovered from the polyolefin production system, e.g., a final polyolefin (e.g., polyethylene) resin product. Further, and as will be appreciated by one of skill in the art, and with the help of this disclosure, the melt index of intermediate resin products can be very small, for example very close to 0 gram per 10 minutes (g/10 min), and it could also require modified diameter melt indexer orifices for measuring the melt index, such as 2.75 mm, as opposed to the standard 2.09 mm melt indexer orifice diameter.

For example, if the target melt index is about 9.5 g/10 min (as determined under a force of 21.6 kg in accordance with ASTM D1238), a melt index that is within 30% of the target melt index gives a range of melt index values of 9.5±2.85 g/10 min, i.e., from about 6.65 g/min to about 12.35 g/10 min (e.g., 30% of 9.5 is 2.85); and a resin having a melt index of 11 g/10 min is characterized by a melt index that is the same as the target melt index.

In an aspect, the target melt index can be from about 5 gram per 10 minutes (g/10 min) to about 25 g/10 min, alternatively from about 6 g/10 min to about 20 g/10 min, or alternatively from about 7 g/10 min to about 15 g/10 min, as determined under a force of 21.6 kg in accordance with ASTM D1238. For purposes of the disclosure herein, the target melt index refers to the melt index measured in accordance with ASTM D1238 under any suitable force load (e.g., 2.16 kg, 5 kg, 21.6 kg, and the like).

In some aspects, the target melt index can be from about 0.001 g/10 min to about 0.25 g/10 min, alternatively from about 0.01 g/10 min to about 0.2 g/10 min, or alternatively from about 0.1 g/10 min to about 0.15 g/10 min, as determined under a force of 2.16 kg in accordance with ASTM D1238. In other aspects, the target melt index can be from about 0.1 g/10 min to about 1 g/10 min, alternatively from about 0.2 g/10 min to about 0.8 g/10 min, alternatively from about 0.25 g/10 min to about 0.75 g/10 min, or alternatively from about 0.3 g/10 min to about 0.7 g/10 min, as determined under a force of 2.16 kg in accordance with ASTM D1238.

Resins characterized by a melt index that is different from the target melt index, e.g., resins excluding a resin having a melt index within 30% of a target melt index, can be designated as low quality resins. In aspects where the first polyethylene resin is characterized by a melt index that is different from the target melt index, the method of producing polyethylene resin as disclosed herein can comprise selecting a second value for one or more parameters of the plurality of parameters for at least one of the one or more reaction zones, wherein the second value provides for the melt index of the resin to become the same as or at least approach (e.g., get closer to) the target melt index.

In an aspect, a method of producing polyethylene resins as disclosed herein can comprise determining a density for the polyethylene resin (e.g., first polyethylene resin, second polyethylene resin). The method can further comprise comparing the density of the polyethylene resin with a target density.

In an aspect, the polyethylene resin (e.g., first polyethylene resin, second polyethylene resin) can be characterized by a density that is the same as the target density, e.g., a density that is within 2.5%, alternatively within 1%, or alternatively within 0.5% of a target density. In such aspect, the polyethylene resin can be designated as high quality resin. For purposes of the disclosure herein, the term "target density" refers to the density of a final product resin (as opposed to an intermediate resin product, e.g., an intermediate resin product transferred from one reactor or reaction zone to another reactor or reaction zone). As will be appreciated by one of skill in the art, and with the help of this disclosure, although intermediate resin products could be produced in polyolefin production systems employing two or more reactors in series (e.g., an intermediate resin product recovered from a first reactor and introduced to a second reactor), the target density characterizes the final product recovered from the polyolefin production system, e.g., a final polyolefin (e.g., polyethylene) resin product.

For example, if the target density is about 0.9250 g/cc (as determined in accordance with ASTM D1505), a density that is within 2.5% of the target density gives a range of density values of 0.9250±0.0463 g/cc, i.e., from about 0.9019 g/cc to about 0.9481 g/cc (e.g., 2.5% of 0.9250 is 0.0231); and a resin having a density of 0.9300 g/c is characterized by a density that is the same as the target density.

As will be appreciated by one of skill in the art, and with the help of this disclosure, various types of suitable polymers can be characterized as having various densities. For example, a Type I polymer can be characterized as having a density (e.g., target density) in a range of from about 0.910 g/cc to about 0.925 g/cc, alternatively, a Type II polymer can be characterized as having a density (e.g., target density) from about 0.926 g/cc to about 0.940 g/cc, alternatively, a Type III polymer can be characterized as having a density (e.g., target density) from about 0.941 g/cc to about 0.959 g/cc, alternatively, a Type IV polymer can be characterized as having a density (e.g., target density) of greater than about 0.960 g/cc. Resin density is determined in accordance with ASTM D1505.

Resins characterized by a density that is different from the target density, e.g., resins excluding a resin having a density within 2.5% of a target density, can be designated as low quality resins. In aspects where the first polyethylene resin is characterized by a density that is different from the target density, the method of producing polyethylene resin as disclosed herein can comprise selecting a second value for one or more parameters of the plurality of parameters for at least one of the one or more reaction zones, wherein the second value provides for the density of the resin to become the same as or at least approach (e.g., get closer to) the target density.

Without wishing to be limited by theory, and as will be appreciated by one of skill in the art, and with the help of this disclosure, while melt index is an useful parameter for screening unimodal polyethylene resins, melt index is not a reliable indicator for the properties (e.g., molecular weight, such as weight average molecular weight ($M_w$); molecular weight distribution) of the multimodal (e.g., bimodal) polyethylene resins. For example, for unimodal polyethylene resins of the same family (similar polyethylene resins), melt index can generally serve as a proxy for molecular weight (e.g., weight average molecular weight ($M_w$)) and molecular weight distribution. However, multimodal (e.g., bimodal) polyethylene resins do not display a clear correlation between melt index, and molecular weight (e.g., weight average molecular weight ($M_w$)) and molecular weight distribution. For example, some bimodal polyethylene resins having lower melt index can have lower molecular weight (e.g., lower weight average molecular weight ($M_w$)) than those resins of the same family having higher melt index, which is in contrast to unimodal polyethylene resins where lower melt index resins always have higher molecular weight (e.g., higher weight average molecular weight ($M_w$)) than higher melt index resins. Further, and without wishing to be limited by theory, a bimodal resin is much more complicated than a unimodal resin. For unimodal resins, the peak molecular weight oftentimes defines the composition of the polymer, and thus the properties of the polymer. For bimodal resins, not only can the populations of the two components change, the molecular weights (e.g., weight average molecular weights ($M_w$)) of the two components can also vary independently. To define a bimodal resin, at least three independent parameters are needed: the molecular weight of the LMW component (e.g., weight average molecular weight ($M_w$) of the LMW component), the molecular weight of the BMW (e.g., weight average molecular weight ($M_w$) of the BMW component), and the relative population ratio of the two components. As will be appreciated by one of skill in the art, and with the help of this disclosure, different bimodal resins having the same melt index can have very different molecular weight distribution profiles, which in return, can result in very different processability and end-use properties for each of the different bimodal resins. Further, and as will be appreciated by one of skill in the art, and with the help of this disclosure, even more parameters would be needed to define trimodal resins, as compared to the number of parameters needed to define unimodal and bimodal resins.

In an aspect, a method of producing polyethylene resins as disclosed herein can comprise determining a dynamic viscosity ($\eta_s^*$) for the polyethylene resin (e.g., first polyethylene resin, second polyethylene resin) across a range of shear rate ($\omega_1$) of from about 0.01 $s^{-1}$ to about 1,000 $s^{-1}$, or alternatively from about 0.05 $s^{-1}$ to about 500 $s^{-1}$, or alternatively from about 0.0316 $s^{-1}$ to about 316 $s^{-1}$. Dynamic viscosity or absolute viscosity, also referred to as dynamic melt viscosity, or melt viscosity, is a measure of a fluid's (e.g., polymer melt's) internal resistance to flow. Generally, the polyethylene resin is melted at a suitable temperature (e.g., about 190° C.) for melt rheology measurements, such as determining the dynamic viscosity of the resin. The shear rate refers to the angular frequency of oscillatory shear deformation. The dynamic viscosity is generally measured at equal to or greater than 3, alternatively equal to or greater than 5, alternatively equal to or greater than 10, or alternatively equal to or greater than 15 shear rate values across a range of shear rate ($\omega_1$) of from about 0.01 s$^{-1}$ to about 1,000 s$^{-1}$.

For example, dynamic viscosity measurements can be performed as follows. The polymer samples can be compression molded at 182° C. The samples can be allowed to melt at a relatively low pressure for 1 minute (min), and then the molten samples can be subjected to a high molding pressure for an additional 2 min to yield molded samples. The molded samples can then be quenched in a room temperature press, and followed by stamping 25.4 mm diameter disks out of the molded samples for the measurement. Dynamic frequency sweep tests can be performed with parallel plates of 25 mm diameter at 190° C. using a rotational rheometer (e.g., Physica MCR-500, Anton Paar). The test chamber of the rheometer can be purged with nitrogen to minimize oxidative degradation. After thermal equilibration, the disk specimens can be squeezed between the plates to a 1.6 mm thickness, and the excess sample can be trimmed. The dynamic frequency sweep tests can be performed by applying a small-strain (1~10%) oscillatory shear in the linear viscoelastic regime at any suitable angular frequencies, for example from about 0.01 s$^{-1}$ to about 1,000 s$^{-1}$, or alternatively from about 0.0316 s$^{-1}$ to about 316 s$^{-1}$. The dynamic viscosity ($\eta^*$) can be measured as a function of the angular frequency ($\omega$).

In an aspect, a method of producing polyethylene resins as disclosed herein can comprise comparing the dynamic viscosity of the polyethylene resin (e.g., first polyethylene resin, second polyethylene resin) with a target dynamic viscosity ($\eta_c^*$), wherein comparing the dynamic viscosity comprises calculating a dynamic viscosity deviation (% MVD) from the target dynamic viscosity. The % MVD can be calculated according to equation 1:

$$\% MVD = 100 \times \sqrt{\frac{\sum_i \left[ \frac{(\eta_s^*)_{\omega_i} - (\eta_c^*)_{\omega_i}}{(\eta_c^*)_{\omega_i}} \right]^2}{i}}, \quad (1)$$

wherein $(\eta_s^*)_{\omega_i}$ is the dynamic viscosity of the polyethylene resin at a shear rate $\omega_i$, wherein $(\eta_c^*)_{\omega_j}$ is the target dynamic viscosity at the shear rate $\omega_j$, wherein i represents the number of data points collected for the dynamic viscosity ($\eta_s^*$) across the range of shear rate ($\omega_i$), and wherein i is equal to or greater than 3, alternatively equal to or greater than 5, alternatively equal to or greater than 10, or alternatively equal to or greater than 15. Generally, % MVD is a measure of the rheology difference between a polyethylene resin sample and a target resin characterized by a target rheology, e.g., a target dynamic viscosity.

In an aspect, the polyethylene resin (e.g., first polyethylene resin, second polyethylene resin) can be characterized by a dynamic viscosity that is the same as the target dynamic viscosity, e.g., a % MVD of less than about 100%, alternatively less than about 50%, alternatively less than about 30%, alternatively less than about 25%, alternatively less than about 20%, or alternatively less than about 15%. In such aspect, the polyethylene resin can be designated as high quality resin. In some aspects, when a resin is characterized by a dynamic viscosity that is the same as the target dynamic viscosity, e.g., a resin having a % MVD of less than about 100%, the resin can also be characterized by a melt index that is the same as the target melt index, e.g., a melt index that is within 30% of a target melt index.

Without wishing to be limited by theory, since melt zero-shear viscosity ($\eta_0$) is proportional to the 3.4$^{th}$ power to the weight average molecular weight ($M_w$), % MVD can be a fairly large number, such as 100% or greater. Further, and without wishing to be limited by theory, and as will be appreciated by one of skill in the art, and with the help of this disclosure, the theoretical minimum value for % MVD is 0% (e.g., full match between the sample resin and the target resin); however, and as will be appreciated by one of skill in the art, and with the help of this disclosure, in practice, the % MVD is always greater than 0%, owing to the experimental design (e.g., reproducibility), even when different runs of the same sample are compared to each other. The lower the value for % MVD, the closer the resin sample is to a target resin sample (e.g., better match between the sample resin and the target resin).

Resins characterized by a dynamic viscosity that is different from the target dynamic viscosity, e.g., resins having a % MVD of equal to or greater than about 100%, alternatively equal to or greater than about 50%, alternatively equal to or greater than about 30%, alternatively equal to or greater than about 25%, alternatively equal to or greater than about 20%, or alternatively equal to or greater than about 15%, can be designated as low quality resins. In aspects where the first polyethylene resin is characterized by a dynamic viscosity that is different from the target dynamic viscosity, the method of producing polyethylene resin as disclosed herein can comprise selecting a second value for one or more parameters of the plurality of parameters for at least one of the one or more reaction zones, wherein the second value provides for the dynamic viscosity of the resin to become the same as or at least approach (e.g., get closer to) the target dynamic viscosity. The second value decreases the % MVD.

While % MVD can help define a bimodal resin better than the melt index and density in the absence of dynamic viscosity, sometimes bimodal resins that meet melt index, density, and % MVD specifications can display molecular weight distribution profiles different from the target resin, which in turn can result in processability and end-use properties that can be different from those of the target resin.

In an aspect, a method of producing polyethylene resins as disclosed herein can comprise determining a GPC curve profile of the polyethylene resin, wherein the GPC curve profile comprises a differential weight fraction (dw/d(log M)) as a function of log M, wherein M is the molecular weight of the weight fraction w. The method can further comprise comparing the GPC curve profile of the second polyethylene resin with a target GPC curve profile. In an aspect, comparing the GPC curve profile with a target GPC curve profile comprises calculating a GPC curve profile deviation (% GPCD) from the target GPC curve profile. The % GPCD can be calculated according to equation 2:

$$\% \ GPCD = 100 \times \sum_j \text{Abs}\left[\left(\frac{dw}{d(\text{Log } M)}\right)_{P,j} - \left(\frac{dw}{d(\text{Log } M)}\right)_{T,j}\right] * d(\text{Log } M)_j \quad (2)$$

wherein $$\left(\frac{dw}{d(\text{Log } M)}\right)_{P,j}$$

is the differential weight fraction of the polyethylene for a fraction j of the polyethylene molecules having the molecular weight M, and wherein $$\left(\frac{dw}{d(\text{Log } M)}\right)_{T,j}$$

is the target differential weight fraction for the fraction j of the polyethylene molecules. GPC curve profiles can be acquired with a rapid GPC, which is a gel-permeation chromatograph instrument that offers near real-time turn-around of GPC results, such as molecular weight averages and various molecular weight distributions. Without wishing to be limited by theory, since many polymer properties are dictated by polymer composition, it is important to take molecular weight distribution into account in order to make bimodal resins that are not only on specifications, but also on MWD target.

In an aspect, the polyethylene resin (e.g., first polyethylene resin, second polyethylene resin) can be characterized by a GPC curve profile that is the same as the target GPC curve profile, e.g., a % GPCD of less than about 15%, alternatively less than about 10%, alternatively less than about 5%, or alternatively less than about 2.5%. In such aspect, the polyethylene resin can be designated as high quality resin. Without wishing to be limited by theory, and as will be appreciated by one of skill in the art, and with the help of this disclosure, the theoretical minimum value for % GPCD is 0% (e.g., full match between the sample resin and the target resin), while the theoretical maximum value is 100% (e.g., complete mismatch between the sample resin and the target resin). The lower the value for % GPCD, the closer the resin sample is to a target resin sample (e.g., better match between the sample resin and the target resin).

Resins characterized by a GPC curve profile that is different from the target GPC curve profile, e.g., resins having a % GPCD of equal to or greater than about 15%, alternatively equal to or greater than about 10%, alternatively equal to or greater than about 5%, or alternatively equal to or greater than about 2.5%, can be designated as low quality resins. As will be appreciated by one of skill in the art, and with the help of this disclosure, a resin characterized by a GPC curve profile that is different from the target GPC curve profile could have any % GPCD value that is equal to or greater than about 15%, such as 20%, 30%, 40%, 50%, 60%, 70%, or greater. In aspects where the first polyethylene resin is characterized by a GPC curve profile that is different from the target GPC curve profile, the method of producing polyethylene resin as disclosed herein can comprise selecting a second value for one or more parameters of the plurality of parameters for at least one of the one or more reaction zones, wherein the second value provides for the GPC curve profile of the resin to become the same as or at least approach (e.g., get closer to) the target GPC curve profile. The second value decreases the % GPCD. As will be appreciated by one of skill in the art, and with the help of this disclosure, the value of % GPCD correlates with a variety of variables, such as the ratio of HMW component to LMW component, the $H_2$/MON ratio, ethylene concentration (e.g., ethylene partial pressure), temperature in the reactor, and the like. In some aspects, a single operational parameter (e.g., $H_2$/MON ratio, ethylene concentration (e.g., ethylene partial pressure), temperature in the reactor or reaction zone, and the like) can be changed in at least one reactor or reaction zone to help minimize % GPCD. In other aspects, two or more operational parameters (e.g., $H_2$/MON ratio, ethylene concentration (e.g., ethylene partial pressure), temperature in the reactor, and the like) can be changed (e.g., concerted change of operational parameters) in at least one reactor or reaction zone to help minimize % GPCD.

In some aspects, resins having a % GPCD of less than a first threshold (e.g., less than about 15%, alternatively less than about 12%, alternatively less than about 10%, alternatively less than about 6%, or alternatively less than about 3%) can be designated as high quality resins. Resins having a % GPCD of equal to or greater than a second threshold (e.g., equal to or greater than 6%, alternatively equal to or greater than 12%, alternatively equal to or greater than 20%, alternatively equal to or greater than 24%, or alternatively equal to or greater than 30%), wherein the second threshold is greater than the first threshold, can be designated as low quality resins. Resins having a % GPCD of equal to or greater than the first threshold and less than the second threshold can be designated as intermediate quality resins, wherein the intermediate quality resins can be subjected to additional testing for various properties, to determine whether the resins can be used as in a specific application (e.g., film manufacturing, pipe manufacturing), or if the resins have to be downgraded to low quality resins. In some aspects, the first threshold and the second threshold can be set at 15% and 30%, alternatively 12% and 24%, alternatively 10% and 20%, alternatively 6% and 12%, or alternatively 3% and 6%, respectively.

In some aspects, resins that meet melt index, density, % MVD, and % GPCD specifications can still display variations in the LMW end of the molecular weight profile. In such aspects, the first threshold can be adjusted to a lower value in order to bring the LMW component as close to the target as possible. Since both % MVD and molecular weight (e.g., % GPCD) are sensitive to the change in the HMW end, any undesired movement in the HMW end of the molecular weight profile can be picked up easily by these two parameters.

In an aspect, a method of producing polyethylene resins as disclosed herein can comprise determining a weight average molecular weight ($M_w$) of the polyethylene resin from a GPC curve profile, wherein the GPC curve profile comprises a differential weight fraction (dw/d(log M)) as a function of log M, wherein M is the molecular weight of the weight fraction w. The method can further comprise comparing the $M_w$ of the polyethylene resin with a target M. In an aspect, comparing the $M_w$ with a target $M_w$ comprises calculating a $M_w$ deviation (% $M_wD$) from the target $M_w$. The % $M_wD$ can be calculated according to equation 3:

$$\% M_wD = 100 \times Abs((M_{w,T} - M_{w,P})/M_{w,T}) \quad (3)$$

wherein $M_{w,T}$ is the weight average molecular weight ($M_w$) of the target, and wherein $M_{w,P}$ is the $M_w$ of the product. The weight average molecular weight ($M_w$) describes the size average (e.g., molecular weight distribution) of a polymer composition and can be calculated according to equation 4:

$$M_w = \frac{\sum_i N_i M_i^2}{\sum_i N_i M_i} \quad (4)$$

wherein $N_i$ is the number of molecules of molecular weight $M_i$. All molecular weight averages are expressed in gram per mole (g/mol) or Daltons (Da), or in kg/mol or kDa. As will be appreciated by one of skill in the art, and with the help of this disclosure, the polyethylene resin can have any suitable $M_w$, as a polyethylene production system as disclosed herein can produce a wide variety of polyethylene resins, which can display a wide variety of $M_w$.

In an aspect, the polyethylene resin (e.g., first polyethylene resin, second polyethylene resin) can be characterized by a $M_w$ that is the same as the target $M_w$, e.g., a % $M_wD$ of less than about 20%, alternatively less than about 10%, alternatively less than about 5%, or alternatively less than about 2.5%. In such aspect, the polyethylene resin can be designated as high quality resin.

Resins characterized by a $M_w$ that is different from the target $M_w$, e.g., resins having a % $M_wD$ of equal to or greater than about 20%, alternatively equal to or greater than about 10%, alternatively equal to or greater than about 5%, or alternatively equal to or greater than about 2.5%, can be designated as low quality resins. As will be appreciated by one of skill in the art, and with the help of this disclosure, a resin characterized by a $M_w$ that is different from the target $M_w$ could have any % $M_wD$ value that is equal to or greater than about 20%, such as 25%, 30%, 40%, 50%, 60%, 70%, or greater. In aspects where the first polyethylene resin is characterized by a $M_w$ that is different from the target $M_w$, the method of producing polyethylene resin as disclosed herein can comprise selecting a second value for one or more parameters of the plurality of parameters for at least one of the one or more reaction zones, wherein the second value provides for the $M_w$ of the resin to become the same as or at least approach (e.g., get closer to) the target $M_w$. The second value decreases the % $M_wD$.

As will be appreciated by one of skill in the art, and with the help of this disclosure, while a GPC curve profile can provide for calculating a variety of parameters, $M_w$ can be most accurately determined by GPC. However, $M_w$ alone does not adequately define a molecular weight distribution profile relative to the molecular weight distribution profile of a target resin. While % $M_wD$ can be used as a tool for assessing the quality of a resin, the use of % GPCD provides for a more complete assessment of multimodal resins, e.g., % GPCD accounts for the entire molecular weight distribution profile of the resin as compared to that of a target resin. % GPCD accounts better for the contribution of the LMW component, when compared to % $M_wD$. However, and as will be appreciated by one of skill in the art, and with the help of this disclosure, % $M_wD$ can be calculated faster than the % GPCD.

In an aspect, comparing one of more properties of the polyethylene resin with corresponding target properties can provide for near real-time feedback to the one or more reaction zones. The term "near real-time," as used herein, refers to a delay that is introduced by automated data processing between the occurrence of an event (e.g., live event) and the use of processed data. For example, classifying an event as a near real-time event refers to the delay that allows the use of the processed data near the time of the live event, wherein such delay refers to the difference between the real-time event occurrence and the processing time. For example, the difference between the real-time event occurrence and the processing time can be less than 15 minutes (min), less than 30 min, less than 45 min, less than 1 hour (h), less than 2 h, less than 3 h, and the like. Further, such delay can refer to a time interval between when data are received for analysis and when analysis is performed and displayed on an electronic display screen (e.g., monitor screen, computer screen), wherein such time interval can be from less than about 1 min to less than about 10 min, or alternatively from about 3 seconds (s) to about 3 min.

The terms "real-time" or "actual real-time" as used herein can refer to the instantaneous data processing, wherein a measurement (e.g., measured item, measurement data) is transmitted and received at the same time the measurement is occurring, e.g., data or information is instantaneously or nearly instantaneously streamed or transmitted. For example, the real-time data can be rheology analysis data (e.g., dynamic viscosity data) or GPC curve profile data that can be provided instantaneously (e.g., as soon as it is obtained), such as within about 2 seconds or less from the time the measurement (e.g., a dynamic viscosity reading from a viscometer; a GPC curve profile from a rapid GPC) is occurring, to a computer system or computer readable medium.

As will be appreciated by one of skill in the art, and with the help of this disclosure, while the processing of the data (e.g., resin property data) can occur in real-time, the feedback to the reaction zone occurs in near real-time. Data processing can be instantaneous (i.e., real-time) data processing, wherein data (e.g., resin property data) is transmitted and received at the same time the data processing is occurring, e.g., data or information is instantaneously or nearly instantaneously streamed or transmitted. The real-time data can be melt index data, density data, dynamic viscosity data, GPC curve profile data, and the like, or combinations thereof, wherein the real-time data can be provided instantaneously (e.g., as soon as it is obtained) from a testing system to a control system, as will be described in more detail later herein.

As will be appreciated by one of skill in the art, and with the help of this disclosure, there is a time delay between the time when the reaction zone produces the resin, and the time the resin is tested for properties, and further the time when the properties are transmitted from the testing system to the control system; which introduces a delay in the time when the reaction zone receives feedback about the properties of the produced resin (e.g., near real-time feedback). Generally, the processes for the production of multimodal polyethylene resin are continuous processes, and the produced resin is sampled and tested for properties at various time intervals during the production process, such as every 15 min, every 30 min, every 45 min, every 1 h, every 2 h, every 3 h, and the like. Further, and as will be appreciated by one of skill in the art, and with the help of this disclosure, such resin sampling and testing can provide for near real-time feedback about resin properties to the reaction zones, in the context of the entire life time of the continuous production process.

As will be appreciated by one of skill in the art, and with the help of this disclosure, the value of a target property (e.g., target melt index, target density, target molecular weight, target viscosity, target molecular weight distribution profile, and the like, or combinations thereof) correlates with a variety of operational parameters, such as ethylene concentration, comonomer concentration, $H_2$/MON ratio, temperature, catalyst concentration, cocatalyst concentration, pressure, residence time, and the like, or combinations thereof. In some aspects, a single operational parameter (e.g., ethylene concentration, comonomer concentration, $H_2$/MON ratio, temperature, catalyst concentration, cocatalyst concentration, pressure, residence time, and the like) can be changed in at least one reactor to help drive a resin product to meet desired specifications (e.g., target properties). In other aspects, two or more operational parameters (e.g., ethylene concentration, comonomer concentration, $H_2$/MON ratio, temperature, catalyst concentration, cocatalyst concentration, pressure, residence time, and the like, or combinations thereof) can be changed (e.g., concerted change of operational parameters) in at least one reactor to help drive a resin product to meet desired specifications (e.g., target properties).

In an aspect, a system for producing polyethylene can comprise one or more polymerization reaction zones configured to produce a polyethylene resin, wherein each reaction zone of the one or more reaction zones operates independently at a plurality of parameters, and wherein each parameter of the plurality of parameters is selected from the group consisting of ethylene concentration, comonomer concentration, hydrogen to olefin monomer ratio ($H_2$/ MON), temperature, catalyst concentration, cocatalyst concentration, pressure, and residence time; a testing system configured to characterize the polyethylene resin for one or more resin properties, wherein the one or more resin properties comprises at least one of dynamic viscosity, gel permeation chromatography (GPC) curve profile, weight average molecular weight ($M_w$), or combinations thereof; and a control system configured to receive the one or more resin properties from the testing system, wherein the control system comprises at least one processor and at least one controller; wherein the at least one processor compares the one or more resin properties with corresponding target properties; wherein the at least one processor, when at least one of the one or more resin properties is different when compared to the corresponding target property, signals the at least one controller; and wherein the at least one controller adjusts at least one of the plurality of parameters independently for at least one reaction zone of the one or more reaction zones. In such aspect, the control system can provide for near real-time feedback to the one or more reaction zones. The one or more resin properties can further comprise density, melt index, or both density and melt index.

In an aspect, the testing system can comprise a device for measuring the density of a resin, such as a pycnometer; a device for measuring the melt index of a resin, such as a melt flow index tester; a device for measuring the dynamic viscosity of a resin, such as a viscometer or a Brookfield viscometer; a device for measuring the GPC curve profile of a resin, such as a gel permeation chromatograph, or a size exclusion chromatograph; and the like.

In aspects where the one or more resin properties are the same when compared to the corresponding target properties, the at least one processor does not require further action for correcting the one or more resin properties.

Figure 2:
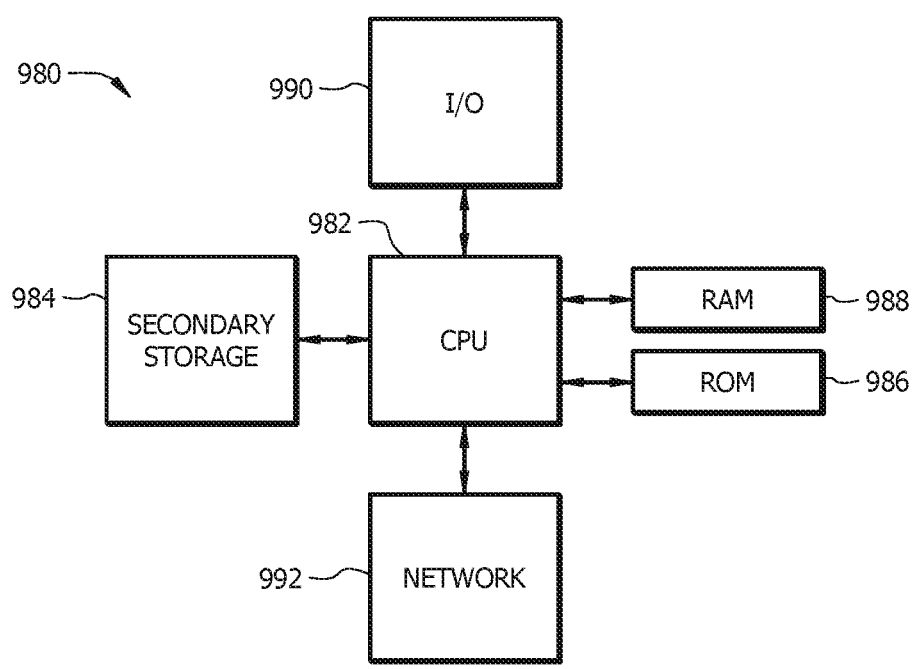
FIG. 2 illustrates a schematic layout of a computer system.

In an aspect, the control system can comprise at least one processor (e.g., computer such as shown in FIG. 2) and at least one controller (e.g., actuator). Generally, a control system is a device, or set of devices (e.g., at least one processor and at least one controller) that manages, commands, directs or regulates the behavior of other devices or systems (e.g., polyethylene production equipment or machines, such as a device for introducing a catalyst system component to a reaction zone, a device for introducing a reactant (e.g., monomer, comonomer, hydrogen) to a reaction zone, a temperature controller, and the like). One or more aspects of the control system (e.g., the processor, memory, etc.) can be implemented via one or more computer systems 980 such as shown in FIG. 2. For example, computer system 980 can execute software code stored in memory that executes one or more of the methods disclosed herein (e.g., any of the first through one hundred and fourth aspects described in the Additional Disclosure portion of the present specification), and the computer system 980 can further communicate with one or more controllers in signal communication with at least one controller coupled to process equipment associated with a reaction zone, wherein the least one controller adjusts at least one of the plurality of parameters independently for at least one reaction zone of the one or more reaction zones.

In an aspect, the control system can be a distributed control system (DCS). Generally, a DCS is a control system for a process (e.g., polyethylene production process) or plant (e.g., polyethylene production plant), wherein control elements are distributed throughout the control system (as opposed to non-distributed control systems, which use a single controller at a central location). DCS controllers can be connected by communications networks for command and monitoring.

In an aspect, the at least one processor can receive from the testing system the density of the polyethylene resin, wherein the at least one processor can compare the density of the polyethylene resin with the target density. In aspects where the density of the polyethylene resin is different from the target density (e.g., resins excluding a resin having a density within 2.5% of a target density), the at least one processor can signal the at least one controller; wherein the at least one controller can adjust at least one of the plurality of parameters independently for at least one reaction zone of the one or more reaction zones, such that the produced resin meets density specifications (e.g., the density of the produced resin is within 2.5% of a target density). In aspects where the density of the resin is different from the target density, the at least one processor can designate the resin as low quality resin. In aspects where the density of the resin is the same as the target density, the at least one processor can designate the resin as high quality resin.

In an aspect, the at least one processor can receive from the testing system the melt index of the polyethylene resin, wherein the at least one processor can compare the melt index of the polyethylene resin with the target melt index. In aspects where the melt index of the polyethylene resin is different from the target melt index (e.g., resins excluding a resin having a melt index within 30% of a target melt index), the at least one processor can signal the at least one controller; wherein the at least one controller can adjust at least one of the plurality of parameters independently for at least one reaction zone of the one or more reaction zones, such that the produced resin meets melt index specifications (e.g., the melt index of the produced resin is within 30% of a target melt index). In aspects where the melt index of the resin is different from the target melt index, the at least one processor can designate the resin as low quality resin. In aspects where the melt index of the resin is the same as the target melt index, the at least one processor can designate the resin as high quality resin.

In an aspect, the at least one processor can receive from the testing system the dynamic viscosity of the polyethylene resin, wherein the at least one processor can compare the dynamic viscosity of the polyethylene resin with the target dynamic viscosity, for example by calculating a % MVD from the target dynamic viscosity. In aspects where the dynamic viscosity of the polyethylene resin is different from the target dynamic viscosity (e.g., % MVD of equal to or greater than about 100%), the at least one processor can signal the at least one controller; wherein the at least one controller can adjust at least one of the plurality of parameters independently for at least one reaction zone of the one or more reaction zones, such that the produced resin meets dynamic viscosity specifications (e.g., % MVD of less than about 100%). In aspects where the dynamic viscosity of the resin is different from the target dynamic viscosity, the at least one processor can designate the resin as low quality resin. In aspects where the dynamic viscosity of the resin is the same as the target dynamic viscosity, the at least one processor can designate the resin as high quality resin.

In an aspect, the at least one processor can receive from the testing system the GPC curve profile of the polyethylene resin, wherein the at least one processor can compare the GPC curve profile of the polyethylene resin with the target GPC curve profile, for example by calculating a % GPCD from the target GPC curve profile. In aspects where the GPC curve profile of the polyethylene resin is different from the target GPC curve profile (e.g., % GPCD of equal to or greater than about 15%), the at least one processor can signal the at least one controller; wherein the at least one controller can adjust at least one of the plurality of parameters independently for at least one reaction zone of the one or more reaction zones, such that the produced resin meets GPC curve profile specifications (e.g., % GPCD of less than about 15%). In aspects where the GPC curve profile of the resin is different from the target GPC curve profile, the at least one processor can designate the resin as low quality resin. In aspects where the GPC curve profile of the resin is the same as the target GPC curve profile, the at least one processor can designate the resin as high quality resin.

In an aspect, the at least one processor can receive from the testing system the $M_w$ of the polyethylene resin, wherein the at least one processor can compare the $M_w$ of the polyethylene resin with the target $M_w$, for example by calculating a % $M_wD$ from the target $M_w$. In aspects where the $M_w$ of the polyethylene resin is different from the target $M_w$ (e.g., % $M_wD$ of equal to or greater than about 20%), the at least one processor can signal the at least one controller; wherein the at least one controller can adjust at least one of the plurality of parameters independently for at least one reaction zone of the one or more reaction zones, such that the produced resin meets $M_w$ specifications (e.g., % $M_wD$ of less than about 20%). In aspects where the $M_w$ of the resin is different from the target $M_w$, the at least one processor can designate the resin as low quality resin. In aspects where the $M_w$ of the resin is the same as the target $M_w$, the at least one processor can designate the resin as high quality resin.

In some aspects of this disclosure, and as will be appreciated by one of skill in the art, adjusting the amount of one of the components (e.g., catalyst system components, reactants) introduced to a reaction zone can modify the residence time in the reaction zone, and as such the properties of the produced resin can still be different when compared to the corresponding target properties, even upon adjusting the operational parameters. In such aspects, the processor can continue to signal the controller and direct the controller to correct at least one operational parameter, until the target resin properties are met.

In an aspect, a system for monitoring polyethylene resin quality can comprise a testing system configured to characterize a plurality of multimodal polyethylene resins for one or more resin properties, as disclosed herein; a computer system configured to receive the one or more resin properties from the testing system, wherein the computer system comprises at least one processor; wherein the at least one processor compares the one or more resin properties with corresponding target properties, as disclosed herein; wherein the at least one processor, when at least one of the one or more resin properties is different when compared to the corresponding target property, designates the resin as low quality resin, as disclosed herein; wherein the at least one processor, when the one or more resin properties is the same when compared to the corresponding target property, designates the resin as high quality resin, as disclosed herein; and a sorting system configured to receive quality resin designations from the computer system, wherein the sorting system physically segregates the low quality resin from the high quality resin for further storage or processing.

In some aspects, the sorting system can physically place the high quality resins and the low quality resins in different (e.g., distinct) places for storage, wherein each individual storage place (e.g., pallets, bins, containers) can be labelled or otherwise designated for the particular type of resin that they hold. The sorting system can label or otherwise designate the storage place for each type of resin, for example by indicating the properties of the resin, the intended end-use of the resin (e.g., pellets, pipe, film), and the like.

In some aspects, the sorting system can indicate that the resin (e.g., high quality resin, low quality resin) can be directly sent to processing, for example to be pelletized for further storage or further processing.

In an aspect, a system for processing polyethylene resins can comprise a testing system configured to characterize a plurality of polyethylene resins for one or more resin properties, as disclosed herein; a computer system configured to receive the one or more resin properties from the testing system, wherein the computer system comprises at least one processor; wherein the at least one processor compares the one or more resin properties with corresponding target properties, as disclosed herein; wherein the at least one processor, when at least one of the one or more resin properties is different when compared to the corresponding target property, designates the resin as low quality resin; wherein the at least one processor, when the one or more resin properties are the same when compared to the corresponding target properties, designates the resin as selected polyethylene (e.g., high quality resin); and a shaping system configured to receive the selected polyethylene and process the selected polyethylene into a shaped article. In such aspect, the system for processing polyethylene resins can further comprise a sorting system configured to receive quality resin designations from the computer system, wherein the sorting system physically segregates the low quality resin from the high quality resin, as disclosed herein, prior to communicating the selected polyethylene (e.g., high quality resin) to the shaping system.

Once the polyethylene resin is designated as either high quality resin or low quality resin, the polyethylene resin can be processed by any suitable process or series of processes configured to produce a polymer product as can be suitable for commercial or industrial usage, storage, transportation, further processing, or combinations thereof.

Processing the polyethylene resin can comprise routing the resin to a shaping system comprising a polymer processor. The polymer processor can be configured for the performance of a suitable processing means (e.g., to form various articles), nonlimiting examples of which include cooling, injection molding, melting, pelletizing, film blowing, cast film, blow molding, extrusion molding, rotational molding, thermoforming, cast molding, fiber spinning, and the like, or combinations thereof. Various additives and modifiers can be added to the resin to provide better processing during manufacturing and for desired properties in the end-use product. Nonlimiting examples of such additives can include surface modifiers such as slip agents, antiblocks, tackifiers; antioxidants such as primary and secondary antioxidants; pigments; processing aids such as waxes/oils and fluoroelastomers; special additives such as fire retardants, antistats, scavengers, absorbers, odor enhancers, and degradation agents; or combinations thereof.

The processed resin can include other suitable additives. Such additives can be used singularly or in combination and can be included in the resin before, during or after preparation of the resin as disclosed herein. Such additives can be added via known techniques, for example during an extrusion or compounding step, such as during pelletization or subsequent processing into an end-use article.

The polymer processor can be configured to form a suitable resin product. Nonlimiting examples of suitable resin products as can result from processing the polyethylene resin include films, powders, pellets, resins, liquids, or any other suitable form as will be appreciated by those of skill in the art. Such a suitable output can be for use in, for example, one or more of various consumer or industrial products. For example, the resin product can be utilized in any one or more of various articles (e.g., shaped articles), including, but not limited to, bottles, drums, toys, containers, household containers, utensils, film products, tanks, fuel tanks, pipes, membranes, geomembranes, and liners. The polymer processor can be configured to form pellets for transportation to a consumer product manufacturer.

In some aspects, the shaping system can be configured to receive the high quality polyethylene resin and process the high quality polyethylene resin into a film. In such aspects, the high quality polyethylene resin can be a bimodal resin.

In some aspects, the shaping system can be configured to receive the high quality polyethylene resin and process the high quality polyethylene resin into a pipe. In such aspects, the high quality polyethylene resin can be a bimodal resin.

A lot of the field failures in pipe applications (e.g., pressure pipe applications) are attributable to slow crack growth (SCG). This has led to the development of many lab-scale tests, such as the Pennsylvania Edge-Notch Tensile Test (PENT; ASTM F1473), to predict the resistance to SCG of various polyethylenes. In the PENT test, a notched polyethylene specimen is subjected to creep by the application of a constant tensile load at 80° C. The applied load is such that the initial stress is 2.4 MPa or 3.8 MPa. The time to failure is recorded and reported. A longer failure time correlates with a greater resistance to SCG. Generally speaking, increasing the resin density lowers the PENT failure times. The resistance to slow crack growth can be quantified as failure times (e.g., PENT failure times).

In an aspect, a high quality polyethylene resin pipe of the type disclosed herein can display a resistance to slow crack growth of greater than about 500 h, alternatively greater than about 2,000 h, or alternatively greater than about 5,000 h, wherein the resistance to slow crack growth is defined as the PENT failure time. As will be appreciated by one of skill in the art, and with the help of this disclosure, in order to meet a PE-100 grade, a PE pipe has to have a minimum PENT failure time of greater than about 5,000 h.

In an aspect, a method of determining bimodal polyethylene quality can comprise the steps of (a) providing a bimodal polyethylene resin sample; (b) determining, in one aspect in real-time or near real-time, in any sequence, at least one of the following: that the bimodal polyethylene resin sample has a melt index within 30% of a target melt index; that the bimodal polyethylene resin sample has a density within 2.5% of a target density; that the bimodal polyethylene resin sample has a % MVD from a target dynamic viscosity of less than about 100%; that the bimodal polyethylene resin sample has a % $M_wD$ from a target $M_w$ of less than about 20%; and that the bimodal polyethylene resin sample has a % GPCD from a target GPC curve profile of less than about 15%; and (c) responsive to step (b), designating the bimodal polyethylene resin sample as a high quality resin. In such aspect, the method can further comprise physically segregating the high quality resin from a low quality resin for further storage or processing; wherein the low quality resin excludes a resin having at least one property selected from the group consisting of a melt index within 30% of the target melt index, a density within 2.5% of the target density, a % MVD of less than about 100%, a % $M_wD$ of less than about 20%, a % GPCD of less than about 15%, and combinations thereof. In such aspect, the resultant high quality resin can be further formed into an article, for example a pipe or a film.

Referring to FIG. 1, a method of monitoring multimodal polyethylene quality 100 can comprise (a) a step 10 of providing a plurality of multimodal polyethylene resins; (b) a step 20 of determining a melt index of each of the plurality of multimodal polyethylene resins, wherein resins excluding a resin having a melt index within 30% of a target melt index are designated as low quality resins 25; (c) a step 30 of determining a density of each of the plurality of multimodal polyethylene resins having a melt index within 30% of the target melt index, wherein resins excluding a resin having a density within 2.5% of a target density are designated as low quality resins 35; (d) a step 40 of (d1) determining a dynamic viscosity ($\eta_s^*$) of each of the plurality of multimodal polyethylene resins having a density within 2.5% of the target density, wherein $\eta_s^*$ is determined across a range of shear rate ($\omega_i$) of from about 0.01 $s^{-1}$ to about 1,000 $s^{-1}$; and (d2) comparing the dynamic viscosity of the multimodal polyethylene resins with a target dynamic viscosity ($\eta_c^*$); wherein comparing the dynamic viscosity comprises calculating a % MVD from the target dynamic viscosity; and wherein resins having a % MVD of equal to or greater than about 100% are designated as low quality resins 45; (e) a step 50 of (e1) determining a $M_w$ of each of the plurality of multimodal polyethylene resins having a % MVD of less than about 100%, wherein $M_w$ is determined from a GPC curve profile, wherein the GPC curve profile comprises a differential weight fraction (dw/d(log M)) as a function of log M, and wherein M is the molecular weight of the weight fraction w; and (e2) comparing the $M_w$ of the multimodal polyethylene resin with a target $M_w$, wherein comparing the $M_w$ comprises calculating a %$_w$ D from the target $M_w$; and wherein resins having a %$_w$ D of equal to or greater than about 20% are designated as low quality resins 55; (f) a step 60 of comparing the GPC curve profile of each of the plurality of multimodal polyethylene resins having a %$_w$ D of less than about 20% with a target GPC curve profile;

wherein comparing the GPC curve profile comprises calculating a % GPCD from the target GPC curve profile; and wherein resins having a % GPCD of less than a first threshold (e.g., less than about 15%, alternatively less than about 12%, alternatively less than about 10%, alternatively less than about 6%, or alternatively less than about 3%) are designated as high quality resins 61 (e.g., prime lot resins); and (g) a step 62 of comparing each of the plurality of multimodal polyethylene resins having a % GPCD greater than the first threshold with a second threshold, wherein resins having a % GPCD of equal to or greater than the second threshold (e.g., equal to or greater than 6%, alternatively equal to or greater than 12%, alternatively equal to or greater than 20%, alternatively equal to or greater than 24%, or alternatively equal to or greater than 30%) are designated as low quality resins 65, and wherein resins having a % GPCD of less than the second threshold are designated as intermediate quality resins 63 (e.g., technical hold resins). The intermediate quality resins 63 can be subjected to additional testing for various properties, to determine whether the resin can be used as a high quality resin in a specific application (e.g., film manufacturing, pipe manufacturing), or if the resin has to be downgraded to low quality resin. In an aspect, the high quality resins can be physically segregated from the low quality resins for further storage or processing. In some aspects, the method can further comprise controlling one or more process parameters to alter one or more multimodal polyethylene resin properties, wherein the one or more multimodal polyethylene resin properties comprises at least one of melt index, density, dynamic viscosity, GPC curve profile, $M_w$, or combinations thereof. In such aspects, altering one or more multimodal polyethylene resin properties increases a yield of high quality resins.

In an aspect, the method of monitoring multimodal polyethylene quality described with respect to FIG. 1 can be implemented on a computer. A control scheme (e.g., a control scheme for a feed-back loop to a reaction zone; a control scheme for designating resin quality; a control scheme for physically segregating resins based on quality designations) implemented by a control system as disclosed herein can be in the form of hard coded instructions or as a software module stored in a memory and executed by a processor of a computer. Further, any of the functions described with respect to the control systems disclosed herein can be implemented on a computer or in another system as described herein.

FIG. 2 illustrates a computer system 980 suitable for implementing one or more aspects disclosed herein. The computer system 980 includes a processor 982 (which may be referred to as a central processor unit or CPU) that is in communication with memory devices including secondary storage 984, read only memory (ROM) 986, random access memory (RAM) 988, input/output (I/O) devices 990, and network connectivity devices 992. The processor 982 may be implemented as one or more CPU chips.

It is understood that by programming and/or loading executable instructions onto the computer system 980, at least one of the CPU 982, the RAM 988, and the ROM 986 are changed, transforming the computer system 980 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 984 is typically comprised of one or more disk drives or tape drives and is used for non-volatile storage of data and as an over-flow data storage device if RAM 988 is not large enough to hold all working data. Secondary storage 984 may be used to store programs which are loaded into RAM 988 when such programs are selected for execution. The ROM 986 is used to store instructions and perhaps data which are read during program execution. ROM 986 is a non-volatile memory device which typically has a small memory capacity relative to the larger memory capacity of secondary storage 984. The RAM 988 is used to store volatile data and perhaps to store instructions. Access to both ROM 986 and RAM 988 is typically faster than to secondary storage 984. The secondary storage 984, the RAM 988, and/or the ROM 986 may be referred to in some contexts as computer readable storage media and/or non-transitory computer readable media.

I/O devices 990 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 992 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 992 may enable the processor 982 to communicate with the Internet or one or more intranets. With such a network connection, it is contemplated that the processor 982 might receive information from the network, or might output information to the network in the course of performing the above-described method steps. Such information, which is often represented as a sequence of instructions to be executed using processor 982, may be received from and outputted to the network, for example, in the form of a computer data signal embodied in a carrier wave.

Such information, which may include data or instructions to be executed using processor 982 for example, may be received from and outputted to the network, for example, in the form of a computer data baseband signal or signal embodied in a carrier wave. The baseband signal or signal embodied in the carrier wave, or other types of signals currently used or hereafter developed, may be generated according to several methods well known to one skilled in the art. The baseband signal and/or signal embedded in the carrier wave may be referred to in some contexts as a transitory signal.

The processor 982 executes instructions, codes, computer programs, scripts which it accesses from hard disk, floppy disk, optical disk (these various disk based systems may all be considered secondary storage 984), ROM 986, RAM 988, or the network connectivity devices 992. While only one processor 982 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 984, for example, hard drives, floppy disks, optical disks, and/or other device, the ROM 986, and/or the RAM 988 may be referred to in some contexts as non-transitory instructions and/or non-transitory information.

In an aspect, the computer system 980 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an aspect, virtualization software may be employed by the computer system 980 to provide the functionality of a number of servers that is not directly bound to the number of computers in the computer system 980. For example, virtualization software may provide twenty virtual servers on four physical computers. In an aspect, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an aspect, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 980, at least portions of the contents of the computer program product to the secondary storage 984, to the ROM 986, to the RAM 988, and/or to other non-volatile memory and volatile memory of the computer system 980. The processor 982 may process the executable instructions and/or data structures in part by directly accessing the computer program product, for example by reading from a CD-ROM disk inserted into a disk drive peripheral of the computer system 980. Alternatively, the processor 982 may process the executable instructions and/or data structures by remotely accessing the computer program product, for example by downloading the executable instructions and/or data structures from a remote server through the network connectivity devices 992. The computer program product may comprise instructions that promote the loading and/or copying of data, data structures, files, and/or executable instructions to the secondary storage 984, to the ROM 986, to the RAM 988, and/or to other non-volatile memory and volatile memory of the computer system 980.

In some contexts, the secondary storage 984, the ROM 986, and the RAM 988 may be referred to as a non-transitory computer readable medium or a computer readable storage media. A dynamic RAM embodiment of the RAM 988, likewise, may be referred to as a non-transitory computer readable medium in that while the dynamic RAM receives electrical power and is operated in accordance with its design, for example during a period of time during which the computer 980 is turned on and operational, the dynamic RAM stores information that is written to it. Similarly, the processor 982 may comprise an internal RAM, an internal ROM, a cache memory, and/or other internal non-transitory storage blocks, sections, or components that may be referred to in some contexts as non-transitory computer readable media or computer readable storage media.

One or more of the disclosed systems, processes, or both for producing and monitoring the quality of polyolefins can advantageously display improvements in one or more system characteristics, process characteristics, or both when compared to conventional systems, processes, or both for producing and monitoring the quality of polyolefins.

In an aspect, the disclosed systems, processes, or both for producing and monitoring the quality of polyolefins can advantageously allow for the production of multimodal polyolefin resins (e.g., bimodal polyethylene resins, trimodal polyethylene resin) that also meet molecular weight distribution (MWD) targets in addition to meeting melt index and density specifications. As will be appreciated by one of skill in the art, and with the help of this disclosure, MWD profiles for various resins impact their processability and end-use applications. As such, some of the polyolefin resins quality control tools disclosed herein (e.g., % GPCD, % $M_w$D) can advantageously provide for screening resins for MWD, such that the resins can both meet melt index and density specification, and be on target for MWD. Some resins that meet conventional specifications (e.g., melt index, density), and the % MVD as disclosed herein, might not display the necessary end-use properties such as SCG properties, optical properties, processability, and the like, if they don't meet the % GPCD specification.

In an aspect, both the % MVD and % GPCD can be advantageously measured in near real-time, and as such the quality of produced resins can be advantageously used in a feedback control loop, to ensure that the produced resins meet the required specifications, for example by adjusting operational parameters. In such aspect, mis-grading resin lots, premature downgrading or upgrading of resin lots, or both can be reduced or eliminated. The correct identification of the quality of multimodal polyolefin resins is particularly important for pipe resins (e.g., bimodal pipe resins), which, if not having the required MWD profiles, can display inferior SCG resistance properties. Likewise, a subtle change in MWD profile can result in significant change in film processability, and as such a resin used for film manufacturing needs to meet the required MWD profile.

In an aspect, the disclosed systems, processes, or both for producing and monitoring the quality of polyolefins can advantageously provide for product quality consistency. Additional advantages of the systems, processes, or both for producing and monitoring the quality of polyolefins as disclosed herein can be apparent to one of skill in the art viewing this disclosure.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

EXAMPLES

The disclosure having been generally described, the following examples are given as particular embodiments of the disclosure and to demonstrate the practice and advantages thereof. It is understood that the examples are given by way of illustration and are not intended to limit the specification of the claims to follow in any manner.

Example 1

Figure 3A:
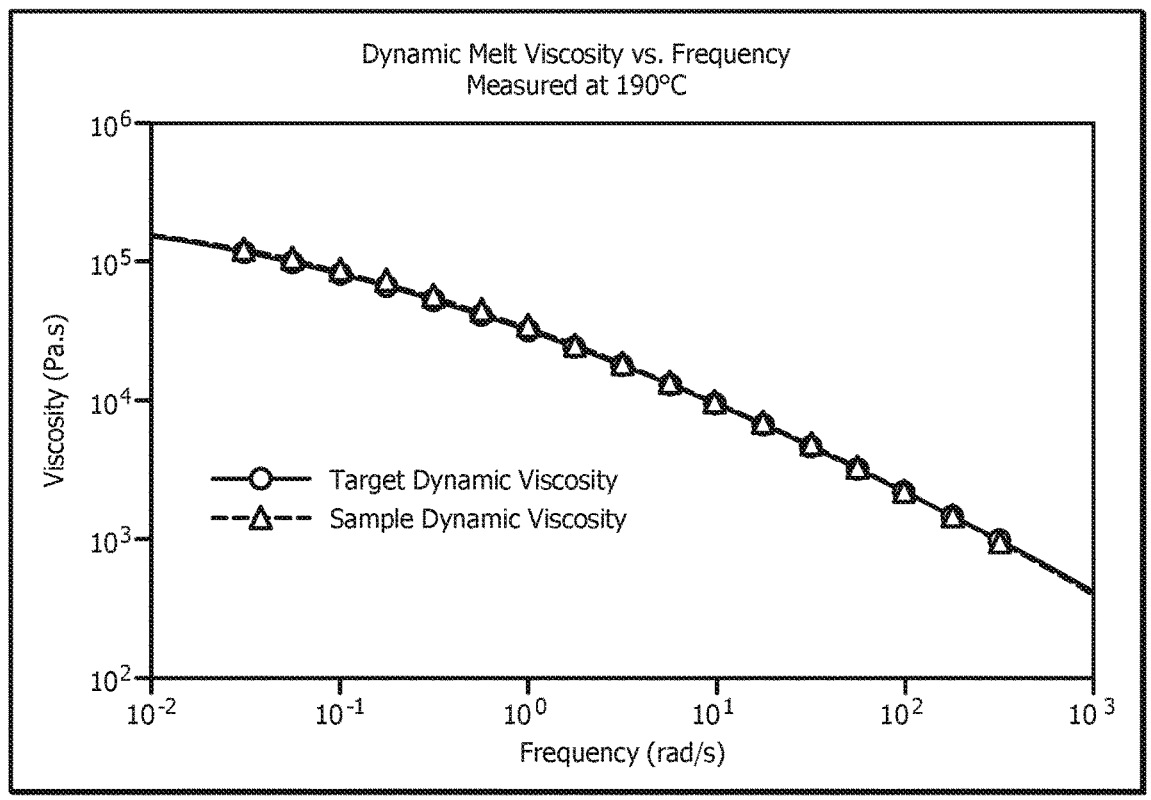
FIGS. 3A and 3B display dynamic viscosity data for a polyethylene resin and a target resin (3A); and the deviation of the dynamic viscosity from the target resin (3B)

The quality of various bimodal polyethylene resins was investigated. Specifically, the dynamic viscosity of a bimodal polyethylene sample was compared to a target dynamic viscosity, wherein the dynamic viscosity data are displayed in FIG. 3A for both the sample and the target. The dynamic viscosity was measured for both the sample resin and the target resin. A % MVD was calculated for the deviation of the sample from the target dynamic according to equation (1), and the % MVD data are displayed in FIG. 3B.

The dynamic viscosity measurements were performed as follows. The polymer samples were compression molded at 182° C. The samples were allowed to melt at a relatively low pressure for 1 min and then subjected to a high molding pressure for an additional 2 min. The molded samples were then quenched in a room temperature press, and then 25.4 mm diameter disks were stamped out of the molded sample slabs for the measurement. The dynamic frequency sweep tests were performed in parallel plates of 25 mm diameter at 190° C. using a rotational rheometer (Physica MCR-500, Anton Paar). The test chamber of the rheometer was purged with nitrogen to minimize oxidative degradation. After thermal equilibration, the specimens were squeezed between the plates to a 1.6 mm thickness, and the excess was trimmed. The dynamic frequency sweep tests were performed by applying small-strain (1~10%) oscillatory shear in the linear viscoelastic regime at angular frequencies from 0.0316 to 316 $\sec^{-1}$. The dynamic viscosity ($\eta^*$) was measured as a function of frequency ($\omega$).

Figure 3B:
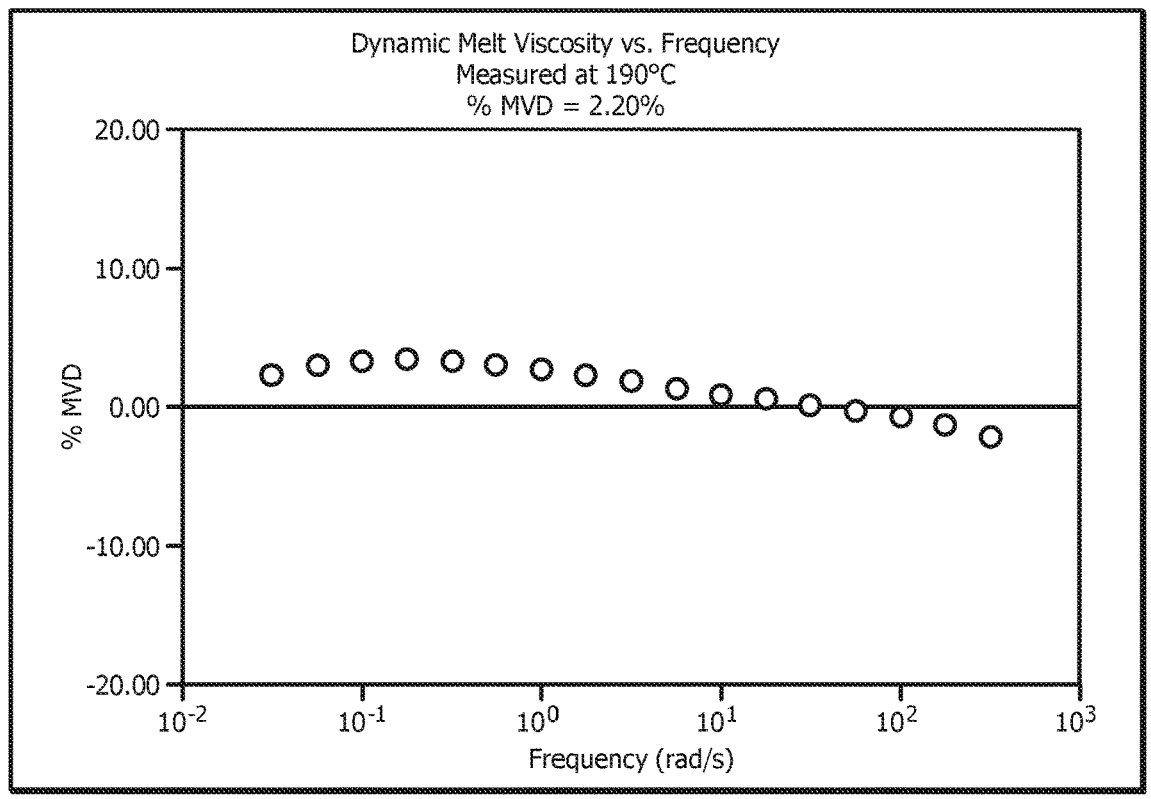

The data displayed in FIG. 3B for % MVD can inform the production process as of to what might need to be changed in terms of operational process parameters in order for the produced resin to meet the dynamic viscosity target more closely.

Example 2

The quality of various bimodal polyethylene resins was investigated. Specifically, the GPC curve profile of a bimodal polyethylene sample was compared to a target GPC curve profile, wherein the GPC curve profile data are displayed in FIG. 4 for both the sample and the target. The GPC curve profile was measured for both the sample resin and the target resin. A % GPCD was calculated for the deviation of the sample from the target GPC curve profile according to equation (2), and the % GPCD data are also displayed in FIG. 4.

Molecular weights and molecular weight distributions were obtained using a PL-220 GPC/size exclusion chromatograph (SEC) high temperature chromatography unit (Agilent, Calif.), or a GPC-QC system of Polymer Characterisation SA, Spain, with 1,2,4-trichlorobenzene (TCB) as the mobile phase at a flow rate of 1.0 or 0.7 mL/minute, respectively. For either testing system, the GPC was run at 145° C. The columns used were three (3×) Waters Styrogel 7.5 mm×300 mm HMW-6E columns (Waters, Mass.) or two (2X) Agilent 7.5 mm×150 mm. Rapide columns (Agilent, Calif.) were calibrated with the integral method using a broad linear polyethylene standard (Chevron Phillips Chemical Company Marlex® BHB 5003 polyethylene) for which the molecular weight distribution had been determined. BHT (2,6-di-tert-butyl-4-methylphenol) at a concentration of 0.5 g/L was used as a stabilizer for TCB. An injection volume of 400 µL or 150 µL, respectively, was used with a nominal polymer concentration of 1.0 mg/mL. Dissolution of the sample in stabilized TCB was carried out by heating the sample at 150° C. or 180° C. for about 5 hours, or 25 min, respectively, with gentle agitation.

Figure 4:
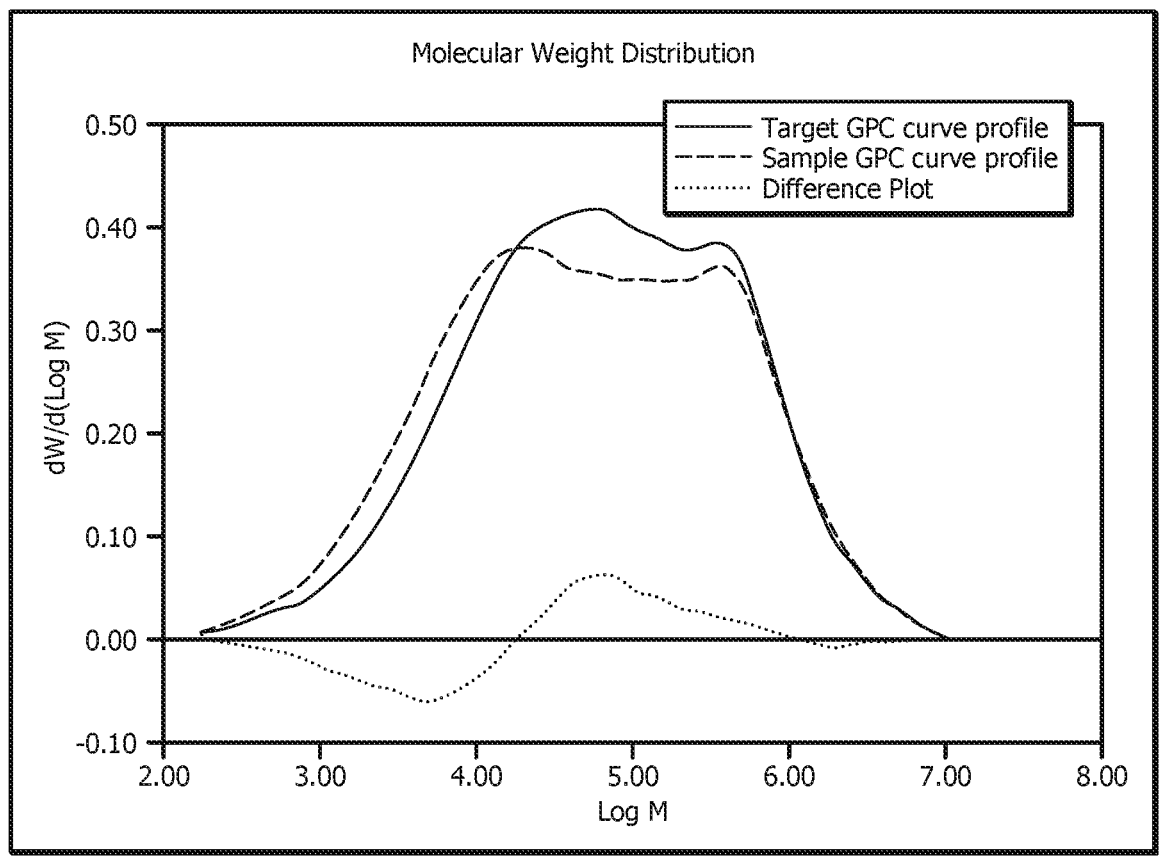
FIG. 4 displays gel permeation chromatography (GPC) curve profiles for a polyethylene resin, a target resin, and the deviation of the GPC curve profile (i.e., a difference plot) from the target resin.

The data displayed in FIG. 4 for % GPCD can inform the production process as of to what might need to be changed in terms of operational process parameters in order for the produced resin to meet the GPC curve profile target more closely.

Example 3

The quality of various bimodal polyethylene resins was investigated. Specifically, the GPC curve profile of 4 different bimodal polyethylene samples was compared to a target GPC curve profile, wherein the GPC curve profile data are displayed in each of FIGS. 5A, 5B, 5C and 5D for both the sample (sample #A, sample #B, sample #C, and sample #D, respectively) and the target. The bimodal polyethylene resin sample #A (FIG. 5A) was a bimodal pipe resin made under a first set of process conditions. The bimodal polyethylene resin sample #B (FIG. 5B) was a bimodal pipe resin made under a second set of process conditions (different from the first set of process conditions). The bimodal polyethylene resin sample #C (FIG. 5C) was a bimodal pipe resin made under a third set of process conditions (different from each of the first and the second sets of process conditions). The bimodal polyethylene resin sample #D (FIG. 5D) was a bimodal pipe resin made under a fourth set of process conditions (different from each of the first, the second, and the third sets of process conditions). The GPC curve profile was measured as described in Example 2. A % GPCD was calculated for the deviation of the sample from the target GPC curve profile according to equation (2), and the %

GPCD data are also displayed in FIGS. 5A, 5B, 5C and 5D. Samples #A, #B, #C, and #D were hourly resin samples taken from the same reactor, but produced under different operational parameters (e.g., process conditions).

Figure 5A:
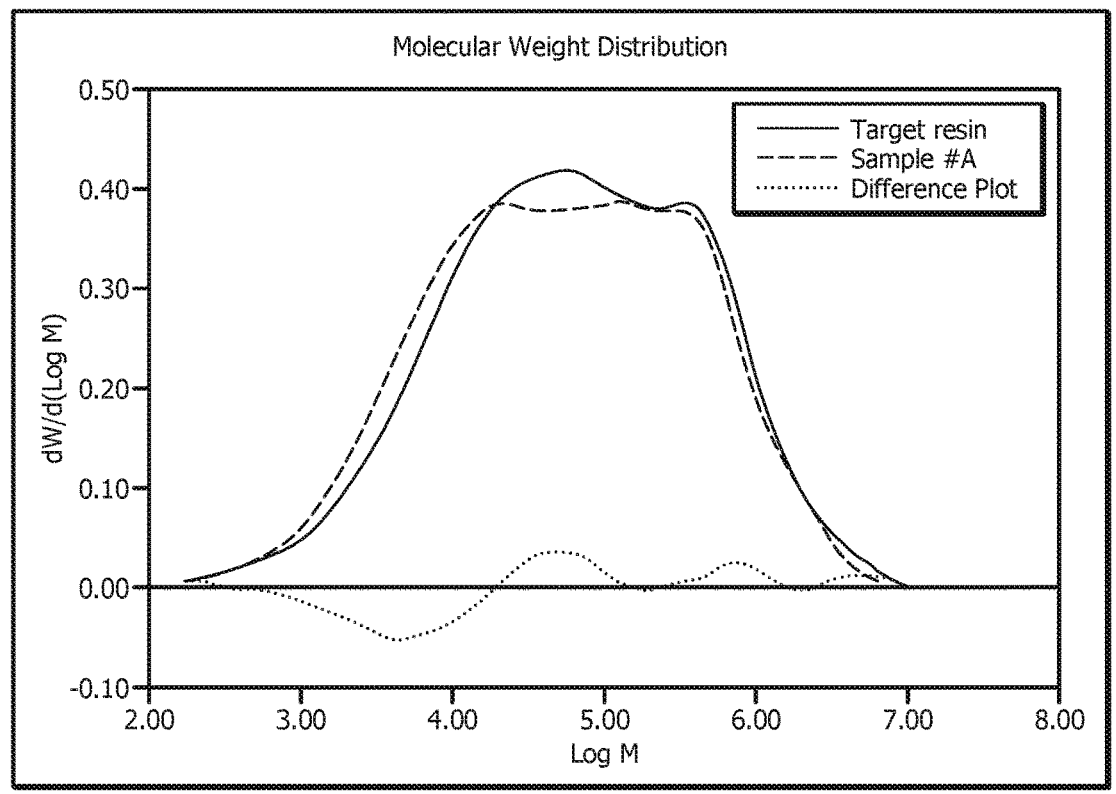
FIGS. 5A, 5B, 5C and 5D display GPC curve profiles for various polyethylene resins, a target resin, and the deviation of the GPC curve profiles from the target resin.
Figure 5B:
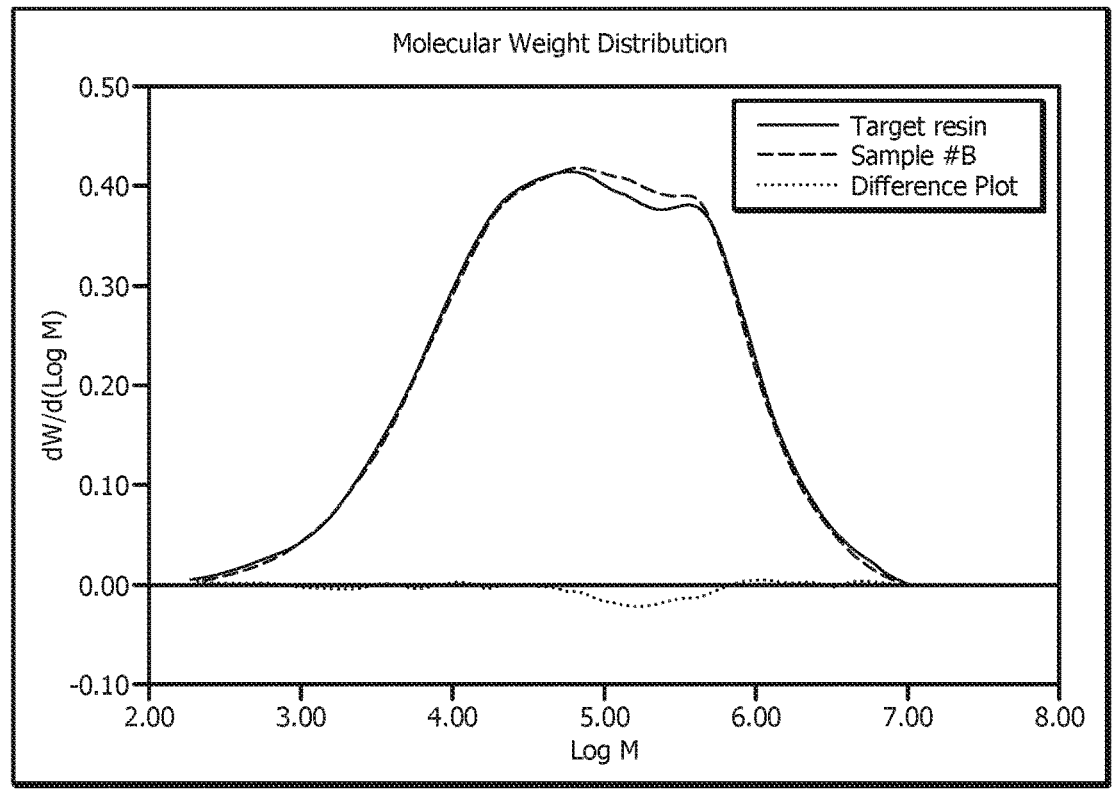
Figure 5C:
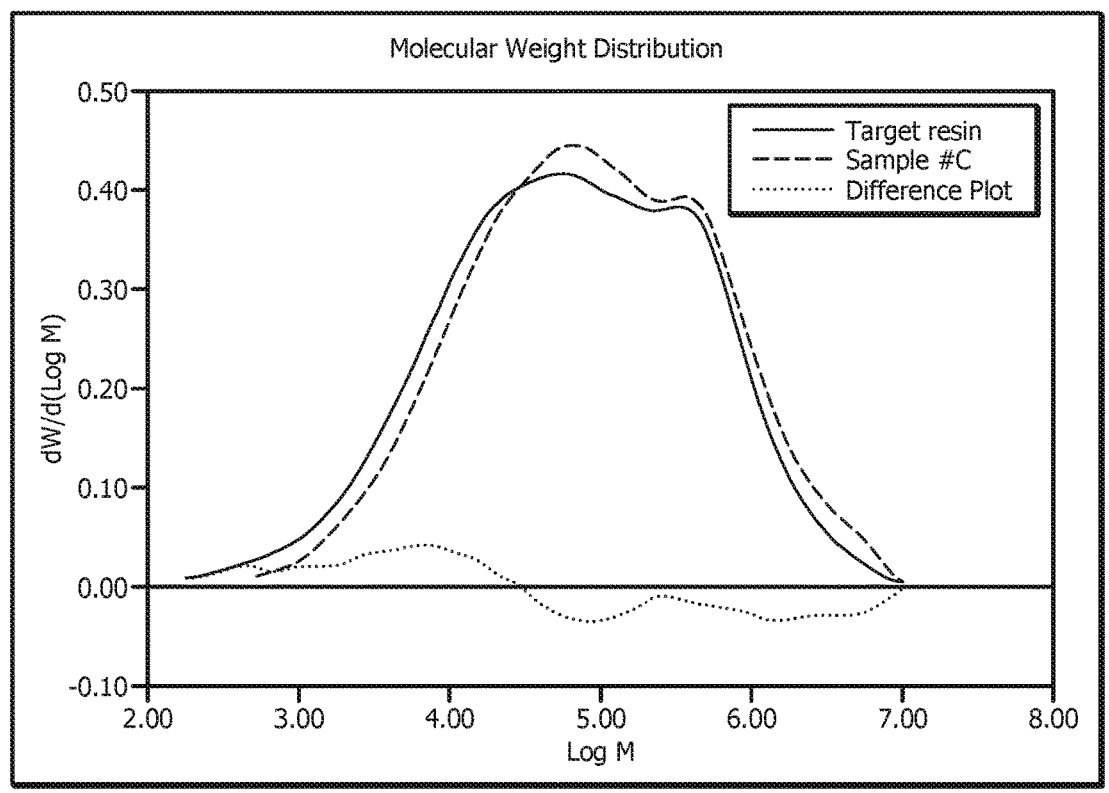
Figure 5D:
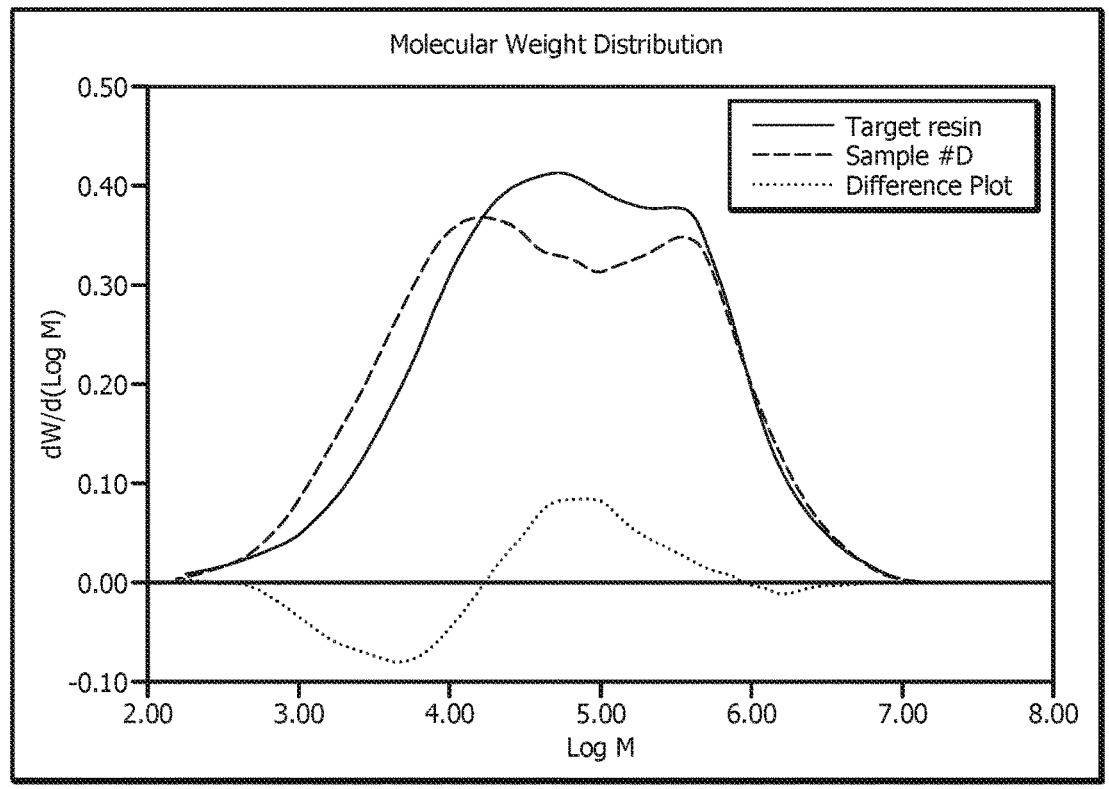

Without wishing to be limited by theory, % GPCD values can vary from 0% (i.e., sample fully matches the target) to 100% (i.e., complete mismatch between the sample and the target). The smaller the value of % GPCD, the better the match between the sample and the target. FIG. 5B displays a good match between the sample #B and the target, with a low value for % GPCD at 2.47%. FIG. 5D displays a poor match between the sample #D and the target, with a high value for % GPCD at 16.89%. FIGS. 5A and 5C displays an intermediate match (not particularly good, but not particularly poor either) between samples #A and #C, respectively, and the target, with intermediate values for % GPCD at 8.47% and 11.13%, respectively.

Example 4

The quality of various bimodal polyethylene resins was investigated. Specifically, molecular weight averages, dynamic viscosity, and GPC curve profile of various bimodal polyethylene samples were compared to the corresponding properties of a target resin, and the data are displayed in Table 1, wherein, the following constraints were applied: % MVD: 15%; % MwD: 10%; upper bound (second threshold) % GPCD: 10%; lower bound (first threshold) of % GPCD: 5%.

The resin samples (samples #1 through #24 in Table 1) were polymer fluff samples recovered from the second reactor of a dual-loop reactor. The target resin was a bimodal pipe resin.

A % MVD was calculated for the deviation of the sample from the target dynamic according to equation (1). A % GPCD was calculated for the deviation of the sample from the target GPC curve profile according to equation (2). The first threshold was set at 5% and the second threshold was set at 10%. $M_w$ was calculated according to equation (4), and % $M_wD$ was calculated according to equation (3).

The number average molecular weight is the common average of the molecular weights of the individual polymers and was calculated by measuring the molecular weight $M_i$ of $N_i$ polymer molecules, summing the weights, and dividing by the total number of polymer molecules, according to equation 5:

$$M_n = \frac{\sum_i N_i M_i}{\sum_i N_i} \tag{5}$$

wherein $N_i$ is the number of molecules of molecular weight $M_i$. The z-average molecular weight is a higher order

TABLE 1

| Sample # | Mn/1000 | Mw/1000 | Mz/1000 | Mw/Mn | IV* | % MVD | Grading Based on % MVD | % $M_wD$ | Grading based on % $M_wD$ | % GPCD | Grading based on % GPCD | Final Grade |
|---|---|---|---|---|---|---|---|---|---|---|---|---|
| Target Resin | 10.13 | 298.3 | 1805.4 | 29.45 | 2.900 | | | | | | | |
| 1 | 9.76 | 257.4 | 1357.1 | 26.37 | 2.625 | 23.8% | off | −13.73% | off | 8.47% | Tech Hold | off |
| 2 | 8.80 | 257.0 | 1480.3 | 29.21 | 2.599 | 32.2% | off | −13.84% | off | 9.51% | Tech Hold | off |
| 3 | 11.08 | 285.2 | 1649.3 | 25.74 | 2.831 | 28.0% | off | −4.41% | on | 2.47% | on | off |
| 4 | 7.13 | 247.4 | 1330.5 | 34.70 | 2.535 | 24.9% | off | −17.05% | off | 11.73% | off | off |
| 5 | 9.51 | 264.9 | 1478.0 | 27.85 | 2.672 | 20.2% | off | −11.21% | off | 6.06% | Tech Hold | off |
| 6 | 10.07 | 295.9 | 1847.9 | 29.38 | 2.873 | 9.4% | on | −0.81% | on | 2.80% | on | on |
| 7 | 10.43 | 281.2 | 1603.2 | 26.96 | 2.797 | 9.9% | on | −5.72% | on | 2.54% | on | on |
| 8 | 11.00 | 278.0 | 1496.3 | 25.28 | 2.789 | 12.9% | on | −6.80% | on | 2.53% | on | on |
| 9 | 10.28 | 266.1 | 1411.3 | 25.88 | 2.706 | 15.8% | off | −10.81% | off | 3.18% | on | off |
| 10 | 9.52 | 269.0 | 1490.6 | 28.25 | 2.712 | 12.9% | on | −9.84% | on | 3.19% | on | on |
| 11 | 9.41 | 298.5 | 1892.1 | 31.72 | 2.873 | 6.4% | on | 0.05% | on | 5.64% | Tech Hold | Tech Hold |
| 12 | 7.08 | 282.7 | 1736.2 | 39.94 | 2.751 | 5.9% | on | −5.22% | on | 11.63% | off | off |
| 13 | 8.78 | 286.1 | 1706.7 | 32.58 | 2.793 | 8.8% | on | −4.10% | on | 7.73% | Tech Hold | Tech Hold |
| 14 | 8.61 | 301.1 | 1792.4 | 34.97 | 2.897 | 5.4% | on | 0.92% | on | 7.79% | Tech Hold | Tech Hold |
| 15 | 17.67 | 386.6 | 2301.2 | 21.88 | 3.493 | 55.6% | off | 29.61% | off | 11.13% | off | off |
| 16 | 8.00 | 295.6 | 1900.1 | 36.95 | 2.826 | 9.4% | on | −0.91% | on | 11.94% | off | off |
| 17 | 7.62 | 303.3 | 2061.4 | 39.81 | 2.850 | 7.9% | on | 1.69% | on | 16.89% | off | off |
| 18 | 6.84 | 294.8 | 1909.7 | 43.11 | 2.799 | 8.3% | on | −1.16% | on | 16.01% | off | off |
| 19 | 10.29 | 341.5 | 2157.4 | 33.19 | 3.142 | 7.2% | on | 14.50% | off | 9.15% | Tech Hold | off |
| 20 | 11.06 | 348.1 | 2310.8 | 31.48 | 3.178 | 19.6% | off | 16.70% | off | 8.15% | Tech Hold | off |
| 21 | 9.73 | 337.64 | 2258.3 | 34.70 | 3.092 | 11.4% | on | 13.19% | off | 11.46% | off | off |
| 22 | 7.84 | 343.13 | 2255.9 | 43.77 | 3.114 | 12.4% | on | 15.03% | off | 15.71% | off | off |
| 23 | 15.83 | 358.88 | 2110.3 | 22.67 | 3.328 | 25.1% | off | 20.31% | off | 8.68% | Tech Hold | off |
| 24 | 7.65 | 307.07 | 1908.7 | 40.14 | 2.892 | 7.6% | on | 2.94% | on | 16.32% | off | off |

*IV = Intrinsic Viscosity [g/dL]; off = off-spec; on = on-spec; tech hold = technical hold.

molecular weight average which was calculated according to equation 6:

$$M_z = \frac{\sum_i N_i M_i^3}{\sum_i N_i M_i^2} \quad (6)$$

wherein $N_i$ is the number of molecules of molecular weight $M_i$.

The molecular weight distribution was calculated as the ratio of the $M_w$ to the $M_n$ ($M_w/M_n$), which can also be referred to as the polydispersity index (PDI) or more simply as polydispersity.

The data in Table 1 indicate that some resin lots (samples) met both $M_w$ and % MVD, but failed to meet % GPCD specifications, and therefore were downgraded (samples #12, #16, #17, #18, and #24). Some other samples that had % GPCD values that fell between the first threshold and the second threshold were placed on technical hold, subject to further testing before a grading could be assigned (samples #11, #13, and #14). As it can be seen from the data in Table 1, rapid GPC parameters clearly help to proper grade (e.g., monitor the quality of) resins, thus reducing premature upgrading or downgrading of the resins.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

ADDITIONAL DISCLOSURE

The following enumerated embodiments are provided as nonlimiting examples.

A first aspect which is a method of producing polyethylene comprising (a) polymerizing ethylene in one or more reaction zones to produce a first polyethylene resin, wherein each reaction zone of the one or more reaction zones operates independently at a first value for a plurality of parameters, and wherein each parameter of the plurality of parameters is selected from the group consisting of ethylene concentration, comonomer concentration, hydrogen to ethylene ratio, temperature, catalyst concentration, cocatalyst concentration, pressure, and residence time; (b) determining a dynamic viscosity ($\eta_s^*$) of the first polyethylene resin; (c) comparing the dynamic viscosity of the first polyethylene resin with a target dynamic viscosity ($\eta_c^*$), wherein comparing the dynamic viscosity comprises calculating a dynamic viscosity deviation (% MVD) from the target dynamic viscosity, and wherein the first polyethylene resin is characterized by a % MVD of equal to or greater than about 100%; (d) selecting a second value for one or more parameters of the plurality of parameters for at least one of the one or more reaction zones, wherein the second value decreases the % MVD of the polyethylene resin; (e) operating the at least one of the one or more reaction zones independently at the second value of the one or more parameters of the plurality of parameters; and (f) recovering a second polyethylene resin from the one or more reaction zones, wherein the second polyethylene resin is characterized by a % MVD of less than about 100%.

A second aspect which is the method of the first aspect further comprising repeating steps (b) through (e) until the second polyethylene resin is characterized by a % MVD of less than about 15%.

A third aspect which is the method of any one of the first and the second aspects, wherein the dynamic viscosity is determined across a range of shear rate ($\omega_i$) of from about 0.01 $s^{-1}$ to about 1,000 $s^{-1}$.

A fourth aspect which is the method of any one of the first through the third aspects, wherein the first polyethylene resin is characterized by a melt index that is within 30% of a target melt index, and wherein the second polyethylene resin is characterized by a melt index that is within 30% of the target melt index.

A fifth aspect which is the method of the fourth aspect, wherein the target melt index is from about 5 g/10 min to about 25 g/10 min, as determined under a force of 21.6 kg in accordance with ASTM D1238.

A sixth aspect which is the method of any one of the first through the fourth aspects, wherein the target melt index is from about 0.001 g/10 min to about 0.25 g/10 min, as determined under a force of 2.16 kg in accordance with ASTM D1238.

A seventh aspect which is the method of any one of the first through the sixth aspects, wherein the first polyethylene resin is characterized by a density that is within 2.5% of a target density, and wherein the second polyethylene resin is characterized by a density that is within 2.5% of the target density.

An eighth aspect which is the method of any one of the first through the seventh aspects, wherein the polyethylene resin is a multimodal resin.

A ninth aspect which is the method of any one of the first through the eighth aspects, wherein the polyethylene resin is a bimodal resin.

A tenth aspect which is the method of the ninth aspect, wherein the bimodal resin has a higher molecular weight (HMW) component and a lower molecular weight (LMW) component, wherein the HMW component is present in an amount of from about 35 wt. % to about 65 wt. %, and wherein the LMW component is present in an amount of from about 65 wt. % to about 35 wt. %.

An eleventh aspect which is the method of any one of the first through the tenth aspects, wherein % MVD is calculated using the following equation:

$$\% \ MVD = 100 \times \sqrt{\frac{\sum_i \left[\frac{(\eta_s^*)_{\omega_i} - (\eta_c^*)_{\omega_i}}{(\eta_c^*)_{\omega_i}}\right]^2}{i}},$$

wherein $(\eta_s^*)_{\omega_i}$ is the dynamic viscosity of the polyethylene resin at a shear rate $\omega_i$, wherein $(\eta_c^*)_{\omega_i}$ is the target dynamic viscosity at the shear rate $\omega_i$, wherein i represents the number of data points collected for the dynamic viscosity ($\eta_s^*$) across the range of shear rate ($\omega_i$), and wherein i is equal to or greater than 3.

A twelfth aspect which is the method of any one of the first through the eleventh aspects, wherein the second polyethylene resin is characterized by a % MVD of less than about 50%.

A thirteenth aspect which is the method of any one of the first through the twelfth aspects further comprising (i) determining a gel permeation chromatography (GPC) curve profile of the second polyethylene resin; wherein the GPC curve profile comprises a differential weight fraction (dw/d(log M)) as a function of log M, wherein M is the molecular weight of the weight fraction w; and (ii) comparing the GPC curve profile of the second polyethylene resin with a target GPC curve profile, wherein comparing the GPC curve profile comprises calculating a GPC curve profile deviation (% GPCD) from the target GPC curve profile.

A fourteenth aspect which is the method of any one of the first through the thirteenth aspects, wherein the second polyethylene resin is characterized by a % GPCD of equal to or greater than about 15%, and wherein the second polyethylene resin is designated as a low quality resin.

A fifteenth aspect which is the method of any one of the first through the thirteenth aspects, wherein the second polyethylene resin is characterized by a % GPCD of less than about 15%, and wherein the second polyethylene resin is designated as a high quality resin.

A sixteenth aspect which is the method of the fifteenth aspect further comprising forming the second polyethylene resin into a pipe or a film.

A seventeenth aspect which is the method of any one of the first through the sixteenth aspects, wherein % GPCD is calculated using the following equation:

$$\% \ GPCD = 100 \times \sum_{j} \text{Abs}\left[\left(\frac{dw}{d(\text{Log } M)}\right)_{P,j} - \left(\frac{dw}{d(\text{Log } M)}\right)_{T,j}\right] * d(\text{Log } M)_j,$$

wherein $$\left(\frac{dw}{d(\text{Log} M)}\right)_{P,j}$$

is the differential weight fraction of the polyethylene for a fraction j of the polyethylene molecules having the molecular weight M, and wherein $$\left(\frac{dw}{d(\text{Log} M)}\right)_{T,j}$$

is the target differential weight fraction for the fraction j of the polyethylene molecules.

An eighteenth aspect which is the method of any one of the first through the seventeenth aspects, wherein the one or more reaction zones comprise a single reactor.

A nineteenth aspect which is the method of any one of the first through the eighteenth aspects, wherein the one or more reaction zones comprise two reactors in series.

A twentieth aspect which is the method of any one of the first through the nineteenth aspects, wherein the comonomer comprises 1-hexene.

A twenty-first aspect which is a method of producing polyethylene comprising (a) polymerizing ethylene in one or more reaction zones to produce a first polyethylene resin, wherein each reaction zone of the one or more reaction zones operates independently at a first value for a plurality of parameters, and wherein each parameter of the plurality of parameters is selected from the group consisting of ethylene concentration, comonomer concentration, hydrogen to ethylene ratio, temperature, catalyst concentration, cocatalyst concentration, pressure, and residence time; (b) determining a gel permeation chromatography (GPC) curve profile of the first polyethylene resin; wherein the GPC curve profile comprises a differential weight fraction (dw/d(log M)) as a function of log M, wherein M is the molecular weight of the weight fraction w; (c) comparing the GPC curve profile of the first polyethylene resin with a target GPC curve profile, wherein comparing the GPC curve profile comprises calculating a GPC curve profile deviation (% GPCD) from the target GPC curve profile, and wherein the first polyethylene resin is characterized by a % GPCD of equal to or greater than about 15%; (d) selecting a second value for one or more parameters of the plurality of parameters for at least one of the one or more reaction zones, wherein the second value decreases the % GPCD of the polyethylene resin; (e) operating the at least one of the one or more reaction zones independently at the second value of the one or more parameters of the plurality of parameters; and (e) recovering a second polyethylene resin from the one or more reaction zones, wherein the second polyethylene resin is characterized by a % GPCD of less than about 15%.

A twenty-second aspect which is the method of the twenty-first aspect, wherein the first polyethylene resin is characterized by a melt index that is within 30% of a target melt index; wherein the second polyethylene resin is characterized by a melt index that is within 30% of the target melt index; wherein the first polyethylene resin is characterized by a density that is within 2.5% of a target density; and wherein the second polyethylene resin is characterized by a density that is within 2.5% of a target density.

A twenty-third aspect which is the method of any one of the twenty-first and the twenty-second aspects, wherein the second polyethylene resin is characterized by a % GPCD of less than about 5%.

A twenty-fourth aspect which is the method of any one of the twenty-first through the twenty-third aspects further comprising (i) determining a dynamic viscosity ($\eta_s^*$) of the second polyethylene resin across a range of shear rate ($\omega_i$) of from about 0.01 s$^{-1}$ to about 1,000 s$^{-1}$, and (ii) comparing the dynamic viscosity of the second polyethylene resin with a target dynamic viscosity ($\eta_c^*$), wherein comparing the dynamic viscosity comprises calculating a dynamic viscosity deviation (% MVD) from the target dynamic viscosity.

A twenty-fifth aspect, which is the method of the twenty-fourth aspect, wherein, when the second polyethylene resin is characterized by a % MVD of equal to or greater than about 100%, the second polyethylene resin is designated as a low quality resin; and wherein, when the second polyethylene resin is characterized by a % MVD of less than about 100%, the second polyethylene resin is designated as a high quality resin.

A twenty-sixth aspect, which is the method of the twenty-fifth aspect, wherein the second polyethylene resin is a bimodal resin.

A twenty-seventh aspect, which is the method of the twenty-sixth aspect further comprising forming the high quality resin into a pipe or a film.

A twenty-eighth aspect, which is a method of producing polyethylene comprising (a) polymerizing ethylene in one or more reaction zones to produce a first polyethylene resin, wherein each reaction zone of the one or more reaction zones operates independently at a first value for a plurality of parameters, and wherein each parameter of the plurality of parameters is selected from the group consisting of ethylene concentration, comonomer concentration, hydrogen to ethylene ratio, temperature, catalyst concentration, cocatalyst concentration, pressure, and residence time; (b) determining a dynamic viscosity ($\eta_s^*$) of the first polyethylene resin; (c) determining a gel permeation chromatography (GPC) curve profile of the first polyethylene resin; wherein the GPC curve profile comprises a differential weight fraction (dw/d(log M)) as a function of log M, wherein M is the molecular weight of the weight fraction w; (d) comparing the dynamic viscosity of the first polyethylene resin with a target dynamic viscosity ($\eta_c^*$) and the GPC curve profile of the first polyethylene resin with a target GPC curve profile; wherein comparing the dynamic viscosity comprises calculating a dynamic viscosity deviation (% MVD) from the target dynamic viscosity; wherein comparing the GPC curve profile comprises calculating a GPC curve profile deviation (% GPCD) from the target GPC curve profile; and wherein the first polyethylene resin is characterized by a % MVD of equal to or greater than about 100%, by a % GPCD of equal to or greater than about 15%, or by both a % MVD of equal to or greater than about 100% and a % GPCD of equal to or greater than about 15%; (e) selecting a second value for one or more parameters of the plurality of parameters for at least one of the one or more reaction zones; wherein, when the first polyethylene resin is characterized by a % MVD of equal to or greater than about 100%, the second value decreases the % MVD of the polyethylene resin; wherein, when the first polyethylene resin is characterized by a % GPCD of equal to or greater than about 15%, the second value decreases the % GPCD of the polyethylene resin; and wherein, when the first polyethylene resin is characterized by both a % MVD of equal to or greater than about 100% and a % GPCD of equal to or greater than about 15%, the second value decreases both the % MVD and the % GPCD of the polyethylene resin; (f) operating the at least one of the one or more reaction zones independently at the second value of the one or more parameters of the plurality of parameters; and (g) recovering a second polyethylene resin from the one or more reaction zones, wherein the second polyethylene resin is characterized by both a % MVD of less than about 100% and a % GPCD of less than about 15%.

A twenty-ninth aspect, which is the method of the twenty-eighth aspect, wherein the dynamic viscosity is determined across a range of shear rate ($\omega_i$) of from about 0.01 s$^{-1}$ to about 1,000 s$^{-1}$.

A thirtieth aspect, which is the method of any one of the twenty-eighth and the twenty-ninth aspects, wherein the first polyethylene resin is characterized by a melt index that is within 30% of a target melt index; wherein the second polyethylene resin is characterized by a melt index that is within 30% of the target melt index; wherein the first polyethylene resin is characterized by a density that is within 2.5% of a target density; and wherein the second polyethylene resin is characterized by a density that is within 2.5% of the target density.

A thirty-first aspect, which is the method of any one of the twenty-eighth through the thirtieth aspects further comprising (i) determining the weight average molecular weight ($M_w$) of the polyethylene resin from the GPC curve profile, and (ii) comparing the $M_w$ of the polyethylene resin with a target $M_w$, wherein comparing the $M_w$ comprises calculating a $M_w$ deviation (% $M_wD$) from the target $M_w$.

A thirty-second aspect, which is the method of the thirty-first aspect, wherein the first polyethylene resin is characterized by a % $M_wD$ of equal to or greater than about 20%; and wherein the second value decreases the % $M_wD$ of the polyethylene resin.

A thirty-third aspect, which is the method of any one of the twenty-eighth through the thirty-second aspects, wherein the second polyethylene resin is characterized by a % $M_wD$ of less than about 20%.

A thirty-fourth aspect, which is the method of any one of the twenty-eighth through the thirty-third aspects, wherein the second polyethylene resin is characterized by a % $M_wD$ of less than about 5%.

A thirty-fifth aspect, which is the method of any one of the twenty-eighth through the thirty-fourth aspects, wherein % $M_wD$ is calculated using the following equation:

$$\% M_wD = 100 \times \mathrm{Abs}((M_{w,T} - M_{w,P})/M_{w,T})$$

wherein $M_{w,T}$ is the weight average molecular weight ($M_w$) of the target, and wherein $M_{w,P}$ is the $M_w$ of the product.

A thirty-sixth aspect, which is the method of any one of the twenty-eighth through the thirty-fifth aspects, wherein the second polyethylene resin is a bimodal resin.

A thirty-seventh aspect, which is the method of the thirty-sixth aspect further comprising forming the second polyethylene resin into a pipe or a film.

A thirty-eighth aspect, which is a system for producing polyethylene comprising one or more polymerization reaction zones configured to produce a polyethylene resin, wherein each reaction zone of the one or more reaction zones operates independently at a plurality of parameters, and wherein each parameter of the plurality of parameters is selected from the group consisting of ethylene concentration, comonomer concentration, hydrogen to ethylene ratio, temperature, catalyst concentration, cocatalyst concentration, pressure, and residence time;

a testing system configured to characterize the polyethylene resin for one or more resin properties, wherein the one or more resin properties comprises at least one of dynamic viscosity, gel permeation chromatography (GPC) curve profile, weight average molecular weight ($M_w$), or combinations thereof; and a control system configured to receive the one or more resin properties from the testing system, wherein the control system comprises at least one processor and at least one controller; wherein the at least one processor compares the one or more resin properties with corresponding target properties; wherein the at least one processor, when at least one of the one or more resin properties is different when compared to the corresponding target property, signals the at least one controller; and wherein the at least one controller adjusts at least one of the plurality of parameters independently for at least one reaction zone of the one or more reaction zones.

A thirty-ninth aspect, which is the system of the thirty-eighth aspect, wherein the one or more resin properties further comprises density, melt index, or both density and melt index.

A fortieth aspect, which is the system of any one of the thirty-eighth and the thirty-ninth aspects, wherein the control system is a distributed control system.

A forty-first aspect, which is the system of any one of the thirty-eighth through the fortieth aspects, wherein the at least one processor compares the dynamic viscosity of the polyethylene resin with a target dynamic viscosity ($\eta_c^*$); wherein comparing the dynamic viscosity comprises calculating a dynamic viscosity deviation (% MVD) from the target dynamic viscosity; and wherein % MVD is calculated using the following equation:

$$\% MVD = 100 \times \sqrt{\frac{\sum_i \left[\frac{(\eta_s^*)_{\omega_i} - (\eta_c^*)_{\omega_i}}{(\eta_c^*)_{\omega_i}}\right]^2}{i}},$$

wherein $(\eta_s^*)_{\omega_i}$ is the dynamic viscosity of the polyethylene resin at a shear rate $\omega_i$, wherein $(\eta_c^*)_{\omega_i}$ is the target dynamic viscosity at the shear rate $\omega_i$, wherein i represents the number of data points collected for the dynamic viscosity $(\eta_s^*)$ across the range of shear rate $(\omega_i)$, and wherein i is equal to or greater than 3.

A forty-second aspect, which is the system of any one of the thirty-eighth through the forty-first aspects, wherein the dynamic viscosity of the polyethylene resin is different from the target dynamic viscosity $(\eta_c^*)$ when % MVD is equal to or greater than about 100%.

A forty-third aspect, which is the system of any one of the thirty-eighth through the forty-second aspects, wherein the at least one processor compares the GPC curve profile of the polyethylene resin with a target GPC curve profile; wherein comparing the GPC curve profile comprises calculating a GPC curve profile deviation (% GPCD) from the target GPC curve profile; and wherein % GPCD is calculated using the following equation:

$$\% GPCD = 100 \times \sum_j \text{Abs}\left(\left(\frac{dw}{d(\log M)}\right)_{P,j} - \left(\frac{dw}{d(\log M)}\right)_{T,j}\right) * d(\log M)_j,$$

wherein $$\left(\frac{dw}{d(\log M)}\right)_{P,j}$$

is the differential weight fraction of the polyethylene for a fraction j of the polyethylene molecules having the molecular weight M, and wherein $$\left(\frac{dw}{d(\log M)}\right)_{T,j}$$

is the target differential weight fraction for the fraction j of the polyethylene molecules.

A forty-fourth aspect, which is the system of any one of the thirty-eighth through the forty-third aspects, wherein the GPC curve profile of the polyethylene resin is different from the target GPC curve profile when % GPCD is equal to or greater than about 15%.

A forty-fifth aspect, which is the system of any one of the thirty-eighth through the forty-fourth aspects, wherein the at least one processor compares the $M_w$ of the polyethylene resin with a target $M_w$; wherein comparing the $M_w$ comprises calculating a $M_w$ deviation (% $M_wD$) from the target $M_w$; and wherein % $M_wD$ is calculated using the following equation:

$$\% M_wD = 100 \times \text{Abs}((M_{w,T} - M_{w,P})/M_{w,T})$$

wherein $M_{w,T}$ is the weight average molecular weight ($M_w$) of the target, and wherein $M_{w,P}$ is the $M_w$ of the product.

A forty-sixth aspect, which is the system of any one of the thirty-eighth through the forty-fifth aspects, wherein the $M_w$ of the polyethylene resin is different from the target $M_w$ when % $M_wD$ is equal to or greater than about 20%.

A forty-seventh aspect, which is the system of any one of the thirty-eighth through the forty-sixth aspects, wherein the control system provides for near real-time feedback to the one or more reaction zones.

A forty-eighth aspect, which is a method of processing polyethylene comprising (a) providing a plurality of polyethylene resins; (b) determining a dynamic viscosity $(\eta_s^*)$ of each of the plurality of polyethylene resins; (c) comparing the dynamic viscosity of each of the plurality of polyethylene resins with a target dynamic viscosity $(\eta_c^*)$, wherein comparing the dynamic viscosity comprises calculating a dynamic viscosity deviation (% MVD) from the target dynamic viscosity; (d) selecting one or more polyethylene resins from the plurality of polyethylene resins to yield selected polyethylene, wherein the selected polyethylene is characterized by a % MVD of less than about 100%; and (e) processing the selected polyethylene via a shaping process to produced shaped polyethylene.

A forty-ninth aspect, which is the method of the forty-eighth aspect, wherein the dynamic viscosity is determined across a range of shear rate $(\omega_i)$ of from about 0.01 s$^{-1}$ to about 1,000 s$^{-1}$.

A fiftieth aspect, which is the method of any one of the forty-eighth and the forty-ninth aspects, wherein each of the plurality of polyethylene resins is individually characterized by a melt index that is within 30% of a target melt index; and wherein each of the plurality of polyethylene resins is individually characterized by a density that is within 2.5% of a target density.

A fifty-first aspect, which is the method of any one of the forty-eighth through the fiftieth aspects, wherein the step (e) of processing the selected polyethylene comprises forming the selected polyethylene into a pipe or a film, wherein the selected polyethylene is a bimodal resin.

A fifty-second aspect, which is the method of any one of the forty-eighth through the fifty-first aspects, wherein the selected polyethylene, when tested in accordance with ASTM F1473, has a resistance to slow crack growth of greater than about 500 h, wherein the resistance to slow crack growth is defined as the PENT failure time.

A fifty-third aspect, which is the method of any one of the forty-eighth through the fifty-second aspects, wherein % MVD is calculated using the following equation:

$$\% MVD = 100 \times \sqrt{\frac{\sum_i \left[\frac{(\eta_s^*)_{\omega_i} - (\eta_c^*)_{\omega_i}}{(\eta_c^*)_{\omega_i}}\right]^2}{i}},$$

wherein $(\eta_s^*)_{\omega_i}$ is the dynamic viscosity of the polyethylene resin at a shear rate $\omega_i$, wherein $(\eta_c^*)_{\omega_i}$ is the target dynamic viscosity at the shear rate $\omega_i$, wherein i represents the number of data points collected for the dynamic viscosity $(\eta_s^*)$ across the range of shear rate $(\omega_i)$, and wherein i is equal to or greater than 3.

A fifty-fourth aspect, which is a method of processing polyethylene comprising (a) providing a plurality of polyethylene resins; (b) determining a gel permeation chromatography (GPC) curve profile of each of the plurality of polyethylene resins; wherein the GPC curve profile comprises a differential weight fraction (dw/d(log M)) as a function of log M, wherein M is the molecular weight of the weight fraction w; (c) comparing the GPC curve profile of each of the plurality of polyethylene resins with a target GPC curve profile, wherein comparing the GPC curve profile comprises calculating a GPC curve profile deviation (% GPCD) from the target GPC curve profile; (d) selecting one or more polyethylene resins from the plurality of polyethylene resins to yield selected polyethylene, wherein the selected polyethylene is characterized by a % GPCD of less than about 15%; and (e) processing the selected polyethylene via a shaping process to produced shaped polyethylene.

A fifty-fifth aspect, which is the method of the fifty-fourth aspect, wherein each of the plurality of polyethylene resins is individually characterized by a melt index that is within 30% of a target melt index, and wherein each of the plurality of polyethylene resins is individually characterized by a density that is within 2.5% of a target density.

A fifty-sixth aspect, which is the method of any one of the fifty-fourth and the fifty-fifth aspects, wherein the selected polyethylene is a bimodal resin, and wherein the step (e) of processing the selected polyethylene comprises forming the selected polyethylene into a pipe or a film.

A fifty-seventh aspect, which is the method of any one of the fifty-fourth through the fifty-sixth aspects, wherein % GPCD is calculated using the following equation:

$$\% GPCD = 100 \times \sum_j \text{Abs}\left(\left(\frac{dw}{d(\text{Log} M)}\right)_{P,j} - \left(\frac{dw}{d(\text{Log} M)}\right)_{T,j}\right) * d(\text{Log} M)_j,$$

wherein $$\left(\frac{dw}{d(\text{Log} M)}\right)_{P,j}$$

is the differential weight fraction of the polyethylene for a fraction j of the polyethylene molecules having the molecular weight M, and wherein $$\left(\frac{dw}{d(\text{Log} M)}\right)_{T,j}$$

is the target differential weight fraction for the fraction j of the polyethylene molecules.

A fifty-eighth aspect, which is a method of processing polyethylene comprising (a) providing a plurality of polyethylene resins; (b) determining a dynamic viscosity ($\eta_s^*$) of each of the plurality of polyethylene resins; (c) determining a gel permeation chromatography (GPC) curve profile of each of the plurality of polyethylene resins; wherein the GPC curve profile comprises a differential weight fraction (dw/d(log M)) as a function of log M, wherein M is the molecular weight of the weight fraction w; (d) comparing the dynamic viscosity of each of the plurality of polyethylene resins with a target dynamic viscosity ($\eta_c^*$) and the GPC curve profile of each of the plurality of polyethylene resins with a target GPC curve profile; wherein comparing the dynamic viscosity comprises calculating a dynamic viscosity deviation (% MVD) from the target dynamic viscosity; and wherein comparing the GPC curve profile comprises calculating a GPC curve profile deviation (% GPCD) from the target GPC curve profile; (e) selecting one or more polyethylene resins from the plurality of polyethylene resins to yield selected polyethylene, wherein the selected polyethylene is characterized by a % MVD of less than about 100% and a % GPCD of less than about 15%; and (f) processing the selected polyethylene via a shaping process to produced shaped polyethylene.

A fifty-ninth aspect, which is the method of the fifty-eighth aspect, wherein the dynamic viscosity is determined across a range of shear rate ($\omega_i$) of from about 0.01 s$^{-1}$ to about 1,000 s$^{-1}$.

A sixtieth aspect, which is the method of any one of the fifty-eighth and the fifty-ninth aspects, wherein each of the plurality of polyethylene resins is individually characterized by a melt index that is within 30% of a target melt index, and wherein each of the plurality of polyethylene resins is individually characterized by a density that is within 2.5% of a target density.

A sixty-first aspect, which is the method of any one of the fifty-eighth through the sixtieth aspects, wherein the step (f) of processing the selected polyethylene comprises forming the selected polyethylene into a pipe or a film, and wherein the selected polyethylene is a bimodal resin.

A sixty-second aspect, which is the method of any one of the fifty-eighth through the sixty-first aspects further comprising (i) determining the weight average molecular weight ($M_w$) of each of the plurality of polyethylene resins from the GPC curve profile, and (ii) comparing the $M_w$ of each of the plurality of polyethylene resins with a target $M_w$, wherein comparing the $M_w$ comprises calculating a $M_w$ deviation (% $M_wD$) from the target $M_w$.

A sixty-third aspect, which is the method of the sixty-second aspect, wherein the selected polyethylene is characterized by a % $M_wD$ of less than about 20%.

A sixty-fourth aspect, which is the method of any one of the fifty-eighth through the sixty-third aspects, wherein % $M_wD$ is calculated using the following equation:

$$\% M_wD = 100 \times \text{Abs}((M_{w,T} - M_{w,P})/M_{w,T})$$

wherein $M_{w,T}$ is the weight average molecular weight ($M_w$) of the target, and wherein $M_{w,P}$ is the $M_w$ of the product.

A sixty-fifth aspect, which is a system for processing polyethylene comprising a testing system configured to characterize a plurality of polyethylene resins for one or more resin properties, wherein the one or more resin properties comprises at least one of dynamic viscosity, gel permeation chromatography (GPC) curve profile, weight average molecular weight ($M_w$), or combinations thereof; a computer system configured to receive the one or more resin properties from the testing system, wherein the computer system comprises at least one processor; wherein the at least one processor compares the one or more resin properties with corresponding target properties; wherein the at least one processor, when at least one of the one or more resin properties is different when compared to the corresponding target property, designates the resin as low quality resin; wherein the at least one processor, when the one or more resin properties are the same when compared to the corresponding target properties, designates the resin as selected polyethylene; and a shaping system configured to receive the selected polyethylene and process the selected polyethylene into a shaped article.

A sixty-sixth aspect, which is the system of the sixty-fifth aspect, wherein the one or more resin properties further comprises density, melt index, or both density and melt index.

A sixty-seventh aspect, which is the system of any one of the sixty-fifth and the sixty-sixth aspects, wherein the at least one processor compares the dynamic viscosity of each of the plurality of polyethylene resins with a target dynamic viscosity ($\eta_c^*$); wherein comparing the dynamic viscosity comprises calculating a dynamic viscosity deviation (% MVD) from the target dynamic viscosity; and wherein % MVD is calculated using the following equation:

$$\% MVD = 100 \times \sqrt{\frac{\sum_i \left[\frac{(\eta_s^*)_{\omega_i} - (\eta_c^*)_{\omega_i}}{(\eta_c^*)_{\omega_i}}\right]^2}{i}},$$

wherein $(\eta_s^*)_{\omega_i}$ is the dynamic viscosity of the polyethylene resin at a shear rate $\omega_i$, wherein $(\eta_c^*)_{\omega_i}$ is the target dynamic viscosity at the shear rate $\omega_i$, wherein i represents the number of data points collected for the dynamic viscosity ($\eta_s^*$) across the range of shear rate ($\omega_i$), and wherein i is equal to or greater than 3.

A sixty-eighth aspect, which is the system of the sixty-seventh aspect, wherein the dynamic viscosity of the polyethylene resin is the same as the target dynamic viscosity ($\eta_c^*$) when % MVD is less than about 100%.

A sixty-ninth aspect, which is the system of any one of the sixty-fifth through the sixty-eighth aspects, wherein the at least one processor compares the GPC curve profile of each of the plurality of polyethylene resins with a target GPC curve profile; wherein comparing the GPC curve profile comprises calculating a GPC curve profile deviation (% GPCD) from the target GPC curve profile; and wherein % GPCD is calculated using the following equation:

$$\% GPCD = 100 \times \sum_j \text{Abs}\left(\left(\frac{dw}{d(\text{Log}M)}\right)_{P,j} - \left(\frac{dw}{d(\text{Log}M)}\right)_{T,j}\right) * d(\text{Log}M)_j,$$

wherein $$\left(\frac{dw}{d(\text{Log}M)}\right)_{P,j}$$

is the differential weight fraction of the polyethylene for a fraction j of the polyethylene molecules having the molecular weight M, and wherein $$\left(\frac{dw}{d(\text{Log}M)}\right)_{T,j}$$

is the target differential weight fraction for the fraction j of the polyethylene molecules.

A seventieth aspect, which is the system of the sixty-ninth aspect, wherein the GPC curve profile of the polyethylene resin is the same as the target GPC curve profile when % GPCD is less than about 15%.

A seventy-first aspect, which is the system of any one of the sixty-fifth through the seventieth aspects, wherein the at least one processor compares the $M_w$ of each of the plurality of polyethylene resins with a target $M_w$; wherein comparing the $M_w$ comprises calculating a $M_w$ deviation (% $M_wD$) from the target $M_w$; and wherein % $M_wD$ is calculated using the following equation:

$$\% M_wD = 100 \times \text{Abs}((M_{w,T} - M_{w,P})/M_{w,T})$$

wherein $M_{w,T}$ is the weight average molecular weight ($M_w$) of the target, and wherein $M_{w,P}$ is the $M_w$ of the product.

A seventy-second aspect, which is the system of the seventy-first aspect, wherein the $M_w$ of the polyethylene resin is the same as the target $M_w$ when % $M_wD$ is less than about 20%.

A seventy-third aspect, which is the system of any one of the sixty-fifth through the seventy-second aspects, wherein the selected polyethylene is a bimodal resin, and wherein the shaped article is a pipe or a film.

A seventy-fourth aspect, which is a method of monitoring multimodal polyethylene quality comprising (a) providing a plurality of multimodal polyethylene resins; (b) determining a dynamic viscosity ($\eta_s^*$) of each of the plurality of multimodal polyethylene resins; (c) comparing the dynamic viscosity of each of the plurality of multimodal polyethylene resins with a target dynamic viscosity ($\eta_c^*$), wherein comparing the dynamic viscosity comprises calculating a dynamic viscosity deviation (% MVD) from the target dynamic viscosity; (d) selecting one or more multimodal polyethylene resins from the plurality of multimodal polyethylene resins to yield a first multimodal polyethylene resin, wherein the first multimodal polyethylene resin is characterized by a % MVD of equal to or greater than about 100%, and wherein the first multimodal polyethylene resin is designated as a low quality resin; (e) selecting one or more multimodal polyethylene resins from the plurality of multimodal polyethylene resins to yield a second multimodal polyethylene resin, wherein the second multimodal polyethylene resin is characterized by a % MVD of less than about 100%, and wherein the second multimodal polyethylene resin is designated as a high quality resin; and (f) physically segregating the first multimodal polyethylene resin from the second multimodal polyethylene resin for further storage or processing.

A seventy-fifth aspect, which is the method of the seventy-fourth aspect, wherein the dynamic viscosity is determined across a range of shear rate ($\omega_i$) of from about 0.01 $s^{-1}$ to about 1,000 $s^{-1}$.

A seventy-sixth aspect, which is the method of any one of the seventy-fourth and the seventy-fifth aspects, wherein each of the plurality of multimodal polyethylene resins is individually characterized by a melt index that is within 30% of a target melt index; and wherein each of the plurality of multimodal polyethylene resins is individually characterized by a density that is within 2.5% of a target density.

A seventy-seventh aspect, which is the method of any one of the seventy-fourth through the seventy-sixth aspects, wherein the multimodal polyethylene resins are bimodal resins.

A seventy-eighth aspect, which is the method of any one of the seventy-fourth through the seventy-seventh aspects further comprising forming each of the first multimodal polyethylene resin and the second multimodal polyethylene resin into pellets subsequent to step (f) of physically segregating the first multimodal polyethylene resin from the second multimodal polyethylene resin.

A seventy-ninth aspect, which is the method of any one of the seventy-fourth through the seventy-eighth aspects further comprising processing the second multimodal polyethylene resin via a shaping process to produced shaped polyethylene subsequent to step (f) of physically segregating the first multimodal polyethylene resin from the second multimodal polyethylene resin.

An eightieth aspect, which is the method of the seventy-ninth aspect, wherein processing the second multimodal polyethylene resin comprises forming the second multimodal polyethylene resin into a pipe or a film.

An eighty-first aspect, which is the method of any one of the seventy-fourth through the eightieth aspects, wherein % MVD is calculated using the following equation:

$$\% MVD = 100 \times \sqrt{\frac{\sum_i \left[\frac{(\eta_s^*)_{\omega_i} - (\eta_c^*)_{\omega_i}}{(\eta_c^*)_{\omega_i}}\right]^2}{i}},$$

wherein $(\eta_s^*)_{\omega_i}$ is the dynamic viscosity of the polyethylene resin at a shear rate $\omega_i$, wherein $(\eta_c^*)_{\omega_i}$ is the target dynamic viscosity at the shear rate $\omega_i$, wherein i represents the number of data points collected for the dynamic viscosity $(\eta_s^*)$ across the range of shear rate $(\omega_i)$, and wherein i is equal to or greater than 3.

An eighty-second aspect, which is a method of monitoring multimodal polyethylene quality comprising (a) providing a plurality of multimodal polyethylene resins; (b) determining a gel permeation chromatography (GPC) curve profile of each of the plurality of polyethylene resins; wherein the GPC curve profile comprises a differential weight fraction (dw/d(log M)) as a function of log M, wherein M is the molecular weight of the weight fraction w; (c) comparing the GPC curve profile of each of the plurality of polyethylene resins with a target GPC curve profile, wherein comparing the GPC curve profile comprises calculating a GPC curve profile deviation (% GPCD) from the target GPC curve profile; (d) selecting one or more multimodal polyethylene resins from the plurality of multimodal polyethylene resins to yield a first multimodal polyethylene resin, wherein the first multimodal polyethylene resin is characterized by a % GPCD of equal to or greater than about 15%, and wherein the first multimodal polyethylene resin is designated as a low quality resin; (e) selecting one or more multimodal polyethylene resins from the plurality of multimodal polyethylene resins to yield a second multimodal polyethylene resin, wherein the second multimodal polyethylene resin is characterized by a % GPCD of less than about 15%, and wherein the second multimodal polyethylene resin is designated as a high quality resin; and (f) physically segregating the first multimodal polyethylene resin from the second multimodal polyethylene resin for further storage or processing.

An eighty-third aspect, which is the method of the eighty-second aspect, wherein each of the plurality of multimodal polyethylene resins is individually characterized by a melt index that is within 30% of a target melt index, and wherein each of the plurality of multimodal polyethylene resins is individually characterized by a density that is within 2.5% of a target density.

An eighty-fourth aspect, which is the method of any one of the eighty-second and the eighty-third aspects, wherein % GPCD is calculated using the following equation:

$$\% GPCD = 100 \times \sum_j \text{Abs}\left(\left(\frac{dw}{d(\text{Log } M)}\right)_{P,j} - \left(\frac{dw}{d(\text{Log } M)}\right)_{T,j}\right) * d(\text{Log } M)_j,$$

wherein $$\left(\frac{dw}{d(\text{Log } M)}\right)_{P,j}$$

is the differential weight fraction of the polyethylene for a fraction j of the polyethylene molecules having the molecular weight M, and wherein $$\left(\frac{dw}{d(\text{Log } M)}\right)_{T,j}$$

is the target differential weight fraction for the fraction j of the polyethylene molecules.

An eighty-fifth aspect, which is a method of monitoring multimodal polyethylene quality comprising (a) providing a plurality of multimodal polyethylene resins; (b) determining a dynamic viscosity $(\eta_s^*)$ of each of the plurality of multimodal polyethylene resins; (c) determining a gel permeation chromatography (GPC) curve profile of each of the plurality of polyethylene resins; wherein the GPC curve profile comprises a differential weight fraction (dw/d(log M)) as a function of log M, wherein M is the molecular weight of the weight fraction w; (d) comparing the dynamic viscosity of each of the plurality of multimodal polyethylene resins with a target dynamic viscosity $(\eta_c^*)$ and the GPC curve profile of each of the plurality of polyethylene resins with a target GPC curve profile, wherein comparing the dynamic viscosity comprises calculating a dynamic viscosity deviation (% MVD) from the target dynamic viscosity, and wherein comparing the GPC curve profile comprises calculating a GPC curve profile deviation (% GPCD) from the target GPC curve profile; (e) selecting one or more multimodal polyethylene resins from the plurality of multimodal polyethylene resins to yield a first multimodal polyethylene resin; wherein the first multimodal polyethylene resin is characterized by a % MVD of equal to or greater than about 100%, a % GPCD of equal to or greater than about 15%, or both a % MVD of equal to or greater than about 100% and a % GPCD of equal to or greater than about 15%; and wherein the first multimodal polyethylene resin is designated as a low quality resin; (f) selecting one or more multimodal polyethylene resins from the plurality of multimodal polyethylene resins to yield a second multimodal polyethylene resin, wherein the second multimodal polyethylene resin is characterized by both a % MVD of less than about 100% and a % GPCD of less than about 15%, and wherein the second multimodal polyethylene resin is designated as a high quality resin; and (g) physically segregating the first multimodal polyethylene resin from the second multimodal polyethylene resin for further storage or processing.

An eighty-sixth aspect, which is the method of the eighty-fifth aspect, wherein the dynamic viscosity is determined across a range of shear rate ($\omega_i$) of from about 0.01 s$^{-1}$ to about 1,000 s$^{-1}$.

An eighty-seventh aspect, which is the method of any one of the eighty-fifth and the eighty-sixth aspects, wherein each of the plurality of multimodal polyethylene resins is individually characterized by a melt index that is within 30% of a target melt index, and wherein each of the plurality of multimodal polyethylene resins is individually characterized by a density that is within 2.5% of a target density.

An eighty-eighth aspect, which is the method of any one of the eighty-fifth through the eighty-seventh aspects further comprising (i) determining the weight average molecular weight ($M_w$) of each of the plurality of multimodal polyethylene resins from the GPC curve profile, and (ii) comparing the $M_w$ of each of the plurality of multimodal polyethylene resins with a target $M_w$, wherein comparing the $M_w$ comprises calculating a $M_w$ deviation (% $M_wD$) from the target $M_w$, wherein % $M_w$ D is calculated using the following equation:

$$\% M_wD = 100 \times \text{Abs}((M_{w,T} - M_{w,P})/M_{w,T})$$

wherein $M_{w,T}$ is the weight average molecular weight ($M_w$) of the target, and wherein $M_{w,P}$ is the $M_w$ of the product.

An eighty-ninth aspect, which is the method of the eighty-eighth aspect, wherein the second multimodal polyethylene resin is a bimodal resin characterized by a % $M_w$ D of less than about 20%.

A ninetieth aspect, which is a system for monitoring multimodal polyethylene quality comprising a testing system configured to characterize a plurality of multimodal polyethylene resins for one or more resin properties, wherein the one or more resin properties comprises at least one of dynamic viscosity, gel permeation chromatography (GPC) curve profile, weight average molecular weight ($M_w$), or combinations thereof; a computer system configured to receive the one or more resin properties from the testing system, wherein the computer system comprises at least one processor; wherein the at least one processor compares the one or more resin properties with corresponding target properties; wherein the at least one processor, when at least one of the one or more resin properties is different when compared to the corresponding target property, designates the resin as low quality resin; wherein the at least one processor, when the one or more resin properties are the same when compared to the corresponding target properties, designates the resin as high quality resin; and a sorting system configured to receive quality resin designations from the computer system, wherein the sorting system physically segregates the low quality resin from the high quality resin for further storage or processing.

A ninety-first aspect, which is the system of the ninetieth aspect, wherein the one or more resin properties further comprises density, melt index, or both density and melt index.

A ninety-second aspect, which is the system of any one of the ninetieth and the ninety-first aspects, wherein the at least one processor compares the dynamic viscosity of each of the plurality of multimodal polyethylene resins with a target dynamic viscosity ($\eta_c^*$); wherein comparing the dynamic viscosity comprises calculating a dynamic viscosity deviation (% MVD) from the target dynamic viscosity; and wherein % MVD is calculated using the following equation:

$$\% \ MVD = 100 \times \sqrt{\frac{\sum_i \left[\frac{(\eta_s^*)_{\omega_i} - (\eta_c^*)_{\omega_i}}{(\eta_c^*)_{\omega_i}}\right]^2}{i}},$$

wherein $(\eta_s^*)_{\omega_i}$ is the dynamic viscosity of the polyethylene resin at a shear rate $\omega_i$, wherein $(\eta_c^*)_{\omega_i}$ is the target dynamic viscosity at the shear rate $\omega_i$, wherein i represents the number of data points collected for the dynamic viscosity ($\eta_s^*$) across the range of shear rate ($\omega_i$), and wherein i is equal to or greater than 3.

A ninety-third aspect, which is the system of any one of the ninetieth through the ninety-second aspects, wherein the dynamic viscosity of the multimodal polyethylene resin is the same as the target dynamic viscosity ($\eta_c^*$) when % MVD is less than about 100%.

A ninety-fourth aspect, which is the system of any one of the ninetieth through the ninety-third aspects, wherein the at least one processor compares the GPC curve profile of each of the plurality of multimodal polyethylene resins with a target GPC curve profile; wherein comparing the GPC curve profile comprises calculating a GPC curve profile deviation (% GPCD) from the target GPC curve profile; and wherein % GPCD is calculated using the following equation:

$$\% \ GPCD = 100 \times \sum_j \text{Abs}\left(\left(\frac{dw}{d(\text{Log } M)}\right)_{P,j} - \left(\frac{dw}{d(\text{Log } M)}\right)_{T,j}\right) * d(\text{Log } M)_j,$$

wherein $$\left(\frac{dw}{d(\text{Log } M)}\right)_{P,j}$$

is the differential weight fraction of the polyethylene for a fraction j of the polyethylene molecules having the molecular weight M, and wherein $$\left(\frac{dw}{d(\text{Log } M)}\right)_{T,j}$$

is the target differential weight fraction for the fraction j of the polyethylene molecules.

A ninety-fifth aspect, which is the system of the ninety-fourth aspect, wherein the GPC curve profile of the multimodal polyethylene resin is the same as the target GPC curve profile when % GPCD is less than about 15%.

A ninety-sixth aspect, which is the system of any one of the ninetieth through the ninety-fifth aspects, wherein the at least one processor compares the $M_w$ of each of the plurality of multimodal polyethylene resins with a target $M_w$; wherein comparing the $M_w$ comprises calculating a $M_w$ deviation (% $M_wD$) from the target $M_w$; and wherein % $M_wD$ is calculated using the following equation:

$$\% M_wD = 100 \times Abs((M_{w,T} - M_{w,P})/M_{w,T})$$

wherein $M_{w,T}$ is the weight average molecular weight ($M_w$) of the target, and wherein $M_{w,P}$ is the $M_w$ of the product.

A ninety-seventh aspect, which is the system of the ninety-sixth aspect, wherein the $M_w$ of the multimodal polyethylene resin is the same as the target $M_w$ when % $M_wD$ is less than about 20%.

A ninety-eighth aspect, which is a method of monitoring multimodal polyethylene quality comprising (a) providing a plurality of multimodal polyethylene resins; (b) determining a melt index of each of the plurality of multimodal polyethylene resins, wherein resins excluding a resin having a melt index within 30% of a target melt index are designated as low quality resins; (c) determining a density of each of the plurality of multimodal polyethylene resins having a melt index within 30% of the target melt index, wherein resins excluding a resin having a density within 2.5% of a target density are designated as low quality resins; (d) determining a dynamic viscosity ($\eta_s^*$) of each of the plurality of multimodal polyethylene resins having a density within 2.5% of the target density; (e) comparing the dynamic viscosity of the multimodal polyethylene resins with a target dynamic viscosity ($\eta_c^*$); wherein comparing the dynamic viscosity comprises calculating a dynamic viscosity deviation (% MVD) from the target dynamic viscosity; and wherein resins having a % MVD of equal to or greater than about 100% are designated as low quality resins; (f) determining a weight average molecular weight ($M_w$) of each of the plurality of multimodal polyethylene resins having a % MVD of less than about 100%, wherein $M_w$ is determined from a gel permeation chromatography (GPC) curve profile, wherein the GPC curve profile comprises a differential weight fraction (dw/d(log M)) as a function of log M, and wherein M is the molecular weight of the weight fraction w; (g) comparing the $M_w$ of the multimodal polyethylene resin with a target $M_w$ wherein comparing the $M_w$ comprises calculating a $M_w$ deviation (% $M_wD$) from the target $M_w$; and wherein resins having a % $M_wD$ of equal to or greater than about 20% are designated as low quality resins; (h) comparing the GPC curve profile of each of the plurality of multimodal polyethylene resins having a % $M_wD$ of less than about 20% with a target GPC curve profile; wherein comparing the GPC curve profile comprises calculating a GPC curve profile deviation (% GPCD) from the target GPC curve profile; wherein resins having a % GPCD of equal to or greater than about 15% are designated as low quality resins; and wherein resins having a % GPCD of less than about 15% are designated as high quality resins; and (i) physically segregating the high quality resins from the low quality resins for further storage or processing.

A ninety-ninth aspect, which is the method of the ninety-eighth aspect, wherein the dynamic viscosity is determined across a range of shear rate ($\omega_i$) of from about 0.01 s$^{-1}$ to about 1,000 s$^{-1}$.

A hundredth aspect, which is the method of any one of the ninety-eighth and the ninety-ninth aspects further comprising controlling one or more process parameters to alter one or more multimodal polyethylene resin properties, wherein the one or more multimodal polyethylene resin properties comprises at least one of melt index, density, dynamic viscosity, GPC curve profile, $M_w$, or combinations thereof.

A hundred-and-first aspect, which is the method of the hundredth aspect, wherein altering one or more multimodal polyethylene resin properties increases a yield of high quality resins.

A hundred-and-second aspect, which is a method of determining multimodal polyethylene quality comprising (a) providing a multimodal polyethylene resin sample; (b) determining, in any sequence, at least one of the following: that the multimodal polyethylene resin sample has a melt index within 30% of a target melt index; that the multimodal polyethylene resin sample has a density within 2.5% of a target density; that the multimodal polyethylene resin sample has a dynamic viscosity deviation (% MVD) from a target dynamic viscosity of less than about 100%; that the multimodal polyethylene resin sample has a weight average molecular weight ($M_w$) deviation (% $M_wD$) from a target $M_w$ of less than about 20%; and that the multimodal polyethylene resin sample has a gel permeation chromatography (GPC) curve profile deviation (% GPCD) from a target GPC curve profile of less than about 15%; and (c) responsive to step (b), designating the multimodal polyethylene resin sample as a high quality resin.

A hundred-and-third aspect, which is the method of the hundred-and-second aspect further comprising physically segregating the high quality resin from a low quality resin for further storage or processing; wherein the low quality resin excludes a resin having at least one property selected from the group consisting of a melt index within 30% of the target melt index, a density within 2.5% of the target density, a % MVD of less than about 100%, a % $M_wD$ of less than about 20%, a % GPCD of less than about 15%, and combinations thereof.

A hundred-and-fourth aspect, which is the method of the hundred-and-second and the hundred-and-third aspects, wherein step (b) of determining is performed in real-time or near real-time.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, and the like; greater than 0.10 includes 0.11, 0.12, 0.13, and the like). For example, whenever a numerical range with a lower limit, $R_l$, and an upper limit, $R_u$, is disclosed, any number falling within the range is specifically disclosed. In particular, the following numbers within the range are specifically disclosed: $R = R_l + k^*(R_u - R_l)$, wherein k is a variable ranging from 1 percent to 100 percent with a 1 percent increment, i.e., k is 1 percent, 2 percent, 3 percent, 4 percent, 5 percent, 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method of producing polyethylene comprising:
   (a) polymerizing ethylene in one or more reaction zones to produce a first polyethylene resin, wherein the first polyethylene resin is a first multimodal resin, wherein each reaction zone of the one or more reaction zones operates independently at a first value for a plurality of parameters, wherein each parameter of the plurality of parameters is selected from the group consisting of ethylene concentration, comonomer concentration, hydrogen to ethylene ratio, temperature, catalyst concentration, cocatalyst concentration, pressure, and residence time, wherein the first polyethylene resin is characterized by a first melt index that is within 30% of a target melt index, and wherein the first polyethylene resin is characterized by a first density that is within 2.5% of a target density;
   (b) determining a dynamic viscosity ($\eta_s^*$) of the first polyethylene resin;
   (c) comparing the dynamic viscosity of the first polyethylene resin with a target dynamic viscosity ($\eta_c^*$), wherein comparing the dynamic viscosity comprises calculating a first dynamic viscosity deviation (a first % MVD) from the target dynamic viscosity, and wherein the first polyethylene resin is characterized by the first % MVD of equal to or greater than about 100%;
   (d) selecting a second value for one or more parameters of the plurality of parameters for at least one of the one or more reaction zones based on the first % MVD being equal to or greater than about 100%;
   (e) operating the at least one of the one or more reaction zones independently at the second value of the one or more parameters of the plurality of parameters to produce a second polyethylene resin that is a second multimodal resin, wherein the second polyethylene resin is characterized by a second % MVD of less than about 100%, a second melt index that is within 30% of the target melt index, and a second density that is within 2.5% of the target density; and
   (f) recovering the second polyethylene resin from the one or more reaction zones.

2. The method of claim 1, wherein the dynamic viscosity is determined across a range of shear rate ($\omega_i$) of from about 0.01 s$^{-1}$ to about 1,000 s$^{-1}$.

3. The method of claim 1, wherein the second polyethylene resin is a bimodal resin.

4. The method of claim 1, wherein the first % MVD or the second % MVD is calculated using the following equation:

$$\% \ MVD = 100 \times \sqrt{\frac{\sum_i \left[\frac{(\eta_s^*)_{\omega_i} - (\eta_c^*)_{\omega_i}}{(\eta_c^*)_{\omega_i}}\right]^2}{i}},$$

wherein $(\eta_s^*)_{\omega_i}$ is the dynamic viscosity of the corresponding polyethylene resin at a shear rate $\omega_i$, wherein $(\eta_c^*)_{\omega_i}$ is the target dynamic viscosity at the shear rate $\omega_i$, wherein i represents the number of data points collected for the dynamic viscosity ($\eta_s^*$) across the range of shear rate ($\omega_i$), and wherein i is equal to or greater than 3.

5. The method of claim 1 further comprising (i) determining a gel permeation chromatography (GPC) curve profile of the second polyethylene resin; wherein the GPC curve profile comprises a differential weight fraction (dw/d(log M)) as a function of log M, wherein M is the molecular weight of the weight fraction w; and (ii) comparing the GPC curve profile of the second polyethylene resin with a target GPC curve profile, wherein comparing the GPC curve profile comprises calculating a GPC curve profile deviation (% GPCD) from the target GPC curve profile.

6. The method of claim 5, wherein, when the second polyethylene resin is characterized by a % GPCD of equal to or greater than about 15%, the second polyethylene resin is designated as a low quality resin; and wherein, when the second polyethylene resin is characterized by a % GPCD of less than about 15%, the second polyethylene resin is designated as a high quality resin.

7. The method of claim 5, wherein % GPCD is calculated using the following equation:

$$\% \ GPCD = 100 \times \sum_j \text{Abs}\left(\left(\frac{dw}{d(\text{Log } M)}\right)_{P,j} - \left(\frac{dw}{d(\text{Log } M)}\right)_{T,j}\right) * d(\text{Log } M)_j,$$

wherein $$\left(\frac{dw}{d(\text{Log } M)}\right)_{P,j}$$

is the differential weight fraction of the second polyethylene resin for a fraction j of the polyethylene molecules having the molecular weight M, and wherein $$\left(\frac{dw}{d(\text{Log } M)}\right)_{T,j}$$

is the target differential weight fraction for the fraction j of the polyethylene molecules.

8. A method of producing polyethylene comprising:
   (a) polymerizing ethylene in one or more reaction zones to produce a first polyethylene resin, wherein the first polyethylene resin is a first multimodal resin, wherein each reaction zone of the one or more reaction zones operates independently at a first value for a plurality of parameters, wherein each parameter of the plurality of parameters is selected from the group consisting of ethylene concentration, comonomer concentration, hydrogen to ethylene ratio, temperature, catalyst concentration, cocatalyst concentration, pressure, and residence time, wherein the first polyethylene resin is characterized by a first melt index that is within 30% of a target melt index, and wherein the first polyethylene resin is characterized by a first density that is within 2.5% of a target density;

(b) determining a gel permeation chromatography (GPC) curve profile of the first polyethylene resin; wherein the GPC curve profile comprises a differential weight fraction (dw/d(log M)) as a function of log M, wherein M is the molecular weight of the weight fraction w;

(c) comparing the GPC curve profile of the first polyethylene resin with a target GPC curve profile, wherein comparing the GPC curve profile comprises calculating a first GPC curve profile deviation (a first % GPCD) from the target GPC curve profile, and wherein the first polyethylene resin is characterized by the first % GPCD of equal to or greater than about 15%;

(d) selecting a second value for one or more parameters of the plurality of parameters for at least one of the one or more reaction zones based on the first % GPCD being equal to or greater than about 15%;

(e) operating the at least one of the one or more reaction zones independently at the second value of the one or more parameters of the plurality of parameters to produce a second polyethylene resin that is a second multimodal resin, wherein the second polyethylene resin is characterized by a second % GPCD of less than about 15%, a second melt index that is within 30% of the target melt index, and a second density that is within 2.5% of the target density; and (f) recovering the second polyethylene resin from the one or more reaction zones.

9. The method of claim 8 further comprising (i) determining a dynamic viscosity ($\eta_s^*$) of the second polyethylene resin across a range of shear rate ($\omega_i$) of from about 0.01 s$^{-1}$ to about 1,000 s$^{-1}$, and (ii) comparing the dynamic viscosity of the second polyethylene resin with a target dynamic viscosity ($\eta_c^*$), wherein comparing the dynamic viscosity comprises calculating a dynamic viscosity deviation (% MVD) from the target dynamic viscosity.

10. The method of claim 9, wherein, when the second polyethylene resin is characterized by a % MVD of equal to or greater than about 100%, the second polyethylene resin is designated as a low quality resin; and wherein, when the second polyethylene resin is characterized by a % MVD of less than about 100%, the second polyethylene resin is designated as a high quality resin.

11. A method of producing polyethylene comprising:
(a) polymerizing ethylene in one or more reaction zones to produce a first polyethylene resin, wherein the first polyethylene resin is a first multimodal resin, wherein each reaction zone of the one or more reaction zones operates independently at a first value for a plurality of parameters, wherein each parameter of the plurality of parameters is selected from the group consisting of ethylene concentration, comonomer concentration, hydrogen to ethylene ratio, temperature, catalyst concentration, cocatalyst concentration, pressure, and residence time, wherein the first polyethylene resin is characterized by a first melt index that is within 30% of a target melt index, and wherein the first polyethylene resin is characterized by a first density that is within 2.5% of a target density;

(b) determining a dynamic viscosity ($\eta_s^*$) of the first polyethylene resin;

(c) determining a gel permeation chromatography (GPC) curve profile of the first polyethylene resin; wherein the GPC curve profile comprises a differential weight fraction (dw/d(log M)) as a function of log M, wherein M is the molecular weight of the weight fraction w;

(d) comparing the dynamic viscosity of the first polyethylene resin with a target dynamic viscosity ($\eta_c^*$) and the GPC curve profile of the first polyethylene resin with a target GPC curve profile; wherein comparing the dynamic viscosity comprises calculating a first dynamic viscosity deviation (% MVD) from the target dynamic viscosity; wherein comparing the GPC curve profile comprises calculating a first GPC curve profile deviation (% GPCD) from the target GPC curve profile; and wherein the first polyethylene resin is characterized by the first % MVD of equal to or greater than about 100%, by the first % GPCD of equal to or greater than about 15%, or by both the first % MVD of equal to or greater than about 100% and the first % GPCD of equal to or greater than about 15%;

(e) selecting a second value for one or more parameters of the plurality of parameters for at least one of the one or more reaction zones based on the first % MVD being equal to or greater than about 100%, based on the first % GPCD being equal to or greater than about 15%, or based on both the first % MVD being equal to or greater than about 100% and the first % GPCD being equal to or greater than about 15%;

(f) operating the at least one of the one or more reaction zones independently at the second value of the one or more parameters of the plurality of parameters to produce a second polyethylene resin that is a second multimodal resin:

wherein the second polyethylene resin is characterized by a second % MVD of less than about 100%, a second % GPCD of less than about 15%, a second melt index that is within 30% of the target melt index, and a second density that is within 2.5% of the target density; and (g) recovering the second polyethylene resin from the one or more reaction zones.

12. The method of claim 11, wherein the dynamic viscosity is determined across a range of shear rate ($\omega_i$) of from about 0.01 s$^{-1}$ to about 1,000 s$^{-1}$.

13. The method of claim 11 further comprising (i) determining the weight average molecular weight ($M_w$) of the first polyethylene resin from the GPC curve profile; and (ii) comparing the $M_w$ of the first polyethylene resin with a target $M_w$, wherein comparing the $M_w$ comprises calculating a first $M_w$ deviation (% $M_w$D) from the target $M_w$, and wherein the first % $M_w$D is calculated using the following equation:

$$\% M_wD = 100 \times \text{Abs}((M_{w,T} - M_{w,P})/M_{w,T})$$

wherein $M_{w,T}$ is the weight average molecular weight ($M_w$) of the target, and wherein $M_{w,P}$ is the $M_w$ of the product.

14. The method of claim 13, wherein the first polyethylene resin is characterized by the first % $M_w$D of equal to or greater than about 20%; and wherein the second value decreases a second % $M_w$D of the second polyethylene resin.

15. The method of claim 13 further comprising forming the second polyethylene resin into a pipe or a film; wherein the second polyethylene resin is characterized by the second % $M_w$D of less than about 20%.

16. The method of claim 11, wherein the second polyethylene resin is a bimodal resin.

17. The method of claim 1, further comprising repeating steps (b) through (e) until the second polyethylene resin is characterized by the second % MVD of less than about 15%.

* * * * *